US011219631B2

(12) United States Patent
Tamarkin et al.

(10) Patent No.: US 11,219,631 B2
(45) Date of Patent: *Jan. 11, 2022

(54) FOAMABLE COMPOSITIONS, BREAKABLE FOAMS AND THEIR USES

(71) Applicant: Foamix Pharmaceuticals Ltd., Rehovot (IL)

(72) Inventors: Dov Tamarkin, Maccabim (IL); Enbal Ziv, Gedera (IL); Yohan Hazot, Rehovot (IL); David Schuz, Gimzu (IL)

(73) Assignee: Vyne Pharmaceuticals Inc., Bridgewater, NJ (US)

( * ) Notice: Subject to any disclaimer, the term of this patent is extended or adjusted under 35 U.S.C. 154(b) by 63 days.

This patent is subject to a terminal disclaimer.

(21) Appl. No.: 16/108,799

(22) Filed: Aug. 22, 2018

(65) Prior Publication Data

US 2019/0054106 A1    Feb. 21, 2019

Related U.S. Application Data

(63) Continuation of application No. 15/401,743, filed on Jan. 9, 2017, now Pat. No. 10,092,588, which is a continuation of application No. 14/857,282, filed on Sep. 17, 2015, now Pat. No. 9,572,775, which is a continuation of application No. 13/359,709, filed on Jan. 27, 2012, now Pat. No. 9,167,813, which is a continuation of application No. PCT/IB2010/002241, filed on Jul. 29, 2010.

(60) Provisional application No. 61/229,332, filed on Jul. 29, 2009.

(51) Int. Cl.

| *A61K 31/7056* | (2006.01) |
| *A01N 25/16* | (2006.01) |
| *A61K 9/12* | (2006.01) |
| *A61K 47/10* | (2017.01) |
| *A61K 47/38* | (2006.01) |
| *A61K 31/196* | (2006.01) |
| *A61K 31/327* | (2006.01) |
| *A61K 31/573* | (2006.01) |
| *A61K 31/58* | (2006.01) |
| *A61K 9/00* | (2006.01) |

(52) U.S. Cl.

CPC .......... *A61K 31/7056* (2013.01); *A01N 25/16* (2013.01); *A61K 9/122* (2013.01); *A61K 31/196* (2013.01); *A61K 31/327* (2013.01); *A61K 31/573* (2013.01); *A61K 31/58* (2013.01); *A61K 47/10* (2013.01); *A61K 47/38* (2013.01); *A61K 9/0014* (2013.01)

(58) Field of Classification Search

None
See application file for complete search history.

(56) References Cited

U.S. PATENT DOCUMENTS

| 1,159,250 A | 11/1915 | Moulton |
| 1,666,684 A | 4/1928 | Carstens |
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese et al. |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brightenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienkiewicz |
| 3,263,867 A | 8/1966 | Lehmann |
| 3,263,869 A | 8/1966 | Corsette |

(Continued)

FOREIGN PATENT DOCUMENTS

| AU | 198780257 A | 9/1986 |
| AU | 782515 B2 | 12/2005 |

(Continued)

OTHER PUBLICATIONS

"Everything but the Olive." The Olive Oil Source 1998-2016 [online]. Retrieved from the Internet: http://www.oliveoilsource.com/pageA chemical-characteristics.

"Suppositories?" CareCure Community, SCI Forum [online]. http://sci.rutgers.edu/forum/showthread.php?4176-Suppositories. Published: Apr. 16, 2002, 3 pages.

1058. Benzalkonium Chloride; 2350. Citric Acid; 6143. Methyl Salicylate. The Merck Index: An Encyclopedia of Chemicals, Drugs, and Biologicals. 13th Edition, 2001, pp. 181, 405-406, 1090-1091, 1556.

(Continued)

*Primary Examiner* — David J Blanchard
*Assistant Examiner* — Sarah J Chickos
(74) *Attorney, Agent, or Firm* — Finnegan, Henderson, Farabow, Garrett & Dunner, LLP

(57) ABSTRACT

A substantially surface active agent-free foamable composition which includes short-chain alcohol, water, polymer, fatty alcohol or fatty acid or a combination of fatty alcohol and fatty acid and propellant. A substantially surface active agent-free foamable composition which includes, water, polymer, fatty alcohol or fatty acid and propellant. A method of treatment using a substantially surface active agent-free foamable compositions.

37 Claims, No Drawings

(56) References Cited

U.S. PATENT DOCUMENTS

| | | |
|---|---|---|
| 3,298,919 A | 1/1967 | Bishop et al. |
| 3,301,444 A | 1/1967 | Wittke |
| 3,303,970 A | 2/1967 | Breslau et al. |
| 3,330,730 A | 7/1967 | Hernandez |
| 3,333,333 A | 8/1967 | Noack |
| 3,334,147 A | 8/1967 | Brunelle et al. |
| 3,342,845 A | 9/1967 | Sayigh et al. |
| 3,346,451 A | 10/1967 | Collins et al. |
| 3,366,494 A | 1/1968 | Bower et al. |
| 3,369,034 A | 2/1968 | Chalmers |
| 3,377,004 A | 4/1968 | Wittke |
| 3,383,280 A | 5/1968 | Kuehns |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki |
| 3,563,098 A | 2/1971 | Weber, III |
| 3,574,821 A | 4/1971 | Pfirrmann |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,824,303 A | 7/1974 | Lanzet et al. |
| 3,841,525 A | 10/1974 | Siegel |
| 3,849,569 A | 11/1974 | Mead |
| 3,849,580 A | 11/1974 | Weinstein et al. |
| 3,865,275 A | 2/1975 | De Nunzio |
| 3,866,800 A | 2/1975 | Schmitt |
| 3,878,118 A | 4/1975 | Watson |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,912,667 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,953,591 A | 4/1976 | Snyder |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Showmaker et al. |
| 4,019,657 A | 4/1977 | Spitzer et al. |
| 4,052,513 A | 10/1977 | Kaplan |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,178,373 A | 12/1979 | Klein et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,278,206 A | 7/1981 | Prussin |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,582 A | 4/1982 | Siegel et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,338,211 A | 7/1982 | Stiros |
| 4,352,808 A | 10/1982 | Rane et al. |
| 4,363,806 A | 12/1982 | Bergström et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,607,101 A | 8/1986 | Bernstein |
| 4,612,193 A | 9/1986 | Gordon et al. |
| 4,627,973 A | 12/1986 | Moran et al. |
| 4,628,063 A | 12/1986 | Haines et al. |
| 4,661,340 A | 4/1987 | Nagy née Kricsfalussy et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,772,427 A | 9/1988 | Dawson |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,849,211 A | 7/1989 | Schrauzer |
| 4,851,154 A | 7/1989 | Grollier et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,876,083 A | 10/1989 | Grollier et al. |

(56) References Cited

U.S. PATENT DOCUMENTS

| | | |
|---|---|---|
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,933,330 A | 6/1990 | Jorgensen et al. |
| 4,950,420 A | 8/1990 | Svarz |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,965,063 A | 10/1990 | Casey et al. |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 4,996,193 A | 2/1991 | Hewitt et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,160,665 A | 11/1992 | Owada et al. |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,090 A | 4/1993 | Han |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,530 A | 6/1993 | Janchitraponvej et al. |
| 5,221,534 A | 6/1993 | DesLauriers et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,294,365 A | 3/1994 | Welch et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,318,774 A | 6/1994 | Alban et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A | 1/1995 | Henkin |
| 5,385,943 A | 1/1995 | Nazzaro-Porro |
| 5,389,305 A | 2/1995 | Repinec et al. |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,439,670 A | 8/1995 | Purewal et al. |
| 5,439,682 A | 8/1995 | Wivell et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,547,989 A | 8/1996 | Chamness |
| 5,558,872 A | 9/1996 | Jones et al. |
| 5,560,859 A | 10/1996 | Hartmann et al. |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,618,516 A | 4/1997 | Clavenna et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,648,380 A | 7/1997 | Martin |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |

(56) References Cited

U.S. PATENT DOCUMENTS

| | | |
|---|---|---|
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,695,747 A | 12/1997 | Forestier et al. |
| 5,700,396 A | 12/1997 | Suzuki et al. |
| 5,705,472 A | 1/1998 | Hayes et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,741,509 A | 4/1998 | Kushner |
| 5,747,049 A | 5/1998 | Tominaga |
| 5,753,241 A | 5/1998 | Ribier et al. |
| 5,753,245 A | 5/1998 | Fowler et al. |
| 5,753,270 A | 5/1998 | Beauchamp et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,807,571 A | 9/1998 | List |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,854,246 A | 12/1998 | Francois et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,919,830 A | 7/1999 | Gopalkrishnan et al. |
| 5,922,331 A | 7/1999 | Mausner |
| 5,925,669 A | 7/1999 | Katz et al. |
| 5,939,376 A | 8/1999 | Durbut et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,017,912 A | 1/2000 | Bussell |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,060,041 A | 5/2000 | Candau et al. |
| 6,071,536 A | 6/2000 | Suzuki et al. |
| 6,071,541 A | 6/2000 | Murad |
| 6,075,056 A | 6/2000 | Quigley, Jr. et al. |
| 6,080,394 A | 6/2000 | Lin et al. |
| 6,087,310 A | 7/2000 | Heinkel |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret |
| 6,121,210 A | 9/2000 | Taylor |
| 6,126,920 A | 10/2000 | Jones et al. |
| 6,133,327 A | 10/2000 | Kimura et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,662 B1 | 1/2001 | Lanzendörfer et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,217,887 B1 | 4/2001 | Beerse et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,241,971 B1 | 6/2001 | Fox et al. |
| 6,251,369 B1 | 6/2001 | Stoltz |
| 6,258,374 B1 | 7/2001 | Friess et al. |
| 6,261,544 B1 | 7/2001 | Coury et al. |
| 6,264,964 B1 | 7/2001 | Mohammadi |
| 6,270,781 B1 | 8/2001 | Gehlsen |
| 6,271,295 B1 | 8/2001 | Powell et al. |
| 6,274,150 B1 | 8/2001 | Simonnet et al. |
| 6,283,336 B1 | 9/2001 | Dwyer et al. |
| 6,284,802 B1 | 9/2001 | Bissett et al. |
| 6,287,546 B1 | 9/2001 | Reich et al. |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |

(56) References Cited

U.S. PATENT DOCUMENTS

| | | |
|---|---|---|
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,352,727 B1 | 3/2002 | Takahashi |
| 6,355,230 B2 | 3/2002 | Gers-Barlag et al. |
| 6,358,541 B1 | 3/2002 | Goodman |
| 6,358,924 B1 | 3/2002 | Hoffmann |
| 6,364,854 B1 | 4/2002 | Ferrer et al. |
| 6,372,234 B1 | 4/2002 | Deckers et al. |
| 6,375,936 B1 | 4/2002 | Allard et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,423,329 B1 | 7/2002 | Sine et al. |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,433,068 B1 | 8/2002 | Morrison et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,451,777 B1 | 9/2002 | Bradbury et al. |
| 6,455,076 B1 | 9/2002 | Hahn et al. |
| 6,468,989 B1 | 10/2002 | Chang et al. |
| 6,479,058 B1 | 11/2002 | McCadden |
| 6,479,060 B1 | 11/2002 | Jones et al. |
| 6,479,532 B1 | 11/2002 | Kamimura et al. |
| 6,482,810 B1 | 11/2002 | Brem et al. |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,551,604 B1 | 4/2003 | Beck et al. |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,607,716 B1 | 8/2003 | Smith et al. |
| 6,610,315 B2 | 8/2003 | Scholz et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy |
| 6,682,726 B2 | 1/2004 | Marchesi et al. |
| 6,682,750 B2 | 1/2004 | Loeffler et al. |
| 6,691,898 B2 | 2/2004 | Hurray et al. |
| 6,706,290 B1 | 3/2004 | Kajander et al. |
| 6,709,663 B2 | 3/2004 | Espinoza |
| 6,723,309 B1 | 4/2004 | Deane |
| 6,730,288 B1 | 5/2004 | Abram |
| 6,736,860 B2 | 5/2004 | Patel et al. |
| 6,753,000 B2 | 6/2004 | Breton et al. |
| 6,753,013 B1 | 6/2004 | Didriksen et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,841,547 B2 | 1/2005 | Brown et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,897,195 B2 | 5/2005 | Su et al. |
| 6,902,737 B2 | 6/2005 | Quemin et al. |
| 6,911,211 B2 | 6/2005 | Eini et al. |
| 6,914,057 B1 | 7/2005 | Ryan et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,986,883 B2 | 1/2006 | Pellico |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,252,816 B1 | 8/2007 | Angel et al. |
| 7,270,828 B2 | 9/2007 | Masuda et al. |
| 7,455,195 B2 | 11/2008 | Meketa |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,758,888 B2 | 7/2010 | Lapidot et al. |
| 7,793,807 B2 | 9/2010 | Goujon et al. |
| 7,820,145 B2 | 10/2010 | Tamarkin et al. |
| 7,842,791 B2 | 11/2010 | Britten et al. |
| 7,960,416 B2 | 6/2011 | Sato et al. |
| 8,114,385 B2 | 2/2012 | Tamarkin et al. |
| 8,119,106 B2 | 2/2012 | Tamarkin et al. |
| 8,119,109 B2 | 2/2012 | Tamarkin et al. |
| 8,119,150 B2 | 2/2012 | Tamarkin et al. |
| 8,158,109 B2 | 4/2012 | Abram et al. |
| 8,192,749 B2 | 6/2012 | Ashley |
| 8,211,874 B2 | 7/2012 | Theobald et al. |
| 8,343,945 B2 | 1/2013 | Tamarkin et al. |
| 8,362,091 B2 | 1/2013 | Tamarkin et al. |
| 8,435,498 B2 | 5/2013 | Tamarkin et al. |
| 8,486,374 B2 | 7/2013 | Tamarkin et al. |
| 8,486,375 B2 | 7/2013 | Tamarkin et al. |
| 8,486,376 B2 | 7/2013 | Friedman et al. |
| 8,512,718 B2 | 8/2013 | Eini et al. |
| 8,518,376 B2 | 8/2013 | Tamarkin et al. |
| 8,518,378 B2 | 8/2013 | Tamarkin et al. |
| 8,592,380 B2 | 11/2013 | Trumbore et al. |
| 8,617,100 B2 | 12/2013 | Eini et al. |
| 8,618,081 B2 | 12/2013 | Tamarkin et al. |

(56) References Cited

U.S. PATENT DOCUMENTS

| | | |
|---|---|---|
| 8,623,330 B2 | 1/2014 | Gurge et al. |
| 8,636,982 B2 | 1/2014 | Tamarkin et al. |
| 8,652,443 B2 | 2/2014 | Varanasi et al. |
| 8,703,105 B2 | 4/2014 | Tamarkin et al. |
| 8,709,385 B2 | 4/2014 | Tamarkin et al. |
| 8,722,021 B2 | 5/2014 | Friedman et al. |
| 8,735,377 B1 | 5/2014 | Sipos |
| 8,741,265 B2 | 6/2014 | Tamarkin et al. |
| 8,778,365 B1 | 7/2014 | Hardas et al. |
| 8,784,780 B2 | 7/2014 | Gurge et al. |
| 8,795,635 B2 | 8/2014 | Tamarkin et al. |
| 8,795,693 B2 | 8/2014 | Tamarkin et al. |
| 8,840,869 B2 | 9/2014 | Friedman et al. |
| 8,846,039 B2 | 9/2014 | Chung et al. |
| 8,859,618 B2 | 10/2014 | Palefsky et al. |
| 8,865,139 B1 | 10/2014 | Tamarkin et al. |
| 8,871,184 B2 | 10/2014 | Tamarkin et al. |
| 8,895,536 B2 | 11/2014 | Bannister et al. |
| 8,900,553 B2 | 12/2014 | Tamarkin et al. |
| 8,900,554 B2 | 12/2014 | Tamarkin et al. |
| 8,945,516 B2 | 2/2015 | Tamarkin et al. |
| 8,992,896 B2 | 3/2015 | Tamarkin et al. |
| 9,050,253 B2 | 6/2015 | Tamarkin et al. |
| 9,072,667 B2 | 7/2015 | Tamarkin et al. |
| 9,101,662 B2 | 8/2015 | Tamarkin et al. |
| 9,132,139 B2 | 9/2015 | Dhuin et al. |
| 9,161,916 B2 | 10/2015 | Tamarkin et al. |
| 9,167,813 B2 | 10/2015 | Tamarkin et al. |
| 9,192,558 B2 | 11/2015 | Chen et al. |
| 9,211,259 B2 | 12/2015 | Friedman et al. |
| 9,265,725 B2 | 2/2016 | Tamarkin et al. |
| 9,265,740 B2 | 2/2016 | Johnston et al. |
| 9,271,930 B2 | 3/2016 | At |
| 9,320,705 B2 | 4/2016 | Tamarkin et al. |
| 9,364,433 B2 | 6/2016 | Andersson et al. |
| 9,439,857 B2 | 9/2016 | Tamarkin et al. |
| 9,474,720 B2 | 10/2016 | Yamamoto |
| 9,492,412 B2 | 11/2016 | Tamarkin et al. |
| 9,539,208 B2 | 1/2017 | Tamarkin et al. |
| 9,539,266 B2 | 1/2017 | Mansouri |
| 9,549,898 B2 | 1/2017 | Tamarkin et al. |
| 9,572,775 B2 | 2/2017 | Tamarkin et al. |
| 9,592,246 B2 | 3/2017 | Salman et al. |
| 9,622,947 B2 | 4/2017 | Tamarkin et al. |
| 9,636,405 B2 | 5/2017 | Tamarkin et al. |
| 9,662,298 B2 | 5/2017 | Tamarkin et al. |
| 9,668,972 B2 | 6/2017 | Tamarkin et al. |
| 9,675,700 B2 | 6/2017 | Tamarkin et al. |
| 9,682,021 B2 | 6/2017 | Tamarkin et al. |
| 9,713,643 B2 | 7/2017 | Friedman et al. |
| 9,724,345 B2 | 8/2017 | Andersson et al. |
| 9,795,564 B2 | 10/2017 | Tamarkin et al. |
| 9,841,142 B2 | 12/2017 | Nair |
| 9,849,142 B2 | 12/2017 | Tamarkin et al. |
| 9,884,017 B2 | 2/2018 | Tamarkin et al. |
| 9,931,328 B2 | 4/2018 | Kandavilli et al. |
| 10,028,949 B2 | 7/2018 | Andersson et al. |
| 10,029,013 B2 | 7/2018 | Tamarkin et al. |
| 10,080,764 B2 | 9/2018 | Mansouri |
| 10,086,080 B2 | 10/2018 | Tamarkin et al. |
| 10,092,588 B2 | 10/2018 | Tamarkin et al. |
| 10,117,812 B2 | 11/2018 | Tamarkin et al. |
| 10,137,200 B2 | 11/2018 | Tamarkin et al. |
| 10,159,686 B2 | 12/2018 | Yamomoto |
| 10,213,384 B2 | 2/2019 | Tamarkin et al. |
| 10,213,443 B2 | 2/2019 | Salman et al. |
| 10,213,512 B2 | 2/2019 | Tamarkin et al. |
| 10,238,746 B2 | 3/2019 | Tamarkin et al. |
| 10,265,404 B2 | 4/2019 | Tamarkin et al. |
| 10,278,917 B2 | 5/2019 | Shevachman et al. |
| 10,322,085 B2 | 6/2019 | Tamarkin et al. |
| 10,322,186 B2 | 6/2019 | Tamarkin et al. |
| 10,350,166 B2 | 7/2019 | Tamarkin et al. |
| 10,350,226 B1 | 7/2019 | Atiba |
| 10,363,216 B2 | 7/2019 | Tamarkin et al. |
| 10,369,102 B2 | 8/2019 | Tamarkin et al. |
| 10,391,108 B2 | 8/2019 | Chen et al. |
| 10,398,641 B2 | 9/2019 | Tamarkin et al. |
| 10,434,046 B2 | 10/2019 | Latta et al. |
| 10,463,742 B2 | 11/2019 | Tamarkin et al. |
| 10,512,608 B2 | 12/2019 | Bommagani et al. |
| 10,517,882 B2 | 12/2019 | Tamarkin et al. |
| 10,543,298 B2 | 1/2020 | Sobral et al. |
| 10,548,890 B2 | 2/2020 | Andersson et al. |
| 10,588,858 B2 | 3/2020 | Tamarkin et al. |
| 10,653,707 B2 | 5/2020 | Mansouri |
| 10,780,046 B2 | 9/2020 | Shevachman et al. |
| 10,967,063 B2 | 4/2021 | Tamarkin et al. |
| 2001/0006654 A1 | 7/2001 | Cannell et al. |
| 2001/0026790 A1 | 10/2001 | Gers-Barlag et al. |
| 2001/0027218 A1 | 10/2001 | Stern et al. |
| 2001/0027981 A1 | 10/2001 | Yquel |
| 2001/0033838 A1 | 10/2001 | Farmer |
| 2001/0036450 A1 | 11/2001 | Verite et al. |
| 2001/0054574 A1 | 12/2001 | Navarro |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0031478 A1 | 3/2002 | Keller et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Halswanter et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0182234 A1 | 12/2002 | Riedel et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0013692 A1 | 1/2003 | Gullans et al. |
| 2003/0017181 A1 | 1/2003 | Rood et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0077301 A1 | 4/2003 | Maibach et al. |
| 2003/0078172 A1 | 4/2003 | Guiramand et al. |
| 2003/0082120 A1 | 5/2003 | Milstein |
| 2003/0108502 A1 | 6/2003 | Uchida et al. |
| 2003/0114520 A1 | 6/2003 | Pereira et al. |
| 2003/0118515 A1 | 6/2003 | Jew et al. |
| 2003/0118527 A1 | 6/2003 | Jager et al. |
| 2003/0129259 A1 | 7/2003 | Mahalingam et al. |
| 2003/0130247 A1 | 7/2003 | Gans et al. |
| 2003/0148949 A1 | 8/2003 | Podolsky |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0185861 A1 | 10/2003 | Hori et al. |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215418 A1 | 11/2003 | Asmus et al. |
| 2003/0215472 A1 | 11/2003 | Bonda et al. |
| 2003/0235597 A1 | 12/2003 | Witham et al. |
| 2004/0002550 A1 | 1/2004 | Mecurio |
| 2004/0018228 A1 | 1/2004 | Fischell et al. |
| 2004/0028752 A1 | 2/2004 | Kamm et al. |
| 2004/0038912 A1 | 2/2004 | Michelet et al. |

(56) References Cited

U.S. PATENT DOCUMENTS

| | | |
|---|---|---|
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0106688 A1 | 6/2004 | Koike et al. |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0198706 A1 | 10/2004 | Carrara |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0258627 A1 | 12/2004 | Riedel et al. |
| 2004/0258628 A1 | 12/2004 | Riedel et al. |
| 2004/0258643 A1 | 12/2004 | Yaqub et al. |
| 2005/0002973 A1 | 1/2005 | Johansson et al. |
| 2005/0002976 A1 | 1/2005 | Wu |
| 2005/0013853 A1 | 1/2005 | Gil-Ad et al. |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0075407 A1 | 4/2005 | Tamarkin et al. |
| 2005/0079139 A1 | 4/2005 | Jacques et al. |
| 2005/0079228 A1 | 4/2005 | Jaiswal et al. |
| 2005/0084551 A1 | 4/2005 | Jensen et al. |
| 2005/0085843 A1 | 4/2005 | Opolski et al. |
| 2005/0100517 A1 | 5/2005 | Sanzgiri et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0148552 A1 | 7/2005 | Ryan et al. |
| 2005/0153943 A1 | 7/2005 | Ashley |
| 2005/0164993 A1 | 7/2005 | Ashley |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0220850 A1 | 10/2005 | Ledergerber et al. |
| 2005/0222090 A1 | 10/2005 | Cheng et al. |
| 2005/0232869 A1 | 10/2005 | Tamarkin et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0276836 A1 | 12/2005 | Wilson et al. |
| 2005/0281749 A1 | 12/2005 | Willcox et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |
| 2006/0024243 A1 | 2/2006 | Arkin et al. |
| 2006/0029565 A1 | 2/2006 | Xu et al. |
| 2006/0051301 A1 | 3/2006 | Galopin et al. |
| 2006/0054634 A1 | 3/2006 | Meketa |
| 2006/0057168 A1 | 3/2006 | Larm et al. |
| 2006/0099151 A1 | 5/2006 | Neubourg |
| 2006/0108377 A1 | 5/2006 | Glynn et al. |
| 2006/0110415 A1 | 5/2006 | Gupta |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0010580 A1 | 1/2007 | De Paoli Ambrosi |
| 2007/0015739 A1 | 1/2007 | Walker et al. |
| 2007/0017696 A1 | 1/2007 | Lin et al. |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0053943 A1 | 3/2007 | Wang et al. |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0111956 A1 | 5/2007 | Matsushima et al. |
| 2007/0134174 A1 | 6/2007 | Irwin et al. |
| 2007/0140998 A1 | 6/2007 | Kato et al. |
| 2007/0140999 A1 | 6/2007 | Puglia et al. |
| 2007/0141086 A1 | 6/2007 | Ohara et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0166274 A1 | 7/2007 | Mazur et al. |
| 2007/0224143 A1 | 9/2007 | Konis |
| 2007/0237724 A1 | 10/2007 | Abram et al. |
| 2007/0264317 A1 | 11/2007 | Yosha et al. |
| 2007/0271235 A1 | 11/2007 | Frank et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0050317 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |

(56) References Cited

U.S. PATENT DOCUMENTS

| | | |
|---|---|---|
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0311167 A1 | 12/2008 | Oronsky et al. |
| 2008/0317679 A1 | 12/2008 | Tamarkin et al. |
| 2009/0017147 A1 | 1/2009 | Lintner et al. |
| 2009/0053290 A1* | 2/2009 | Sand ............... A61K 8/553 424/449 |
| 2009/0061001 A1 | 3/2009 | Hougaz |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0214628 A1 | 8/2009 | De Rijk |
| 2009/0291917 A1 | 11/2009 | Akama et al. |
| 2010/0111879 A1 | 5/2010 | Tamarkin et al. |
| 2010/0221194 A1 | 9/2010 | Loupenok |
| 2010/0247449 A1 | 9/2010 | Graupe et al. |
| 2010/0286417 A1 | 11/2010 | Mendes et al. |
| 2011/0002969 A1 | 1/2011 | Serraima et al. |
| 2011/0097279 A1 | 4/2011 | Tamarkin et al. |
| 2011/0207765 A1 | 8/2011 | Van Den Bussche et al. |
| 2011/0236321 A1 | 9/2011 | Trumbore et al. |
| 2011/0262542 A1 | 10/2011 | Ashley |
| 2012/0064136 A1 | 3/2012 | Baker, Jr. et al. |
| 2012/0082632 A1 | 4/2012 | Phillips et al. |
| 2012/0087872 A1 | 4/2012 | Tamarkin et al. |
| 2012/0093876 A1 | 4/2012 | Ouster, III |
| 2012/0128598 A1 | 5/2012 | Trumbore et al. |
| 2012/0141384 A1 | 6/2012 | Tamarkin |
| 2012/0148503 A1 | 6/2012 | Tamarkin et al. |
| 2012/0156144 A1 | 6/2012 | Tamarkin et al. |
| 2012/0164087 A1 | 6/2012 | Carter |
| 2012/0181201 A1 | 7/2012 | Heggie |
| 2012/0237453 A1 | 9/2012 | Tamarkin et al. |
| 2013/0053353 A1 | 2/2013 | Tamarkin et al. |
| 2013/0064777 A1 | 3/2013 | Tamarkin et al. |
| 2013/0115173 A1 | 5/2013 | Trumbore et al. |
| 2013/0161351 A1 | 6/2013 | Eini et al. |
| 2013/0164225 A1 | 6/2013 | Tamarkin et al. |
| 2013/0189195 A1 | 7/2013 | Tamarkin et al. |
| 2013/0189196 A1 | 7/2013 | Tamarkin et al. |
| 2013/0251644 A1 | 9/2013 | Majhi et al. |
| 2013/0261565 A1 | 10/2013 | Wong et al. |
| 2013/0295022 A1 | 11/2013 | Friedman et al. |
| 2013/0296387 A1 | 11/2013 | Saad |
| 2014/0086848 A1 | 3/2014 | Tamarkin et al. |
| 2014/0121188 A1 | 5/2014 | Tamarkin et al. |
| 2014/0140937 A1 | 5/2014 | Gurge et al. |
| 2014/0182585 A1 | 7/2014 | Tamarkin et al. |
| 2014/0186269 A1 | 7/2014 | Tamarkin et al. |
| 2014/0221320 A1 | 8/2014 | Joks et al. |
| 2014/0228355 A1 | 8/2014 | Kortagere et al. |
| 2014/0242016 A1 | 8/2014 | Binks et al. |
| 2014/0248219 A1 | 9/2014 | Tamarkin et al. |
| 2015/0025060 A1 | 1/2015 | Tamarkin et al. |
| 2015/0098907 A1 | 4/2015 | Tamarkin et al. |
| 2015/0141381 A1 | 5/2015 | Levy et al. |
| 2015/0157586 A1 | 6/2015 | Tamarkin et al. |
| 2015/0164922 A1 | 6/2015 | Tamarkin et al. |
| 2015/0174144 A1 | 6/2015 | Bowser et al. |
| 2015/0196570 A1 | 7/2015 | Tamarkin et al. |
| 2015/0209296 A1 | 7/2015 | Yamamoto |
| 2016/0128944 A1 | 5/2016 | Chawrai et al. |
| 2016/0158261 A1 | 6/2016 | Friedman et al. |
| 2016/0213757 A1 | 7/2016 | Edelson et al. |
| 2016/0279152 A1 | 9/2016 | Chen et al. |
| 2016/0287615 A1 | 10/2016 | Chan et al. |
| 2016/0354473 A1 | 12/2016 | Tamarkin et al. |
| 2016/0361252 A1 | 12/2016 | Franke |
| 2016/0361320 A1 | 12/2016 | Zhao et al. |
| 2017/0014517 A1 | 1/2017 | Tamarkin |
| 2017/0049712 A1 | 2/2017 | Bhalani et al. |
| 2017/0119665 A1 | 5/2017 | Tamarkin et al. |
| 2017/0157175 A1 | 6/2017 | Tamarkin et al. |
| 2017/0172857 A1 | 6/2017 | Tamarkin et al. |
| 2017/0181970 A1 | 6/2017 | Tamarkin et al. |
| 2017/0216334 A1 | 8/2017 | Tamarkin et al. |
| 2017/0231909 A1 | 8/2017 | Tamarkin et al. |
| 2017/0274084 A1 | 9/2017 | Friedman et al. |
| 2017/0348418 A1 | 12/2017 | Tamarkin et al. |
| 2017/0354597 A1 | 12/2017 | Tamarkin et al. |
| 2018/0147218 A1 | 5/2018 | Tamarkin et al. |
| 2018/0214558 A1 | 8/2018 | Tamarkin et al. |
| 2018/0235984 A1 | 8/2018 | Eini et al. |
| 2019/0000980 A1 | 1/2019 | Tamarkin et al. |
| 2019/0008795 A1 | 1/2019 | Waugh |
| 2019/0021697 A1 | 1/2019 | Specht et al. |
| 2019/0022000 A1 | 1/2019 | Tamarkin et al. |
| 2019/0022001 A1 | 1/2019 | Tamarkin et al. |
| 2019/0029958 A1 | 1/2019 | Tamarkin et al. |
| 2019/0054106 A1 | 2/2019 | Tamarkin et al. |
| 2019/0076339 A1 | 3/2019 | Tamarkin et al. |
| 2019/0076451 A1 | 3/2019 | Friedman et al. |
| 2019/0091149 A1 | 3/2019 | Tamarkin et al. |
| 2019/0126027 A1 | 5/2019 | O'Neill |
| 2019/0134204 A1 | 5/2019 | Tamarkin et al. |
| 2019/0255078 A1 | 8/2019 | Chen et al. |
| 2019/0262266 A1 | 8/2019 | Moen et al. |
| 2020/0046739 A1 | 2/2020 | Chen et al. |
| 2020/0222358 A1 | 7/2020 | Sajic et al. |
| 2020/0230035 A1 | 7/2020 | Scherer et al. |
| 2020/0276458 A1 | 9/2020 | Daniels |
| 2020/0289381 A1 | 9/2020 | Neubourg |
| 2021/0000842 A1 | 1/2021 | Eini et al. |
| 2021/0015927 A1 | 1/2021 | Tamarkin et al. |
| 2021/0038517 A1 | 2/2021 | Tamarkin et al. |
| 2021/0069335 A1 | 3/2021 | Tamarkin et al. |
| 2021/0077509 A1 | 3/2021 | Tamarkin et al. |
| 2021/0205212 A1 | 7/2021 | Tamarkin et al. |

FOREIGN PATENT DOCUMENTS

| | | |
|---|---|---|
| CA | 2114537 A1 | 2/1993 |
| CA | 2154438 A1 | 1/1996 |
| CA | 2422244 A1 | 9/2003 |
| CA | 2502986 A1 | 5/2004 |
| CA | 2534372 A1 | 10/2005 |
| CH | 639913 A5 | 12/1983 |
| CN | 1528326 A | 9/2004 |
| DE | 1 882 100 U | 11/1963 |
| DE | 1926796 A1 | 3/1970 |
| DE | 2 608 226 A1 | 9/1977 |
| DE | 4140474 A1 | 6/1993 |
| DE | 10009233 A1 | 8/2000 |
| DE | 10138495 A1 | 2/2003 |
| DE | 102004016710 A1 | 10/2005 |
| EP | 0 052 404 A2 | 5/1982 |
| EP | 0 156 507 A1 | 10/1985 |
| EP | 0 186 453 A2 | 7/1986 |
| EP | 0 213 827 A2 | 3/1987 |
| EP | 0 214 865 A2 | 3/1987 |
| EP | 0 270 316 A2 | 6/1988 |
| EP | 0 297 436 A2 | 1/1989 |
| EP | 0 336 812 A2 | 10/1989 |
| EP | 0 414 920 A1 | 3/1991 |
| EP | 0 211 550 B1 | 4/1991 |
| EP | 0 216 856 B1 | 7/1991 |
| EP | 0 454 102 A2 | 10/1991 |
| EP | 0 326 196 B2 | 3/1992 |
| EP | 0 484 530 A1 | 5/1992 |
| EP | 0 485 299 A1 | 5/1992 |
| EP | 0 488 089 A1 | 6/1992 |
| EP | 0 528 190 A1 | 2/1993 |

(56) References Cited

FOREIGN PATENT DOCUMENTS

| | | |
|---|---|---|
| EP | 0 552 612 A2 | 7/1993 |
| EP | 0 569 773 A2 | 11/1993 |
| EP | 0 404 376 B1 | 3/1994 |
| EP | 0 598 412 A2 | 5/1994 |
| EP | 0 391 124 B1 | 6/1995 |
| EP | 0 662 431 A2 | 7/1995 |
| EP | 0 535 327 B1 | 10/1996 |
| EP | 0 738 516 A1 | 10/1996 |
| EP | 0 757 959 A1 | 2/1997 |
| EP | 0 824 911 A2 | 2/1998 |
| EP | 0 829 259 A1 | 3/1998 |
| EP | 0 676 198 B1 | 10/1998 |
| EP | 0 979 654 A1 | 2/2000 |
| EP | 0 993 827 A1 | 4/2000 |
| EP | 1 025 836 A1 | 8/2000 |
| EP | 1 055 425 A2 | 11/2000 |
| EP | 0 506 197 B2 | 7/2001 |
| EP | 1 215 258 A2 | 6/2002 |
| EP | 1 287 813 A1 | 3/2003 |
| EP | 1 308 169 A1 | 5/2003 |
| EP | 1 375 386 A1 | 1/2004 |
| EP | 0 504 301 B1 | 3/2004 |
| EP | 1 428 521 A2 | 6/2004 |
| EP | 1 438 946 A1 | 7/2004 |
| EP | 1 189 579 B1 | 9/2004 |
| EP | 1 475 381 A1 | 11/2004 |
| EP | 1 500 385 A1 | 1/2005 |
| EP | 1 537 916 A1 | 6/2005 |
| EP | 1 600 185 A1 | 11/2005 |
| EP | 0 928 608 B1 | 3/2006 |
| EP | 1 653 932 A1 | 5/2006 |
| EP | 1 734 927 A1 | 12/2006 |
| EP | 1 758 547 A1 | 3/2007 |
| EP | 1 483 001 B1 | 11/2007 |
| EP | 1 584 324 B1 | 11/2007 |
| EP | 1 889 609 A2 | 2/2008 |
| EP | 1 902 706 A1 | 3/2008 |
| EP | 2 129 383 A1 | 12/2009 |
| EP | 2 422 768 A2 | 2/2012 |
| EP | 2 494 959 A1 | 9/2012 |
| FR | 2 456 522 A | 12/1980 |
| FR | 2 591 331 A1 | 6/1987 |
| FR | 2 640 942 A2 | 6/1990 |
| FR | 2 736 824 A1 | 1/1997 |
| FR | 2 774 595 A1 | 8/1999 |
| FR | 2 789 371 A1 | 8/2000 |
| FR | 2 793 479 A1 | 11/2000 |
| FR | 2 814 959 A1 | 4/2002 |
| FR | 2 833 246 A1 | 6/2003 |
| FR | 2 840 903 A1 | 12/2003 |
| FR | 2 843 373 A1 | 2/2004 |
| FR | 2 845 672 A1 | 4/2004 |
| FR | 2 848 998 A1 | 6/2004 |
| FR | 2 860 976 | 4/2005 |
| FR | 2 915 891 A1 | 11/2008 |
| GB | 808 104 A | 1/1959 |
| GB | 808 105 A | 1/1959 |
| GB | 922 930 A | 4/1963 |
| GB | 933 486 A | 8/1963 |
| GB | 998 490 A | 7/1965 |
| GB | 1 026 831 A | 4/1966 |
| GB | 1 033 299 A | 6/1966 |
| GB | 1 081 949 A | 9/1967 |
| GB | 1 121 358 A | 7/1968 |
| GB | 1 162 684 A | 8/1969 |
| GB | 1 170 152 A | 11/1969 |
| GB | 1 201 918 A | 8/1970 |
| GB | 1 347 950 A | 2/1974 |
| GB | 1 351 761 A | 5/1974 |
| GB | 1 351 762 A | 5/1974 |
| GB | 1 353 381 A | 5/1974 |
| GB | 1 376 649 A | 12/1974 |
| GB | 1 397 285 A | 6/1975 |
| GB | 1 408 036 A | 10/1975 |
| GB | 1 457 671 A | 12/1976 |
| GB | 1 489 672 A | 10/1977 |
| GB | 2 004 746 A | 4/1979 |
| GB | 1 561 423 A | 2/1980 |
| GB | 2 114 580 A | 8/1983 |
| GB | 2 166 651 A | 5/1986 |
| GB | 2 153 686 B | 7/1987 |
| GB | 2 172 298 B | 11/1988 |
| GB | 2 206 099 A | 12/1988 |
| GB | 2 337 461 A | 11/1999 |
| GB | 2 367 809 A | 4/2002 |
| GB | 2 406 330 A | 3/2005 |
| GB | 2 406 791 B | 2/2008 |
| GB | 2 474 930 A | 5/2011 |
| IL | 49491 A | 9/1979 |
| IL | 152 486 A | 5/2003 |
| JP | 55-069682 A | 5/1980 |
| JP | 56-039815 A | 4/1981 |
| JP | 57-044429 A | 3/1982 |
| JP | 60-001113 A | 1/1985 |
| JP | 61-275395 A | 12/1986 |
| JP | 62-241701 A | 10/1987 |
| JP | 63-119420 A | 5/1988 |
| JP | 01-100111 A | 4/1989 |
| JP | 01-156906 A | 6/1989 |
| JP | 02-184614 A | 7/1990 |
| JP | 02-255890 A | 10/1990 |
| JP | 03-050289 A | 3/1991 |
| JP | 04-51958 A | 2/1992 |
| JP | 04-282311 A | 10/1992 |
| JP | 04-312521 A | 11/1992 |
| JP | 05-070340 A | 3/1993 |
| JP | 05-213734 A | 8/1993 |
| JP | 06-100414 A | 4/1994 |
| JP | 06-263630 A | 9/1994 |
| JP | 06-329532 A | 11/1994 |
| JP | 07-215835 A | 8/1995 |
| JP | 08-040899 A | 2/1996 |
| JP | 08-501529 A | 2/1996 |
| JP | 08-119831 A | 5/1996 |
| JP | 08-165218 A | 6/1996 |
| JP | 08-277209 A | 10/1996 |
| JP | 09-84855 A | 3/1997 |
| JP | 09-099553 A | 4/1997 |
| JP | 09-110636 A | 4/1997 |
| JP | 10-114619 A | 5/1998 |
| JP | 10-332456 A | 12/1998 |
| JP | 11-501045 A | 1/1999 |
| JP | 11-250543 A | 9/1999 |
| JP | 2000-017174 A | 1/2000 |
| JP | 2000-080017 A | 3/2000 |
| JP | 2000-128734 A | 5/2000 |
| JP | 2000-191429 A | 7/2000 |
| JP | 2000-239140 A | 9/2000 |
| JP | 2000-351726 A | 12/2000 |
| JP | 2000-354623 A | 12/2000 |
| JP | 2001-002526 A | 1/2001 |
| JP | 2001-019606 A | 1/2001 |
| JP | 2001-072963 A | 3/2001 |
| JP | 2002-012513 A | 1/2002 |
| JP | 2002-047136 A | 2/2002 |
| JP | 2002-524490 A | 8/2002 |
| JP | 2002-302419 A | 10/2002 |
| JP | 2003-012511 A | 1/2003 |
| JP | 2003-055146 A | 2/2003 |
| JP | 2004-047136 A | 2/2004 |
| JP | 2004-250435 A | 9/2004 |
| JP | 2004-348277 A | 12/2004 |
| JP | 2005-314323 A | 11/2005 |
| JP | 2005-350378 A | 12/2005 |
| JP | 2006-008574 A | 1/2006 |
| JP | 2006-036317 A | 2/2006 |
| JP | 2006-103799 A | 4/2006 |
| JP | 2006-525145 A | 11/2006 |
| JP | 2007-131539 A2 | 5/2007 |
| JP | 2007-155667 A | 6/2007 |
| JP | 2007-326996 A | 12/2007 |
| KR | 0143232 A | 7/1998 |
| KR | 2001-003063 A | 1/2001 |
| NZ | 520014 A | 5/2005 |

(56) References Cited

FOREIGN PATENT DOCUMENTS

| | | |
|---|---|---|
| NZ | 540166 A | 6/2007 |
| RU | 2277501 C2 | 6/2006 |
| UA | 66796 C2 | 7/2001 |
| WO | WO 82/001821 A1 | 6/1982 |
| WO | WO 86/05389 A1 | 9/1986 |
| WO | WO 88/01502 A1 | 3/1988 |
| WO | WO 88/01863 A1 | 3/1988 |
| WO | WO 88/08316 A1 | 11/1988 |
| WO | WO 89/06537 A1 | 7/1989 |
| WO | WO 90/05774 A1 | 5/1990 |
| WO | WO 91/11991 A1 | 8/1991 |
| WO | WO 92/00077 A1 | 1/1992 |
| WO | WO 92/005142 A1 | 4/1992 |
| WO | WO 92/05763 A1 | 4/1992 |
| WO | WO 92/11839 A1 | 7/1992 |
| WO | WO 92/13602 A1 | 8/1992 |
| WO | WO 93/025189 A1 | 12/1993 |
| WO | WO 94/006440 A1 | 3/1994 |
| WO | WO 96/03115 A1 | 2/1996 |
| WO | WO 96/19921 A1 | 7/1996 |
| WO | WO 96/24325 A1 | 8/1996 |
| WO | WO 96/26711 A1 | 9/1996 |
| WO | WO 96/27376 A1 | 9/1996 |
| WO | WO 96/39119 A1 | 12/1996 |
| WO | WO 97/03638 A1 | 2/1997 |
| WO | WO 97/39745 A1 | 10/1997 |
| WO | WO 98/17282 A1 | 4/1998 |
| WO | WO 98/18472 A1 | 5/1998 |
| WO | WO 98/19654 A1 | 5/1998 |
| WO | WO 98/21955 A1 | 5/1998 |
| WO | WO 98/23291 A1 | 6/1998 |
| WO | WO 98/31339 A1 | 7/1998 |
| WO | WO 98/36733 A2 | 8/1998 |
| WO | WO 98/52536 A1 | 11/1998 |
| WO | WO 99/08649 A2 | 2/1999 |
| WO | WO 99/20250 A1 | 4/1999 |
| WO | WO 99/37282 A2 | 7/1999 |
| WO | WO 99/53923 A1 | 10/1999 |
| WO | WO 2000/09082 A1 | 2/2000 |
| WO | WO 2000/15193 A1 | 3/2000 |
| WO | WO 2000/23051 A1 | 4/2000 |
| WO | WO 2000/33825 A2 | 6/2000 |
| WO | WO 2000/38731 A1 | 7/2000 |
| WO | WO 2000/61076 A1 | 10/2000 |
| WO | WO 2000/62776 A1 | 10/2000 |
| WO | WO 2000/72805 A1 | 12/2000 |
| WO | WO 2000/76461 A2 | 12/2000 |
| WO | WO 2001/01949 A1 | 1/2001 |
| WO | WO 2001/05366 A1 | 1/2001 |
| WO | WO 2001/08681 A1 | 2/2001 |
| WO | WO 2001/10961 A1 | 2/2001 |
| WO | WO 2001/53198 A1 | 7/2001 |
| WO | WO 2001/54212 A1 | 7/2001 |
| WO | WO 2001/54679 A2 | 8/2001 |
| WO | WO 2001/62209 A2 | 8/2001 |
| WO | WO 2001/70242 A2 | 9/2001 |
| WO | WO 2001/76579 A1 | 10/2001 |
| WO | WO 2001/82880 A3 | 11/2001 |
| WO | WO 2001/82890 A1 | 11/2001 |
| WO | WO 2001/85102 A2 | 11/2001 |
| WO | WO 2001/85128 A2 | 11/2001 |
| WO | WO 2001/95728 A1 | 12/2001 |
| WO | WO 2002/00820 A1 | 1/2002 |
| WO | WO 2002/07685 A2 | 1/2002 |
| WO | WO 2002/15860 A1 | 2/2002 |
| WO | WO 2002/15873 A2 | 2/2002 |
| WO | WO 2002/24161 A1 | 3/2002 |
| WO | WO 2002/28435 A2 | 4/2002 |
| WO | WO 2002/41847 A1 | 5/2002 |
| WO | WO 2002/43490 A1 | 6/2002 |
| WO | WO 2002/062324 A2 | 8/2002 |
| WO | WO 2002/078667 A1 | 10/2002 |
| WO | WO 2002/087519 A2 | 11/2002 |
| WO | WO 2003/000223 A1 | 1/2003 |
| WO | WO 2003/002082 A1 | 1/2003 |
| WO | WO 2003/005985 A1 | 1/2003 |
| WO | WO 2003/013984 A1 | 2/2003 |
| WO | WO 2003/015699 A2 | 2/2003 |
| WO | WO 2003/051294 A2 | 6/2003 |
| WO | WO 2003/053292 A1 | 7/2003 |
| WO | WO 2003/055445 A2 | 7/2003 |
| WO | WO 2003/055454 A1 | 7/2003 |
| WO | WO 2003/070301 A1 | 8/2003 |
| WO | WO 2003/071995 A1 | 9/2003 |
| WO | WO 2003/075851 A2 | 9/2003 |
| WO | WO 2003/092641 A1 | 11/2003 |
| WO | WO 2003/094873 A1 | 11/2003 |
| WO | WO 2003/097002 A1 | 11/2003 |
| WO | WO 2004/017962 A2 | 3/2004 |
| WO | WO 2004/037197 A2 | 5/2004 |
| WO | WO 2004/037225 A2 | 5/2004 |
| WO | WO 2004/003284 A1 | 8/2004 |
| WO | WO 2004/064769 A2 | 8/2004 |
| WO | WO 2004/064833 A1 | 8/2004 |
| WO | WO 2004/071479 A2 | 8/2004 |
| WO | WO 2004/078158 A2 | 9/2004 |
| WO | WO 2004/078896 A1 | 9/2004 |
| WO | WO 2004/093895 A1 | 11/2004 |
| WO | WO 2004/112780 A1 | 12/2004 |
| WO | WO 2005/009416 A2 | 2/2005 |
| WO | WO 2005/011567 A2 | 2/2005 |
| WO | WO 2005/018530 A2 | 3/2005 |
| WO | WO 2005/032522 A1 | 4/2005 |
| WO | WO 2005/044219 A1 | 5/2005 |
| WO | WO 2005/063224 A1 | 7/2005 |
| WO | WO 2005/065652 A1 | 7/2005 |
| WO | WO 2005/076697 A2 | 8/2005 |
| WO | WO 2005/097068 A1 | 10/2005 |
| WO | WO 2005/102282 A1 | 11/2005 |
| WO | WO 2005/102539 A1 | 11/2005 |
| WO | WO 2005/117813 A1 | 12/2005 |
| WO | WO 2006/003481 A2 | 1/2006 |
| WO | WO 2006/010589 A2 | 2/2006 |
| WO | WO 2006/011046 A1 | 2/2006 |
| WO | WO 2006/020682 A1 | 2/2006 |
| WO | WO 2006/028339 A1 | 3/2006 |
| WO | WO 2006/031271 A2 | 3/2006 |
| WO | WO 2006/045170 A2 | 5/2006 |
| WO | WO 2006/079632 A1 | 8/2006 |
| WO | WO 2006/081327 A2 | 8/2006 |
| WO | WO 2006/091229 A2 | 8/2006 |
| WO | WO 2006/100485 A1 | 9/2006 |
| WO | WO 2006/120682 A2 | 11/2006 |
| WO | WO 2006/121610 A2 | 11/2006 |
| WO | WO 2006/122158 A2 | 11/2006 |
| WO | WO 2006/129161 A2 | 12/2006 |
| WO | WO 2006/131784 A1 | 12/2006 |
| WO | WO 2007/007208 A2 | 1/2007 |
| WO | WO 2007/010494 A1 | 1/2007 |
| WO | WO 2007/012977 A2 | 2/2007 |
| WO | WO 2007/023396 A2 | 3/2007 |
| WO | WO 2007/031621 A2 | 3/2007 |
| WO | WO 2007/039825 A2 | 4/2007 |
| WO | WO 2007/050543 A2 | 5/2007 |
| WO | WO 2007/054818 A2 | 5/2007 |
| WO | WO 2007/072216 A2 | 6/2007 |
| WO | WO 2007/082698 A1 | 7/2007 |
| WO | WO 2007/085902 A2 | 8/2007 |
| WO | WO 2007/099396 A2 | 9/2007 |
| WO | WO 2007/111962 A2 | 10/2007 |
| WO | WO 2008/008397 A2 | 1/2008 |
| WO | WO 2008/010963 A2 | 1/2008 |
| WO | WO 2008/038147 A2 | 4/2008 |
| WO | WO 2008/041045 A1 | 4/2008 |
| WO | WO 2008/075207 A2 | 6/2008 |
| WO | WO 2008/087148 A2 | 7/2008 |
| WO | WO 2008/104734 A1 | 9/2008 |
| WO | WO 2008/110872 A2 | 9/2008 |
| WO | WO 2008/152444 A2 | 12/2008 |
| WO | WO 2009/007785 A2 | 1/2009 |
| WO | WO 2009/069006 A2 | 6/2009 |
| WO | WO 2009/072007 A2 | 6/2009 |
| WO | WO 2009/087578 A2 | 7/2009 |
| WO | WO 2009/090495 A2 | 7/2009 |

(56) References Cited

FOREIGN PATENT DOCUMENTS

| | | |
|---|---|---|
| WO | WO 2009/090558 A2 | 7/2009 |
| WO | WO 2009/098595 A2 | 8/2009 |
| WO | WO 2011/006026 A1 | 1/2011 |
| WO | WO 2011/013008 A2 | 2/2011 |
| WO | WO 2011/013009 A2 | 2/2011 |
| WO | WO 2011/026094 A2 | 3/2011 |
| WO | WO 2011/039637 A2 | 4/2011 |
| WO | WO 2011/039638 A2 | 4/2011 |
| WO | WO 2011/064631 A1 | 6/2011 |
| WO | WO 2011/106026 A1 | 9/2011 |
| WO | WO 2011/138678 A2 | 11/2011 |
| WO | WO 2012/100097 A2 | 7/2012 |
| WO | WO 2012/100097 A3 | 7/2012 |
| WO | WO 2013/136192 A2 | 9/2013 |
| WO | WO 2014/134394 A1 | 9/2014 |
| WO | WO 2014/134427 A1 | 9/2014 |
| WO | WO 2014/151347 A1 | 9/2014 |
| WO | WO 2014/201541 A1 | 12/2014 |
| WO | WO 2015/075640 A1 | 5/2015 |
| WO | WO 2015/114320 A1 | 8/2015 |
| WO | WO 2015/153864 A2 | 10/2015 |
| WO | WO 2016/154232 A2 | 9/2016 |
| WO | WO 2017/029647 A1 | 2/2017 |
| WO | WO 2017/030555 A1 | 2/2017 |
| WO | WO 2017/089809 A1 | 6/2017 |
| WO | WO 2019/014380 A1 | 1/2019 |
| WO | WO 2019/082090 A1 | 5/2019 |
| WO | WO 2020/089891 A1 | 5/2020 |
| WO | WO 2020/130035 A1 | 6/2020 |

OTHER PUBLICATIONS

242. Allantoin, The Merck Index: An Encyclopedia of Chemicals, Drugs, and Biologicals. 10th edition, Merck & Co., Inc., 1983, p. 39.
Abdullah, G.Z. et al. (Jan. 2013) "Carbopol 934, 940 and Ultrez 10 as viscosity modifiers of palm olein esters based nano-scaled emulsion containing ibuprofen" Pak J Pharm Sci, 26(1):75-83.
Abrams et al., "Ciclopirox gel treatment of scalp seborrheic dermatitis," in: Shuster, S. (ed.) Hydroxy-Piridones as Antifungal Agents with Special Emphasis on Onychomycosis. Springer, Berlin, Heidelberg; 1999, Chapter 8, pp. 45-50.
Adachi, "Storage and Oxidative Stability of O/W/ Nano-emulsions," Foods Food Ingredients J. Jpn., 2004, 209(11), 1 page (Abstract).
Adisen et al., "Topical tetracycline in the treatment of acne vulgaris," J Drugs Dermatol., Oct. 2008, 7(10):953-955.
Alcohol SDA 40B, 200 Proof. Material Safety Data Sheets [online]. Retrieved from the Internet: http://www.pharmco-prod.com/pages/MSDS/SDA.sub.--40B.sub.--200.pdf, on Dec. 9, 2008. MSDS 044, Revision 2.1, Revision Date Dec. 2005, 2 pages.
Alcohol, Wikipedia, the free encyclopedia [online]. Last modified on Apr. 23, 2014. Retrieved on May 17, 2014, http://en.wikipedia.org/wiki/Alcohol, 17 pages.
Aldara™ (imiquimod) Cream. Highlights of Prescribing Information, Graceway Pharmaceuticals, LLC, Mar. 2007, 29 pages.
Allantoin, Römpp Online, retrieved on Sep. 23, 2015, https://roempp.thieme.de/roempp4.0/do/data/RD-O 1-01552, 5 pages.
Allen, The Art, Science, and Technology of Pharmaceutical Compounding, pp. 173-185 (1998).
Allen, The Art, Science, and Technology of Pharmaceutical Compounding, 2nd edition, pp. 250, 251, 263, 267-269, 287, 288, 301-305, tables 16-1 and 16-2 (2002).
Al-Mughrabi et al., "Effectiveness of Essential Oils and Their Combinations with Aluminum Starch Octenylsuccinate on Potato Storage Pathogens," TEOP, 2013, 16(1):23-31.
Ambrose et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, Sep. 1991, 35(9):1799-1803.
Aminobenzoic Acid, Knovel, 2006, retrieved on Apr. 18, 2012, http://www.knovel.com/web/portal/knovel_content?p_p_id=EXT_KNOVEL_CONTENT . . . , 2 pages.
Ansel et al., Pharmaceutical Dosage Forms and Drug Delivery Systems, 7th ed., pp. 87-92, 250, 378-380, table 3.3 (1999).
Anton et al., "Water-in-oil nano-emulsion formation by the phase inversion temperature method: a novel and general concept, a new template for nanoencapsulation," Proceedings of the 33rd Annual Meeting and Exposition of the Controlled Release Society, Jul. 2006, Vienna, Austria, 2 pages.
Arct et al., "Common cosmetic hydrophilic ingredients as penetration modifiers of flavonoids," International Journal of Cosmetic Science, Dec. 2002, 24(6):357-366 (Abstract Only).
Arisan, Kozmetic ve Kisisel Bakim Urunleri Grubu, retrieved on Dec. 10, 2008, http://www.arisankimya.com/kozmetik.htm, 8 pages.
Arquad HTL8-MS, AkzoNobel Functional Applications, retrieved on Mar. 18, 2013, Retrieved from the Internet: <URL: http://sc.akzonobel.com/en/fa/Pages/product-detail.aspx?prodID=8764>, 1 page.
Aslam et al. (2015) "Emerging drugs for the treatment of acne" Expert Opin Emerging Drugs, 20:91-101.
Atopic Dermatitis/Eczema, ibabydoc.com, Copyright 2000, retrieved on Jan. 30, 2010, http://www.ibabydoc.com/online/diseaseeczema.asp 6 pages.
Attwood et al., Surfactant Systems: Their chemistry, pharmacy and biology, pp. 1-8 (1993).
Ausburger and Shangraw, "Bubble size analysis of high consistency aerosol foams and its relationship to foam rheology; Effects fo Container Emptying, Propellent Type, and Time," J. Pharma Sci, Apr. 1968, 57(4):624-631.
Austria, et al., "Stability of vitamin C derivatives in solution and topical formulations", Journal of Pharmaceutical and Biomedical Analysis, 1997, 15:795-801.
Barry and Badal, "Stability of minocycline, doxycycline, and tetracycline stored in agar plates and microdilution trays," Current Microbiology, 1978, 1:33-36.
Barry and Woodford, "Comparative bio-availability and activity of proprietary topical corticosteroid preparations: vasoconstrictor assays on thirty-one ointments," British J. Dermatology, 1975, 93:563-571.
Baskaran et al., "Poloxamer-188 improves capillary blood flow and tissue viability in a cutaneous burn wound," J. Surg. Res., 2001, 101(1):56-61.
Beauty Banter, "Interesting list of comedogenic ingredients!!!!!!!!!!!!" QVC blog, Interesting list of comedogenic ingredients, 2014, 1-14.
Bell-Syer et al., "A systematic review of oral treatments for fungal infections of the skin of the feet," J. Dermatology. Treat., 2001, 12:69-74.
Ben-Et and Tatarsky "Application of NMR for the Determination of HLB Values of Nonionic Surfactants," Journal of the American Oil Chemists Society, Mar. 20, 1972, 49:499-500.
Bernstein and Harrison, "Effects of the Immunomodulating Agent R837 on Acute and Latent Herpes Simplex Virus Type 2 Infections," Antimicrobial Agents and Chemotherapy, Sep. 1989, 33(9):1511-1515.
Beuchat (Feb. 1983) "Influence of Water Activity on Growth, Metabolic Activities and Survival of Yeasts and Molds" J Food Prot, 46(2):135-141.
Blaney and Cook, "Topical use of tetracycline in the treatment of acne," Arch Dermatol, Jul. 1976, 112:971-973.
Blute et al., "Phase behaviour of alkyl glycerol ether surfactants", Physikalische Chemie/Physical Chemistry Tenside Surf. Det., 1998, 35(3):207-212.
Boehm et al., "Synthesis of high specific activity [.sup.3 H]-9-cis-retinoic acid and its application for identifying retinoids with unusual binding properties," J. Med. Chem., 1994, 37:408-414.
Bowles et al., "Protection against Minocycline Pigment Formation by Ascorbic Acid (Vitamin C)", Journal of Esthetic Dentistry, vol. 10/No. 4, pp. 182-186 (1998).
Brenes, et al., "Stability of Copigmented Anthocyanins and Ascorbic Acid in a Grape Juice Model System", J. Agric Food Chem, 2005, 53(1):49-56 (Abstract Only).
Brewer, "Gramicidin", 8 Profiles of Drug Substances, Excipients and Related Methodology, 43 pages (1979).

(56) References Cited

OTHER PUBLICATIONS

Brisaert, M. et al. (1996) "Investigation on the chemical stability of erythromycin in solutions using an optimization system" *Pharm World Sci*, 18(5):182-186.
Bronopol, 2-Bromo-2-Nuro-1,3-Propanediol, Chemical land, Jul. 17, 2006, retrieved on Jun. 4, 2011, http://chemicalland21.com/specialtychem/perchem/BRONOPOL.html, 4 pages.
Brown et al., " Structural dependence of flavonoid interactions with Cu2+ ions: implications for their antioxidant properties," Biochem. J., 1998, 330:1173-1178.
Buck and Guth, "Treatment of Vaginal Intraepithelial Neoplasia (Primarily Low Grade) with Imiquimod 5% Cream", Journal of Lower Genital Tract Disease, 2003, 7(3):290-293.
Bucks et al., "Bioavailability of Topically Administered Steroids: A "Mass Balance" Technique," J. Investigative Dermatology, 1988, 91(1):29-33.
Bunker and Dowd, "Alterations in Scalp Blood Flow after the Epicutaneous Application of 3% Minoxidil and 0.1% Hexyl Nicotinate in Alopecia," British Society for Investigative Dermatology, Sep. 1986, 117(5):668-669.
Burn Patients Need Vitamin D Supplements, NUTRAingredients. com, Jan. 23, 2004, retrieved on May 5, 2010, http://www.nutraingredients.com/Research/Burn-patients-need-vitamin-D-supplements, 1page.
Burton and Marshall, "Hypertrichosis due to minoxidil," British J. Dermatology, 1979, 101:593-595.
C12-15 Alkyl Benzoate, Paula's Choice Skincare, retrieved on Oct. 24, 2010, http://ww.cosmeticscop.com/cosmetic-ingredient-dictionary/definition/259/c12-15-alkyl-benzoate.aspx, 1 page.
Calvert, "Foam in Motion", Foams: Physics, Chemistry and Structure, pp. 27-37 (1989).
Campos and Silva, "Ascorbic Acid and Its Derivatives in Cosmetic Formulations", Cosmetics and Toiletries, 2000, 115(6):59-62 (Abstract Only).
Can Tuberous Sclerosis Be Prevented?, Sharecare, 2002, retrieved on Aug. 29, 2013, <URL: http://www.sharecare.com/health/autosomal-dominant-genetic-disorders/can-tuberous-sclerosis-be-prevented;jsessionid=8505791360520A907DE75930E061E60E6>, 2 pages.
Canavan et al. (2016) "Optimizing Non-Antibiotic Treatments for Patients with Acne: A Review" *Dermatol Ther*, 6:555-578.
Carapeti et al., "Topical diltiazem and bethanechol decrease anal sphincter pressure and heal anal fissures without side effects," Dis Colon Rectum, 2000, 43(10):1359-1362.
Carbowax 1000MSDS, Material Safety Data Sheet for Polyethylene glycol 1000 MSDS, last updated Nov. 6, 2008, retrieved on Dec. 13, 2008, http://www.sciencelab.com/xMSDS-Polyethylene.sub.-glycol.sub.-1000-9926-622, 6 pages.
Carelli et al., "Effect of Vehicles on Yohimbine Permeation Across Excised Hairless Mouse Skin", Pharm Acta Helv, Aug. 1978, 73(3):127-134 (Abstract Only).
Causes of Psoriasis, retrieved on Sep. 9, 2010, http://www.quickcare.org/skin/causes-of0psoriasis.html, 3 pages.
Cetearyl Alcohol, Natural Wellbeing, Copyright 2001-2012, retrieved on Apr. 10, 2014, http://www.naturalwellbeing.com/learning-center/Cetearyl_Alcohol, 3 pages.
Chebil et al., "Solubility of Flavonoids in Organic Solvents," J. Chem. Eng. Data, 2007, 52(5):1552-1556 (Abstract Only).
Chemical Characteristics, The Olive Oil Source, ©1998-2015, retrieved on Jun. 12, 2015, http://www.oliveoilsource.com/page/chemical-characteristics, 10 pages.
Cheshire and Freeman, "Disorders of Sweating," Semin Neurol, 2003, 23(4):399-406.
Chevrant-Breton et al., "Etude du Traitement Capillaire «Bioscalin» dans les Alopecies Diffuses de la Femme", Gazette Medicale, 1986, 93(17):75-79 (English Abstract).
Chiang et al., "Bioavailability Assessment of Topical Delivery Systems: In Vitro Delivery of Minoxidil from Prototypical Semi-Solid Formulations", Int. J. Pharm, 1989, 49(2):109-114 (Abstract Only).

Chinnian et al., "Photostability Profiles of Minoxidil Solutions", PDA J. Pharm Sci Technol., Mar.-Apr. 1996, 50(2):94-98 (English Abstract).
Chollet et al., "Development of a Topically Active Imiquimod Formulation", Pharmaceutical Development and Technology, 1999, 4(1):35-43.
Chollet et al., "The Effect of Temperatures on the Solubility of Imiquimod in Isostearic Acid", Abstract 3031, Pharmaceutical Research, Nov. 1997, 14(11 Supplemental):S475.
Chrysos et al., "Effect of nifedipine on rectoanal motility," Dis Colon Rectum, Feb. 1996, 39(2):212-216.
Clobetasol Propionate Cream and Ointment, Apr. 2006, retrieved Jul. 3, 2014, http://dailymed.nlm.nih.gov/dailymed/archives/fdaDrugInfo.cfm?archiveid=994, 7 pages.
Cloez-Tayarani et al., "Differential effect of serotonin on cytokine production in lipopolysaccharide-stimulated human peripheral blood mononuclear cells: involvement of 5-hydroxytryptamine2A receptors," Int. Immunol., 2003, 15:233-240.
Coal Tars and Coal-Tar Pitches, *Report on Carcinogens*, Twelfth Edition, 2011, 3 pages.
Coatzee et al., "Acceptability and feasibility of Micralax® applicators and of methyl cellulose gel placebo for large-scale clinical trials of vaginal microbicides," AIDS, 2001, 15:1837-1842.
Coconut Oil, Wikipedia, the free encyclopedia, retrieved on Jul. 3, 2015, https://en.wikipedia.org/wiki/Coconut_oil, 8 pages.
Codex Standard for Olive Oils and Olive Pomace Oils Codex Stan 33/1981, Adopted in 1981, recently amended 2013, 8 pages.
Cole and Gazewood, "Diagnosis and Treatment of Impetigo," American Family Physical Website, 2007, http://www.aafp.org/afp, 6 pages.
Colloidal Silica, W.R. Grace & Co. Enriching Lives, Everywhere™, 2011, retrieved on Jun. 4, 2011, http://www.grace.com/engineeredmaterials/materialsciences/colloidalsilica/defaultaspx, 4 pages.
Communication of a Notice of Opposition in European Application No. 03772600.7, dated Jan. 13, 2015, 36 pages.
Cook and Mortenson, "Nifedipine for treatment of anal fissures," Dis Colon Rectum, 2000, 43(3):430-431.
Craig, D.Q.M. et al. (1994 Jul) "An investigation into the structure and properties of Carbopol 934 gels using dielectric spectroscopy and oscillatory rheometry" *J Controlled Rel*, 30(3):213-223 (Abstract).
Cremophor A Grades, BASF the Chemical Company, Jan. 2008, 6 pages.
Croda Crop Care, Arlacel 165, 2011, retrieved on Aug. 3, 2015, http://www.crodapersonalcare.com/home.aspx?view=dtl&d=content&s=157&r=401&p=2578&productName=&inciname=&application=&subapplication=&productfunction=&consumerbenefit=&prodID=1926, 2 pages.
Croda Product Care Europe, Cetomacrogol 1000, 2011, retrieved on Aug. 3, 2015, http://www.crodapersonalcare.com/home.aspx?view=dtl&d=content&s=157&r=273&p=1859&productName=&inciname=&chemicaltype=&application=&subapplication=&productfunction=&consumerbenefit=&prodID=27, 1 page.
Crohn's Disease, Merck Manual Home Edition, retrieved on Jan. 16, 2013, <http://www.merckmanuals.com/home/digestive_disorders/inflammatory_bowel_diseases_ibd/crohn_disease.html?qt=crohn's disease&alt=sh>, 3 pages.
Cunha, "Minocycline versus Doxycycline in the treatment of Lyme Neuroborreliosis," Clin. Infect. Diseases, 2000, 30: 237-238.
Dacarbazine, Chemical Book, 2010, retrieved on Oct. 18, 2013, <URL: http://www.chemicalbook.com/ChemicalProductProperty_EN_CB7710656.htm>, 2 pages.
Dalby et al., "Determination of Drug Solubility in Aerosol Propellants," Pharmaceutical Research, 1991, 8(9):1206-1209.
Dawber and Rundegren, "Hypertrichosis in Females Applying Minoxidil Topical Solution and in Normal Controls", JEADV, 2003, 17:271-275.
Declaration Pursuant to 37 C.F.R. §1.132 of Dr. Mohammad Salman, dated Dec. 28, 2015, filed in U.S. Appl. No. 14/074,868.
Declaration Pursuant to 37 C.F.R. §1.132 of Dr. Mohammad Salman, dated May 19, 2016, filed in U.S. Appl. No. 14/074,868.
Declaration Pursuant to 37 C.F.R. §1.132 of Dr. Mohammad Salman, dated Jul. 19, 2016, filed in U.S. Appl. No. 14/074,868.

(56) References Cited

OTHER PUBLICATIONS

Denatonium Benzoate, retrieved Dec. 9, 2008, http://www.newdruginfo.com/pharmaceopeia/usp28/v28230/usp28nf23s0_m-22790.htm, 2 pages.
Dentinger, et al., "Stability of Nifedipine in an Extemporaneously Compounded Oral Solution", American Journal of Health-System Pharmacy, 2003, 60(10):1019-1022 (English Abstract).
Derivative, Merriam Webster Online Dictionary, retrieved on Jul. 5, 2008, http://www.merriam-webster.com/cgi-bin/dictionary?book=dictionary&va=derivative, 1 page.
Devos and Miller, "Antisense Oligonucleotides: Treating neurodegeneration at the Level of RNA," Neurotherapeutics, 2013, 10:486-497.
Diethyltoluamide, Wikipedia, the free encyclopedia, retrieved on Sep. 11, 2015, https://de.wikipedia.org/wiki/Diethyltoluamid, 12 pages.
Dimethylphthalate, Wikipedia, the free encyclopedia, retrieved on Sep. 11, 2015, http://de.wikipedia.org/wiki/Dimethylphthalat, 8 pages.
Disorder, American Heritage Dictionary of the English Language, 2007, retrieved on Oct. 9, 2010, http://www.credoreference.com/entry/hmdictenglang/disorder, 1 page.
Donnelly et al., Novel Delivery Systems for Transdermal and Intradermal Drug Delivery, p. 103.
Draelos, "Antiperspirants and the Hyperhidrosis Patients," Dermatologic Therapy, 2001, 14:220-224.
Drug Index—Dacarbazine, BC Cancer Agency, Jun. 2004, retrieved on Oct. 18, 2013, <URL:http://www.bccancerbc.ca/HPI/DrugDatabase/DrugIndexPro/Dacarbazine.htm>, 6 pages.
Drugfuture, Chemical Index Database, "Sorbitan Esters" Monograph [online]. Retrieved from: http://www.drugfuture.com/chemdata/sorbitan-esters.html, on Jul. 1, 2016, 2 pages.
Durian et al., "Scaling behavior in shaving cream," The American Physical Society, Dec. 1991, 44(12):R7902-7905.
Durmortier et al., "A review of poloxamer 407 pharmaceutical and pharmacological characteristics," Pharmaceutical Res., Dec. 2006, 23(12):2709-2728.
E7023 Ethanol 200 Proof (Absolute), Sigma-Aldrich Co., © 2008, retrieved on Dec. 9, 2008, http://www.sigmaaldrich.com/catalog/ProductDetail.do?N4=E7023SIAL&N5=SEAR-CH.sub.--CONCAT.sub.--PNOBRAND.sub.--KEY&F=SPEC, 2 pages.
Ebadi et al., "Healing effect of topical nifedipine on skin wounds of diabetic rats," DARU, 2003, 11(1):19-22.
Edens et al., "Storage Stability and Safety of Active Vitamin C in a New Dual-Chamber Dispenser", Journal of Applied Cosmetology, 1999, 17(4):136-143 (English Abstract).
Edirisinghe et al., "Effect of fatty acids on endothelium-dependent relaxation in the rabbit aorta", Clin Sci, Aug. 2006, 111(2): 145-51.
Edwards, "Imiquimod in Clinical Practice," J. Am Acad Dermatol., Jul. 2000 43(1, Pt 2):S12-S17 (English Abstract).
Effendy and Maibach "Surfactants and Experimental Irritant Contact Dermatitis." Contact Dermatol., 1995, 33:217-225.
Elias and Ghadially, "The aged epidermal permeability barrier," Clinical Geriatric Medicine, Feb. 2002, 103-120.
Ellis et al., "The Treatment of Psoriasis with Liquor Carbonis Detergens," J. Invest Dermatology, 1948, 10:455-459.
Emulsifiers With HLB Values, The Herbarie, retrieved on Aug. 5, 2009, http://www.theherbarie.com/files/resources-center/formulating/Emulsifiers-.sub.--HLB.sub.--Values.pdf, 3 pages.
Esposito et al., "Nanosystems for Skin Hydration: A Comparative Study," International Journal of Cosmetic Science, 2007, 29: 39-47.
Established ("Approved") Excipients, Encyclopedia of Pharmaceutical Technology, Second Edition, © 2002, vol. 3, 2146-2147.
Ethylene Oxide Derivatives: An Essence of Every Industry, retrieved on Jul. 12, 2011, http://www.emulsifiers.in/ethylene_oxide_derivatives2.htm, 3 pages.
European Patent Application No. 03772600.7 (Patent No. 1556009): Communication of a Notice of Opposition, dated Sep. 23, 2015, 42 pages.
European Patent Application No. 03772600.7 (Patent No. 1556009): Communication of a Notice of Opposition. dated Sep. 24, 2015, 30 pages.
European Patent Application No. 03772600.7 (Patent No. 1556009): Reply of the Patent Proprietor to the Notices of Opposition, dated May 9, 2016, 134 pages.
European Patent Application No. 03772600.7 (Patent No. 1556009): Summons to Attend Oral Proceedings, dated Jun. 30, 2016, 19 pages.
European Patent Application No. 03772600.7 (Patent No. 1556009): Interlocutory Decision in Opposition Proceedings, dated Feb. 3, 2017, 54 pages.
European Patent Application No. 03772600.7 (Patent No. 1556009): Minutes of Oral Proceedings, dated Feb. 3, 2017, 6 pages.
Excessive Sweating, Merck Manual Home Edition, Oct. 2007, retrieved on Apr. 14, 2011, www.merckmanuals.com/home/print/sec18/ch206/ch206c.html, 2 pages.
Fantin et al., "Critical influence of resistance to streptogramin B-type antibiotics on activity of RP 59500 (Quinupristin-dalfopristin) in experimental endocarditis due to *Staphylococcus aureus*," Antimicrob Agents and Chemothery, Feb. 1995, 39:400-405.
Farahmand et al., "Formulation and Evaluation of a Vitamin C Multiple Emulsion", Pharmaceutical Development and Technology, May 2006, 11(2):255-261 (English Abstract).
Flick, Cosmetic and Toiletry Formulations, 2nd Edition, Copyright 1996, vol. 5, 251-309.
Floyd, "Silicone Surfactants: Applicants in the Personal Care Industry," Silicone Surfactants, 1999, Chapter 7, 181-207.
Fluhr et al., "Glycerol accelerates recovery of barrier function in vivo," Acta Derm. Venereol, 1999, 79:418-421.
Foamix Pharmaceuticals Ltd. (May 1, 2017) "Foamix Pharmaceuticals Announces Plans for Additional Phase 3 Trial for FMX101 in Moderate to Severe Acne," Press Release [online]. Retrieved from: http://www.foamix.co.il/news.asp?nodeID=564&itemID=204, on Jun. 12, 2017, 5 pages.
Foamix Pharmaceuticals, Statement: Use of Luviquat FC 370, Approved by Yohan Hazot, May 3, 2016, 3 pages.
Fontana, "Water Activity: Why It is Important for Food Safety," International Conference on Food Safety, Nov. 16-18, 1998, 177-185.
Fontana (Apr. 1999) "Pharmaceutical Applications for Water Activity" *Pharmaceutical Online* [online]. Retrieved from https://www.pharmaceuticalonline.com/doc/pharmaceutical-applications-for-water-activit-..., on Jan. 17, 2018 (4 pages).
Frankel, A.J. et al. (2010) "Coal Tar 2% Foam in Combination with a Superpotent Corticosteroid Foam for Plaque Psoriasis. Case Report and Clinical Implications" *J Clin Aesthet Dermatol*, 3(10):42-45.
Fully-Refined Paraffin Wax (FRP WAX), Industrial Raw Materials LLC, Feb. 21, 2008, retrieved on Aug. 22, 2013, <http://irmwax.com/Wax/Paraffin/fully_refined.asp> 1 page.
Gallarate et al., "On the Stability of Ascorbic Acid in Emulsified Systems for Topical and Cosmetic Use", International Journal of Pharmaceutics, 1999, 188:233-241.
Galligan et al., "Adhesive Polyurethane Liners for Anterior Restorations," J. Dent. Res., Jul.-Aug. 1968, 629-632.
Garti et al. "Sucrose Esters microemulsions," J. Molec. Liquids, 1999, 80:253-296.
Gas Gangrene, Merck Manual Home Edition, 2008, retrieved on Jan. 16, 2013, <http://www.merckmanuals.com/home/infections/bacterial_infections/gas_gangrene.html?qt=gas gangrene&alt=sh>1 page.
Gelbard et al. "Primary Pediatric Hyperhidrosis: A Review of Current Treatment Options," Pediatric Dermatology, 2008, 25(6):591-598.
Gels, UNC: The Pharmaceutics and Compounding Laboratory, retrieved on Aug. 25, 2014, http://pharmlabs.unc.edu/labs/gels/agents/htm, 4 pages.
Ghica, M.V. et al. (2011) "Design and optimization of some collagen-minocycline based hydrogels potentially applicable for the treatment of cutaneous wound infections" *Pharmazie*, 66:853-861.
Gill et al., "Adverse Drug Reactions in a Paediatric Intensive Care Unit," Acta Paediatric, 1995, 84:438-441.

(56) References Cited

OTHER PUBLICATIONS

Gladkikh, "Ascorbic Acid and Methods of Increasing its Stability in Drugs", Translated from Khimiko-Farmatsevticheskii Zhurnal, 1970, 4(12):37-42.
Glaser and Ballard, "Hyperhidrosis: A Comprehensive and Practical Approach to Patient Management," Expert Rev. Dermatol., Oct. 2006, 1(6):773-775.
Google Search Strategy for Minocycline Solubility, retrieved on Aug. 15, 2013, <http://www.googl.com/search?rls=com.microsoft%3Aen-us%3A1E-SearchBox&q-melocycline+solubility>, 1 page.
Graves et al., "Structure of Concentrated Nanoemulsions," The Journal of Chemical Physics, Apr. 1, 2005, 122:134703, 6 pages.
Griffin, "Calculation of HLB Values of Non-Ionic Surfactants," Journal of the Society of Cosmetic Chemists, May 14, 1954, 249-256.
Groveman et al., "Lack of Efficacy of Polysorbate 60 in the Treatment of Male Pattern Baldness", Arch Intern Med, 1985, 145:1454-1458.
Gschnait et al., "Topical Indomethacin Protects from UVB and UVA Irradiation," Arch. Dermatol. Res., 1984, 276:131-132.
Hakan et al., "The protective effect of fish oil enema in acetic acid and ethanol induced colitis," The Turkish Journal of Gastroenterology, 2000, 11(2):155-161.
Hall, "Diaper Area Hemangiomas: A Unique Set of Concerns," retrieved on Dec. 1, 2008, http://members.tripod.com/.about.Michelle.sub.--G/diaper.html, 8 pages.
Hallstar® GMS SE/AS, retrieved on Jun. 4, 2011, http://www.hallstar.com/pis.php?product=1H022, 1 page.
Hammer et al., "Anti-Microbial Activity of Essential Oils and other Plant extracts," J. Applied Microbiology, 1999, 86:985-990.
Hanasono et al., "The Effect of Silicone Gel on Basic Fibroblast Growth Factor Levels in Fibroblast Cell Culture", Arch Facial Plast Surg, vol. 6, pp. 88-23 (2004).
Handbook of Pharmaceutical Excipients 79, 85, 215, 336, 386, 443, 568, 599 (Arthur H. Kibbe ed., 2000).
Hargreaves, "Chemical Formulation, An Overview of Surfactant-Based Preparations Used in Everyday Life", The Royal Society of Chemistry, 2003, 114-115.
Harrison et al., "Effects of cytokines and R-837, a cytokine inducer, on UV-irradiation augmented recurrent genital herpes in guinea pigs", Antiviral Res., 1991, 15(4):315-322.
Harrison et al., "Modification of Immunological Responses and Clinical Disease During Topical R-837 Treatment of Genital HSV-2 Infection," Antiviral Research, 1988, 10:209-224.
Harrison et al., "Pharmacokinetics and Safety of Imiquimod 5% Cream in the Treatment of Actinic Keratoses of the Face, Scalp, or Hands and Arms", Arch. Dermatol. Res., Jun. 2004, 296(1):6-11 (English Abstract).
Harrison et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, Sep. 1994, 38(9):2059-2064.
Harry, "Skin Penetration," The British Journal of Dermatology and Syphilis, 1941, 53:65-82.
Hashim et al., "Tinea versicolor and visceral leishmaniasis," Int J Dermatol., Apr. 1994; 33(4):258-259 (Abstract).
Haute.De, "Substance (INCI-Designation): Triethanolamine" [online]. Retrieved on Sep. 14, 2015, http://www.haut.de/service/inci/anzeige&id=16384&query=Triethanolamine&funktio . . . ; German with English translation, 3 pages.
Haw, "The HLB System: A Time Saving Guide to Surfactant Selection," Presentation to the Midwest Chapter of the Society of Cosmetic Chemists, Mar. 9, 2004, 39 pages.
Healy et al., "Acne vulgaris", Br. Med. J., 308: 831-833, 831 (1994).
Healy, "Gelled Emollient Systems for Controlled Fragrance Release and Enhanced Product Performance," Cosmetics and toiletries, 2002, 117(2): 47-54.
Heart Failure, The Merck Manual, 2008, retrieved Oct. 9, 2010, http://www.merck.com/mmhe/sec03/ch025/ch025a.html, 12 pages.

Helmenstine, "Surfactant Definition—Chemistry Glossary Definition of Surfactant," About.com Chemistry, retrieved on Mar. 5, 2012, http://chemistry.about.com/od/chemistryglossary/g/surfactant.htm, 1 page.
Hepburn, "Cutaneous leishmaniasis," Clin Exp Dermatol, Jul. 2000, 25(5):363-370 (Abstract).
HLB Systems, Pharmcal.tripod.com, retrieved on Sep. 17, 2010, http://pharmcal.tripod.com/ch17.htm, 3 pages.
HLB-Numbers, Sigma Aldrich, 2009, retrieved on Feb. 2, 2009, http://www.sigmaaldrich.com/materials-science/micro-and-nanoelectronics/l- ithography-nanopatterning/h1b-numbers.html, 3 pages.
How to Have a Healthy Libido in Mid-Life and Beyond, GreenWillowTree.com, Jan. 2001, retrieved on Jul. 28, 2012, http://www.greenwillowtree.com/Page.bok?file=libido.html, 5 pages.
Hubbe, Colloidal Silica, Mini-Encyclopedia of Papermaking Wet-End Chemistry: Additives and Ingredients, their Composition, Functions, Strategies for Use, Feb. 1, 2001, retrieved on Jun. 4, 2011, http://www4.ncsu.edu/~hubbe/CSIL.htm, 2 pages.
Human Immunodeficiency Virus Infection, Merck Manual Home Edition, 2008, retrieved on Jan. 16, 2013, <http://www.merckmanuals.com/home/infections/human_immunodeficiency_virus_hiv_infection/human_immunodeficiency_virus_infection.html?qt=human immunodeficiency virus infection&alt=sh >, 11 pages.
Hwang et al., "Isolation and identification of mosquito repellents in *Artemisia vulgaris*," J. Chem. Ecol., 1985, 11: 1297-1306.
ICI Americas Inc., "Meaning of HLB Advantages and Limitations" Chapter 1 in *The HLB System. A Time-Saving Guide to Emulsifier Selection*. Wilmington, Delaware: 1980; pp. 1-4.
Ikuta et al., "Scanning Electron Microscopic Observation of Oil/Wax/Water/Surfactant System", Journal of SCCJ, 2004, 34(4):280-291 (English Abstract).
Indomethacin, Aug. 15, 2009, retrived on Jun. 3, 2011, http://it03.net/com/oxymatrine/down/1249534834.pdf, 3 pages.
Innocenzi et al., "An Open-Label Tolerability and Effacy Study of an Aluminum Sesquichlorhydrate Topical Foam in Axillary and Palmar Primary Hyperhidrosis," Dermatologic Therapy, 2008, 21:S27-S30.
Izquierdo et al. "Formation and Stability of Nano-Emulsions Prepared Using the Phase Inversion Temperature Method," Langmuir, 2002, 18(1):26-30 (Abstract).
Jan, "Troubled Times: Detergent Foam," retrieved on Feb. 9, 2012, http://zetatalk.com/health/thea117c.htm, 2 pages.
Johns Hopkins on Acne https://www.hopkinsmedicine.org/health/conditions-and-diseases/acne, 6 pages, 2019.
Joseph, "Understanding foams & foaming," University of Minnesota, May 1997, http://www.aem.umn.edu/people/faculty/joseph/archive/docs/understandingfoams.pdf, 8 pages.
Kalkan et al., "The Measurement of Sweat Intensity Using a New Technique," Tr. J. of Medical Sciences, 1998, 28:515-517.
Kanamoto et al., "Pharmacokinetics of two rectal dosage forms of ketoprofen in patients after anal surgery," J Pharmacobiodyn., Mar. 1988, 11(3):141-145.
Kang et al., "Enhancement of the Stability and Skin Penetration of Vitamin C by Polyphenol", Immune Netw., Dec. 2004, 4(4):250-254 (English Abstract).
Kanicky, J.R. and D.O. Shah (2002) "Effect of Degree, Type, and Position of Unsaturation on the $pK_a$ of Long-Chain Fatty Acids" *J Colloid and Interface Science*, 256:201-207.
Karasu et al., "Practice Guideline for the Treatment of Patients with Major Depressive Disorder," Second Edition, Apr. 2000, 78 pages.
Kanwar et al., "Treatment of Melasma with Potent Topical Corticosteroids", Dermatology, 188(2):170 (1994). 188(2):170.
Kathon™ CG, Rohm and Haas Personal Care, Jun. 2006, 9 pages.
Kaur et al., "Formulation Development of Self Nanoemulsifying Drug Delivery System (SNEDDS) of Celecoxib for Improvement of Oral Bioavailability," Pharmacophore, 2013, 4(4):120-133.
Kim, "Stability of Minoxidil in Aqueous Solution", Yakhak Hoechi, 1986, 30(5):228-231 (English Abstract).
Kinnunen and Hannuksela, "Skin reactions to hexylene glycol," Contact Dermatitis, Sep. 1989, 21(3):154-158.
Kircik, L.H. and S. Kumar (Aug. 2010) "Scalp Psoriasis" *J Drugs Dermatol*, 9(8 Suppl):s101-s137.

(56) References Cited

OTHER PUBLICATIONS

Kircik et al., "Formulation and Profile of FMX101 4% Minocycline Topical Foam for the Treatment of Acne Vulgaris," J. Clin. Aesthet. Dermatol., 13(4): 14-21 (2020).
Kleber et al., "Practice Guideline for the Treatment of Patients with Substance Use Disorders," Aug. 2006, 276 pages.
Klucel Hydroxypropylcellulose; Chemical and Physical Properties, Hercules Limited, copyright 1986, retrieved on Aug. 25, 2014, http://legacy.library.ucsf.edu/tid/cnf81a99/pdf, 35 pages.
Knight et al., "Topical diltiazem ointment in the treatment of chronic anal fissure," Br. J. Surg., 2001, 88(4):553-556.
Koerber, "Humectants and Water Activity," Water Activity News, 2000, 8 pages.
Kolb, "Emulsifiers, emollients and solubilizers for personal care", pp. 1-9, accessed Jun. 20, 2018.
Kreuter, "Nanoparticles and microparticles for drug and vaccine delivery," J. Anat., 1996, 189:503-505.
Kucharekova et al., "Effect of a lipid-rich emollient containing ceramide 3 in experimentally induced skin barrier dysfunction," Contact Dermatitis, Jun. 2002, 46:331-338.
Kumar et al., "Application of Broad Spectrum Antiseptic Povidone Iodine as Powerful Action: A Review," Journal of Pharmaceutical Science and Technology, 2009, 1(2):48-58.
Kwak et al. "Study of Complete Transparent Nano-Emulsions which Contain Oils." IFSCC Conference, Seoul Korea, Sep. 2003, 3 pages.
Laboratory 6—Characteristics of Surfactants and Emulsions, retrieved on Jan. 29, 2010, http://web.archive.org/web/20000106225413/http://pharmacy.wilkes.edu/kibbeweb/lab7.html, 5 pages.
Lautenschlager, "A Closer Look on Natural Agents: Facts and Future Aspects," Kosmetic Konzept Kosmetische Praxis, 2006, 5:8-10.
Le Vine et al., "Components of the Goeckerman Regimen," Journal of Investigative Dermatology, 1979, 73:170-173.
Lebwohl and Ali, "Treatment of psoriasis. Part 1. Topical therapy and phototherapy," J. Am Acad Dermatol, Oct. 2001, 487-498.
Lebwohl et al., "A randomized, double-blind, placebo-controlled study of clobestasol propionate 0.05% foam in the treatment of nonscalp psoriasis," International Journal of Dermatology, 2002, 41(5): 269-274.
Lee et al., "Historical review of melanoma treatment and outcomes," Clinics in Dermatology, 2013, 31: 141-147.
Lee et al., "The Stabilization of L-Ascorbic Acid in Aqueous Solution and Water-in-Oil-in-Water Double Emulsion by Controlling pH and Electrolyte Concentration," J. Cosmet. Sci., Jan./Feb. 2004, 55:1-12.
Leive et al., "Tetracyclines of various hydrophobicities as a probe for permeability of *Escherichia coli* outer membrane," Antimicrobial Agents and Chemotherapy, 1984, 25:539-544.
Leunapon-F, Leuna-Tenside, Screenshot, retrieved on Sep. 18, 2015, http://www.leuna-tenside.de/2006_7_14_3143/2006_8_7 5750/2006_8_7 241/cas-68439-49-6, 1 page.
Leung and Robinson, "Bioadhesive Drug Delivery," American Chemical Society, 1991, Chapter 23, 350-366.
Li et al., "Solubility Behavior of Imiquimod in Alkanoic Acids", Pharmaceutical Research, Abstract 3029, Nov. 1997,14(11):S475, 2 pages.
Licking Vaginal Dryness Without a Prescription, retrieved on Dec. 14, 2008, http://www.estronautcom/a/vag.sub.--dryness.htm, 3 pages.
Lin et al., "Ferulic acid stabilizes a solution of vitamins c and e and doubles its photoprotection of skin," J Invest Dermatol, 2005, 125:826-832.
Lippacher et al., "Liquid and Semisolid SLN Dispersions for Topical Application: Rheological Characterization," European Journal of Pharmaceutics and Biopharmaceutics, 2004, 58:561-567.
Livingstone and Hubel, "Segregation of form, color, movement, and depth: Anatomy, physiology, and perception," Science, May 1988, 240:740-749.
Lupke and Kemper, "The HET-CAM Test: An Alternative to the Draize Eye Test," FD Chem. Toxic., 1986, 24:495-196.
Lupo, "Antioxidants and Vitamins in Cosmetics", Clinics in Dermatology, 2001, 19:467-473.
Luviquat Polymer Grades, BASF the Chemical Company, May 2012, 32 pages.
Mah et al., "Irrational Use of Skin-Bleaching Products Can Delay the Diagnosis of Leprosy", International Journal of Leprosy and Other Mycobacterial Diseases, vol. 70, No. 2, pp. 119-21 (2002).
Mailer, "Chemistry and quality of olive oil," NSW Dept. of Primary Industries, Aug. 2006, Primefact 227, 1-4.
Martindale: The Complete Drug Reference, 33rd Edition, Jun. 2002, Pharmaceutical Press, pp. 1073 and 1473.
Martindale: The Complete Drug Reference, Thirty-third edition, Bath Press, London, 2002, 1073 and 1473.
Martindale: The Extra Pharmacopoeia, Twenty-eighth edition, The Pharmaceutical Press, London, 1982, 862-864.
Material Safety Data Sheet, Luvitol EHO, Caelo, Nov. 28, 2013, 4 pages.
Material Safety Data Sheet, Butane, Gas Innovations, Sep. 7, 2007, 3 pages.
Material Safety Data Sheet, Carbon Dioxide, Airgas, Feb. 11, 2016, 11 pages.
Material Safety Data Sheet, Dimethyl Ether, Airgas, May 14, 2015, 12 pages.
Material Safety Data Sheet, Hydroxyethyl Cellulose, Sigma-Aldrich, Jan. 14, 2004, http://terpconnect.umd.edu/-choi/MSDS/Sigma-Aldrich/HYDROXYETHYL%2OCELLULOSE, 5 pages.
Material Safety Data Sheet, Hydroxyethyl Cellulose, Sigma-Aldrich, Jan. 2004, 5 pages.
Material Safety Data Sheet, Liquor carbonis detergens, Caelo, Nov. 28, 2013, 5 pages.
Material Safety Data Sheet, Mineral Oil, Macron Fine Chemicals, Oct. 24, 2011, 6 pages.
Material Safety Data Sheet, N-Butane, Airgas, May 7, 2015, 13 pages.
Material Safety Data Sheet, Nitrous Oxide, Airgas, Feb. 11, 2016, 11 pages.
Material Safety Data Sheet, Propane, Airgas, Oct. 20, 2015, 12 pages.
Material Safety Data Sheet, Science Lab.com, Polyethylene Glycol 200, MSDS, Nov. 6, 2008, 6 pages.
Material Safety Data Sheet, USP, Progesterone, Apr. 26, 2006, 5 pages.
McKetta, Encyclopedia of Chemical Processing and Design: vol. 2—Additives to Alpha, 1st Ed., pp. 214-238 (1977).
Mead, "Electrostatic Mechanisms Underlie Neomycin Block of the Cardiac Ryanodine Receptor Channel (RyR2)," Biophysical Journal, 2004, (87): 3814-3825.
The Merck Index: An Encyclopedia of Chemicals, Drugs, and Biologicals 1299-1300, 1638 (13th ed., 2001).
Messenger et al., "Minoxidil: Mechanisms of Action on Hair Growth", British Journal of Dermatology, 2004, 150:186-194.
Metronidazole (Veterinary—Systemic), The United States Pharmacopeial Convention, 2007, retrieved on Sep. 10, 2009, www.usp.org/pdf/EN/veterinary/metronidazole.pdf, 4 pages.
Metz et al., "A Phase I Study of Topical Tempol for the Prevention of Alopecia Induced by Whole Brain Radiotherapy," Clinical Cancer Research, Oct. 2004, 10:6411-6417.
Meucci et al., "Ascorbic Acid Stability in Aqueous Solutions", Acta Vitaminol Enzymol, 1985, 7(3-4):147-153 (English Abstact).
Milton, D.T. et al. (2006) "A Phase I/II Study of Weekly High-Dose Erlotinib in Previously Treated Patients With Nonsmall Cell Lung Cancer" *Cancer*, 107:1034-1041.
Mineral Oil USP, U.S. Department of Health & Human Services, Chemical Abstracts Service Registry No. 8012-95-1, 2011, 7 pages.
Minocycline (DB01017), Drug Bank, Feb 8, 2013, retrieved on Aug. 15, 2013, <http://www.drugbank.ca/drugs/DB01017>, 10 pages.
Minocycline, Wikipedia, the free encyclopedia, retrieved on Oct. 21, 2011, http://en.wikipedia.org/wiki/Minocycline.com, 7 pages.
MMP Inc., International Development and Manufacturing, "Formulating specialties," retrieved on Feb. 2, 2010, http://mmpinc.com, 3 pages.
Molan, "World Wide Wounds: Honey as a topical antibacterial agent for treatment of infected wounds," Dec. 2001, retrieved May 7,

(56) References Cited

OTHER PUBLICATIONS 2008, http://www.worldwidewounds.com/2001/november/Molan/honey-as-topical-agent.html, 13 pages.
*Molins PLC v. Textron Inc.*, 48 F.3d 1172, 33 USPQ2d 1823 (Fed. Cir. 1995), 19 pages.
Morgan et al., "Enhanced Skin Permeation of Sex Hormones with Novel Topical Spray Vehicles," Journal of Pharmaceutical Sciences, Oct. 1998, 87(10):1213-1218.
Mousse, Merriam-Webster Online Dictionary, retrieved on Dec. 8, 2008, http://www.merriam-webster.com/dictionary/mousse, 2 pages.
Musial, W. and A. Kubis (2004) "Carbopols as factors buffering triethanolamine interacting with artificial skin sebum" *Polim Med*, 34(4):17-30 (Abstract).
Natural Skincare Authority, "Disodium EDTA: Cosmetic Toxin Data," 2011, retrieved on Nov. 17, 2013, http://www.natural-skincare-authority.com/DISODIUM-EDTA.html, 4 pages.
Neutrogena Clinical SPF 30 Facial Lifting Wrinkle Treatment, Apr. 28, 2010, retrieved on Sep. 11, 2010, http://www.cosmetoscope.com/2010/04/neutrogea-clinical-with-johnson-johnsons-cytomimic-techology/, 5 pages.
Neves et al., "Rheological Properties of Vaginal Hydrophilic Polymer Gels," *Current Drug Delivery*, 2009, 6:83-92.
New Nanomaterials to Deliver Anticancer Drugs to Cells Developed, Science Daily, Jun. 2007, retrieved on Oct. 14, 2013, <URL: http://www.sciencedaily.com/releases/2007/06/070607112931.htm>, 3 pages.
Nietz, "Molecular orientation at surfaces of solids," J. Phys. Chem., 1928, 32(2): 255-269.
Niram Chemicals, Chemical products—Cetostearyl Alcohol, Cetyl Alcohol, Stearyl Alcohol and Polyethylene Glycol Importer & Supplier, retrieved on Jul. 17, 2012, http://www.indiamart.com/niramchemicals/chemicals.html, 7 pages.
Novartis "Lamisil©" Product Information, T2001-29 [online]. Retrieved from: http://www.fda.gov/downloads/Drugs/DrugSafety/PostmarketDrugSafetyInformationforPatientsandProviders/ucm052213.pdf; Published: Apr. 2001, 8 pages.
O'Neil, The Merck Index an Encyclopedia of Chemicals, Drugs, and Biologicals, p. 153 (2006).
Oh et al., "Antimicrobial activity of ethanol, glycerol monolaurate or lactic acid against *Listeria moncylogenes*," Int. J. Food Microbiology, 1993, 20:239-246.
Olsen et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, Nov. 2007, 57:767-774.
Olux Prescribing Information (2013).
OM-Cinnamate, MakingCosmetics.com, retrieved on Sep. 26, 2009, http://www.makingcosmetics.com/sunscreens/OM-Cinnamate-p102.html, 1 page
Omega-9 Fatty Acids (Oleic Acid), Orthomolecular.org, Dec. 2004, retrieved on Aug. 15, 2014, http://orthomolecular.org/nutrients/omega9.html, 1 page.
Optimization of Nano-Emulsions Production by Microfluidization, European Food Research and Technology. Sep. 2007, 22:5-6 (English Abstract).
Oranje et al., "Topical retapamulin ointment, 1%, versus sodium fusidate ointment, 2%, for impetigo: a randomized, observer-blinded, noninferiority study," Dermatology, 2007, 215(4):331-340.
Osborne and Henke, "Skin Penetration Enhancers Cited in the Technical Literature," Pharm. Technology, Nov. 1997, 21(11):58-86.
Padhi et al., "Phospho-olivines as positive-electrode materials for rechargeable lithium batteries," J. Electrochemical Soc., Apr. 1997, 144(4): 1188-1194.
Padi and Kulkarni, "Minocycline prevents the development of neuropathic pain, but not acute pain: possible anti-inflammatory and antioxidant mechanisms," Eur J. Pharmacol, 2008, 601:79-87.
Pakpayat et al., "Formulation of Ascorbic Acid Microemulsions with Alkyl Polyglycosides", European Journal of Pharmaceutics and Biopharmaceutics, 2009, 72:444-452.

Palamaras and Kyriakis, "Calcium antagonists in dermatology: a review of the evidence and research-based studies," Derm. Online Journal, 2005, 11(2):8.
Pantaris et al., "The lauric (coconut and palmkernal) oils", Vegetable Oils in Food Technology, Chemistry and Technology of Oils and Fats, pp. 157-202 (2002).
Passi et al., "Lipophilic antioxidants in human sebum and aging," Free Radical Research, 2002,36(4):471-477.
Pharmaceutical Benefits Advisory Committee (Pbac) of Australia. PBAC *Public Summary Document—Nov. 2014 Meeting* (5 pages).
Pendergrass et al., "The shape and dimension of the human vagina as seen in three-dimensional vinyl polysiloxane casts," Gynecol Obstet. Invest., 1996, 42(3):178-82 (Abstract).
Penreco, "Intelligent Gel Technology Product Specifications," Rev. Jun. 2016 (2 pages).
Permethrin (Insecticide), Wildpro, retrieved on Jun. 4, 2015, http://wildpro.twycrosszoo.org/S/00Chem/ChComplex/perm.htm, 5 pages.
Perotti et al., "Topical Nifedipine With Lidocaine Ointment vs. Active Control for Treatment of Chronic Anal Fissure," Dis Colon Rectum, 2002, 45(11):1468-1475.
Polystyrene, Wikipedia the free encyclopedia, retrieved Apr. 21, 2014, http://web.archive.org/web/20060312210423/http://en.wikipedia.org/wiki/Polystyrene, 4 pages.
PPG-40-PEG-60 Lanolin Oil, Environmental Working Group, 2010, retrieved on May 19, 2010, http://www.cosmeticsdatabase.com/ingredient/722972/PPG-40-PEG-60_Lanolin_Oil/?ingred06=722972., 3 pages.
Prevent, The American Heritage Dictionary of the English Language, 2007, retrieved on Oct. 9, 2010, http://www.credoreference.com/entry/hmdictenglang/prevent, 1 page.
Product Data Sheet for Meclocycline, bioaustralis fine chemicals, Jun. 28, 2013, 1 page.
Promius™ Pharma LLC (2012) *Scytera™ (coal tar) Foam*, 2%. Product Information Sheet, 1 page.
Prud'Homme et al., Foams: theory, measurements and applications, Marcel Dekker, Inc., 1996, 327-328.
Purcell, "Natural Jojoba Oil Versus Dryness and Free Radicals," Cosmetics and Toiletries Manufacture Worldwide, 1988, 4 pages.
Purdy et al., "Transfusion-transmitted malaria: unpreventable by current donor exclusion guidelines?" Transfusion, Mar. 2004, 44:464.
Raschke et al., "Topical Activity of Ascorbic Acid: From In Vitro Optimization to In Vivo Efficacy", Skin Pharmacology and Physiology, Jul./Aug. 2004, 17(4):200-206 (Abstract).
Ravet et al., "Electroactivity of natural and sythetic triphylite," J. Power Sources, 2001, 97-98: 503-507.
Raymond, "Iodine as an Aerial Disinfectant," J. Hygiene, May 1946, 44(5):359-361.
Reaction Rate, Wikipedia, the free encyclopedia, retrieved on Dec. 18, 2011.
Receptacle, Merriam Webster, retrieved on Jul. 12, 2011, http://www.merriam-webster.com/dictionary/receptacle, 1 page.
Refina, "Viscosity Guide for Paints, Petroleum & Food Products," accessed Mar. 4, 2015, http://www.refina.co.uk/webpdfs/info_docs/Viscosity_guide_chart.pdf, 2 pages.
Regulation (EC) No. 2003/2003 of the European Parliament and of the Council, Official Journal of the European Union, Oct. 13, 2003, 2 pages.
Repa et al. "All-trans-retinol is a ligand for the retinoic acid receptors," Proc. Natl. Acad Sci, USA, Aug. 1993, 90: 7293-7297.
Reregistration Eligibility Decision for Pyrethrins, EPA, Jun. 7, 2006, 108 pages.
Richwald, "Imiquimod", Drugs Today, 1999, 35(7):497 (Abstract).
Rieger and Rhien, "Emulsifier Selection/HLB," Surfactants in Cosmetics, 129, 1997.
Rohstoffinformationen, Hoffmann Mineral, 2008, 8 pages (with English translation).
Rosacea, Clinuvel Pharmaceuticals, 2010, retrieved on Sep. 9, 2010, http://clinuvel.com/skin-conditions/common-skin-conditions/rosacea#h0-6-prevention, 5 pages.
Rowe et al., "Glyceryl Monooleate," Handbook of Pharmaceutical Excipients, 2011, 10 pages, retrieved on Dec. 19, 2011, http://www.medicinescomplete.com/mc/excipients/current/1001938996.htm?q=glyceryl%20monooleate&t=search&ss=text&p=1# hit.

(56) References Cited

OTHER PUBLICATIONS

Rowe et al., "Octyldodecanol," Handbook of Pharmaceutical Excipients, 2011, 9 pages, retrieved on Dec. 19, 2011, URL:http://www.medicinescomplete.com/mc/excipients/current/1001942450.htm?q=octyldodecanol&t=search&ss=text&p=1# hit.
Rowe et al., "Sucrose Palmitate," Handbook of Pharmaceutical Excipients, 2011, 11 pages, retrieved on Dec. 19, 2011, URL:http://www.medicinescomplete.com/mc/excipients/current/EXP-TD-c46-mn0001.htm?q=sucrose%20stearate&t=search&ss=text&p=1# hit.
Rowe et al., "Sucrose Stearate," Handbook of Pharmaceutical Excipients, 2011, 11 pages, retrieved on Dec. 19, 2011, URL:http://www.medicinescomplete.com/mc/excipients/current/EXP-TD-c11-mnOOOI-mnOOOI.htm?q=sucrose%20stearate&t=search&ss=text&p=3# hit.
RSES (Oil in Refrigerator Systems, Service Application Manual, 2009).
Rutledge, "Some corrections to the record on insect repellents and attractants," J. Am. Mosquito Control Assoc, Dec. 1988, 4(4): 414-425.
Sakai et al., "Characterization of the physical properties of the stratum corneum by a new tactile sensor," Skin Research and Technology, Aug. 2000, 6:128-134.
Sanders et al., "Stabilization of Aerosol Emulsions and Foams," J. Soc. Cosmet. Chem., 1970, 21:377-391.
Sarkar et al., "A Comparative Study of 20% Azelaic Acid Cream Monotherapy versus a Sequential Therapy in the Treatment of Melasma in Dark-Skinned Patients", Dermatology, 205(3): 249-54 (2002).
Sarpotdar, P.P. et al. (1986 Jan) "Effect of Polyethylene Glycol 400 on the Penetration of Drugs Through Human Cadaver Skin In Vitro" *J Pharma Sci*, 75(1):26-28.
Savin et al., "Tinea versicolor treated with terbinafine 1% solution," Int J. Dermatol, Nov. 1999; 38(11): 863-865.
Schaefer, "Silicone Surfactants," Tenside Surf. Det., 1990, 27(3): 154-158.
Schmidt, "Malassezia furfur: a fungus belonging to the physiological skin flora and its relevance in skin disorders," Cutis, Jan. 1997, 59(1):21-24 (Abstract).
Schmolka, "A review of block polymer surfactants," Journal of the American Oil Chemists Society, Mar. 1977, 54: 110-116.
Schott, "Rheology," Remington's Pharmaceutical Sciences, 17th Edition, 1985, 330-345.
Schutze, "Iodine and Sodium Hypochlorite as Wound Disinfectants," The British Medical Journal, 1915, 921-922.
Sciarra, "Aerosol Technology," *Kirk-Othmer Encyclopedia of Chemical Technology*, Jul. 2012, 20 pages.
Sciarra et al., "Aerosols", Remington: the Science and Practice of Pharmacy, pp. 963-966 (2000).
Scientific Discussion for the Approval of Aldara, EMEA, 2005, 10 pages.
Scott, "A Practical Guide to Equipment Selection and Operating Techniques," Pharmaceutical Dosage Forms: Disperse Systems, vol. 3, Copyright 1998, 291-362.
Scully et al., "Cancers of the oral mucosa treatment and management," Medscape Drugs, Diseases and Procedures, Apr. 20, 2012, retrieved on Oct. 12, 2013, <http://emedicine.medscape.com/article/1075729-treatment>, 10 pages.
Seborrheic Dermatitis, retrieved on Sep. 9, 2010, http://www.cumc.columbia.edu/student/health/pdf/R-S/Seborrhea%20Dermatitis.pdf, 2 pages.
Security Datasheet, Luvitol EHO, Cetearyloctanoat, Nov. 27, 2013, 10 pages.
Sehgal, " Ciclopirox: a new topical pyrodonium antimycotic agent: A double-blind study in superficial dermatomycoses," *British Journal of Dermatology*, 1976, 95:83-88.
Sharp, "Oil," Dictionary of Chemistry, Copyright 1990, 286.
Shear et al., "Pharmacoeconomic analysis of topical treatments for tinea infections," Pharmacoeconomics, Mar. 1995, 7(3):251-267.
Shear, Vocabulary.com, retrieved on Aug. 23, 2013, <URL:https://www.vocabulary.com/dictionary/shear>, 3 pages.

Sheer, Vocabulary.com, retrieved on Aug. 23, 2013, https://www.vocabulary.com/dictionary/sheer, 3 pages.
Shemer, A. et al. (2016) "Topical minocycline foam for moderate to severe acne vulgaris: Phase 2 randomized double-blind, vehicle-controlled study results" *J Am Acad Dermatol*, 74(6):1251-1252.
Sheu et al., "Effect of Tocopheryl Polyethylene Glycol Succinate on the Percutaneous Penetration of Minoxidil from Water/Ethanol/Polyethylene Glycol 400 Solutions," Drug Dev. Ind. Pharm., Jun. 2006, 32(5):595-607 (Abstract).
Shim et al., "Transdermal Delivery of Mixnoxidil with Block Copolymer Nanoparticles," J. Control Release, Jul. 2004, 97(3):477-484 (Abstract).
Shrestha et al., "Forming properties of monoglycerol fatty acid esters in nonpolar oil systems," *Langmuir*, 2006, 22: 8337-8345.
Sigma-Aldrich. http://www.sigmaaldrich.com/catalog/product/sial/p1754?lang=en® ion=. Published:Mar. 5, 2014.
Sigma Aldrich, "Surfactants Classified by HLB Numbers" 2017 [online]. Retrieved from the Internet: www.sigmaaldrich.com/materials-science/material-science-products.html?TablePage=22686648, on Jul. 8, 2017 (3 pages).
Silicone, Oxford Dictionaries Online, retrieved on Apr. 19, 2011, http://www.oxforddictionaries.com/definition/silicone?view=uk, 1 page.
Simoni et al., "Retinoic acid and analogs as potent inducers of differentiation and apoptosis. New promising chemopreventive and chemotherapeutic agents in oncology," Pure Appl Chem., 2001, 73(9):1437-1444.
Simovic et al., "The influence of Processing Variables on Performance of O/W Emulsion Gels Based on Polymeric Emulsifier (Pemulen ®TR-2NF)," International Journal of Cosmetic Science, Dec. 2001, 21(2)119-125 (Abstract).
Smith, "Hydroxy acids and skin again," Soap Cosmetics Chemical Specialties, Sep. 1993, 69(9):54-59.
Smith, "Sore Nipples," Breastfeeding Mom's Sore Nipples / Breastfeeding Basics, retrieved on Feb. 8, 2012, http://breastfeedingbasics.com/articles/sore-nipples, 9 pages.
Softemul-165: Product Data Sheet, Mohini Organics PVT Ltd, retrieved Apr. 10, 2014, http://www.mohiniorganics.com/Softemul165.html#, 1 page.
Solans et al., "Overview of basic aspects of microemulsions," Industrial Applications of Microemulsions, New York, 1997, 1-17.
Solodyn® (Minocycline HCI, USP) Prescribing Information; revised Jun. 2016, 2 pages.
Sonneville-Aubrun et al., "Nanoemulsions: A New Vehicle for Skincare Products," Advances in Colloid and Interface Science, 2004, 108-109:145-149.
SPa Collections, AG & Co. Essential oil workshop, retrieved on Jan. 31, 2010, http://www.agworkshop.com/p3.asp, 1 page.
Squillante et al., "Codiffusion of propylene glycol and dimethyl isosorbide in hairless mouse skin," European J. Pharm. Biopharm., 1998, 46:265-271.
Squire and Goode, "A randomized, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat., Jun. 2002, 13(2):51-60 (Abstract).
Sreenivasa et al., "Preparation and Evaluation of Minoxidil Gels for Topical Application in Alopecia," Indian Journal of Pharmaceutical Sciences, 2006, 68(4):432-436.
Sreenivasan, B. et al. (1956)"Studies on Castor Oil. I. Fatty Acid Composition of Castor Oil" *J Am Oil Chem Soc*, 33:61-66.
Stehle et al., "Uptake of minoxidil from a new foam formulation devoid of propylene glycol to hamster ear hair follicles," J. Invest. Dermatol., 2005, 124(4): A101 (Abstract).
Sugisaka et al., "The Physicochemical Properties of Imiquimod, The First Imidazoquinoline Immune Response Modifier", Pharmaceutical Research, Nov. 1997, 14(11):5475, Abstract 3030.
*Sun Pharmaceutical Industries Ltd.* v. *Eli Lilly and Co.*, 611 F.3d 1381, 95 USPQ2d 1797 (Fed. Cir. 2010),7 pages.
Sung, J.H. et al. (2010) "Gel characterisation and in vivo evaluation of minocycline-loaded wound dressing with enhanced wound healing using polyvinyl alcohol and chitosan" *Intl J Pharmaceut*, 392:232-240.

(56) References Cited

OTHER PUBLICATIONS

Surfactant, Wikipedia, the free encyclopedia, retrieved on Oct. 24, 2010, http://en.wikipedia.org/wiki/Surfacatant, 7 pages.
Tadros, "Surfactants in Nano-Emulsions." Applied Surfactants: Principles and Applications, 2005, 285-308.
Tamarkin, D. (2013) "Foam: A Unique Delivery Vehicle for Topically Applied Formulations" in: *Formulating Topical Applications—a Practical Guide*. Dayan N, Ed., Carol Stream, IL: CT Books, Chapter 9, pp. 233-260.
Tan et al., "Effect of Carbopol and PolyvinYlpyrrolidone on the Mechanical, Rheological, and Release Properties of Bioadhesive Polyethylene Glycol Gels," AAPS PharmSciTech, 2000; 1(3) Article 24, 10 pages.
Tanhehco, "Potassium Channel Modulators as Anti-Inflammatory Agents", Expert Opinion on Therapeutic Patents, Jul. 2001, 11(7):1137-1145 (Abstract).
Tarumoto et al., "Studies on toxicity of hydrocortisone 17-butyrate 21-propionate-1. Acute toxicity of hydrocortisone 17-butyrate 21-propionate and its analogues in mice, rats and dogs (author's transl)," J Toxicol Sci., Jul. 1981, 6:1-16 (Abstract).
Tata et al., "Penetration of Minoxidil from Ethanol Propylene Glycol Solutions: Effect of Application Volume on Occlusion," Journal of Pharmaceutical Sciences, Jun. 1995, 84(6):688-691.
Tata et al., "Relative Influence of Ethanol and Propylene Glycol Cosolvents on Deposition of Minoxidil into the Skin," Journal of Pharmaceutical Sciences, Jul. 1994, 83(10):1508-1510.
Tavss et al., "Anionic detergent-induced skin irritation and anionic detergent-induced pH rise of bovine serum albumin," *J. Soc. Cosmet. Chem.*, Jul./Aug. 1988, 39:267-272.
TCI America, Safety Data Sheet; Product Name: Squalane. Product Code: H0096 [online]. Retrieved from: https://www.spectrumchemical.com/MSDS/TCI-H0096.pdf. Revised: Oct. 6, 2014, 5 pages.
Tea Tree Oil, LookChem, Chemical Abstract No. 68647-73-4, 2012, 2 pages.
Tenjarla, "Microemulsions: An Overview and Pharmaceutical Applications", Crit. Rev. Ther. Drug Carrier Sys., 16(5): 461-521 (1999).
The HLB System—A Time-Saving Guide to Emulsifier Selection, ICI Americas Inc., Mar. 1980, 1-22.
The United States Pharmacopeia: The National Formulary, USP23/NF18, US Pharmacopoeia, Jan. 1995, p. 10-14.
Third Party Submission in Published Patent Application, U.S. Appl. No. 12/014,088, Feb. 4, 2009, 4 pages.
Thorgeirsdottir et al., "Antimicrobial activity of monocaprin: a monoglyceride with potential use as a denture disinfectant," Acta Odontologica Scandinavica, Feb. 2006, 64:21-26 (Abstract only).
Tirumala et al., "Abstract: D28.00011: Enhanced order in thinfilms of Pluronic (A-B-A) and Brij (A-B) Block copolymers blended with poly (acrylic acid)," Session D28: Block Copolymer Thin Films, Mar. 13, 2006, 1 page, Abstract.
Tjulandin, S. et al. (2013) "Phase I, dose-finding study of AZD8931, an inhibitor of EGFR (erbB1), HER2 (erbB2) and HER3 (erbB3) signaling, in patients with advanced solid tumors" *Invest New Drugs*, 32(1):145-153.
Todd et al., "Volatile Silicone Fluids for Cosmetic Formulations," Cosmetics and Toiletries, Jan. 1976, 91:27-32.
Torma et al., "Biologic activities of retinoic acid and 3,4-Didehydroretinoic acid in human keratinocytes are similar and correlate with receptor affinities and transactivation properties," J. Invest. Dermatology, 1994, 102: 49-54.
Torres-Rodriguez, "New topical antifungal drugs," Arch Med Res., Winter 1993, 24(4): 371-375 (Abstract).
Toxicology and Carcinogenesis Studies of T-Butyl Alcohol (CAS No. 75-65-0) in F344/N Rats and B6C3F1 Mice (Drinking Water Studies), May 1995, retrieved on Dec. 9, 2008, http://ntp.niehs.nih.gob/?objectid-=0709F73D-A849-80CA-5FB784E86613576D1, 4 pages.
Trofatter, "Imiqimod in clinical practice", European Journal of Dermatology, Oct./Nov. 1998, 8(7 Supp.):17-19 (Abstract).

Tsai et al., "Drug and Vehicle Deposition from Topical Applications: Use of In Vitro Mass Balance Technique with Minoxidil Solutions", J. Pharm. Sci., Aug. 1992, 81(8):736-743 (Abstract).
Tsai et al., "Effect of Minoxidil Concentration on the Deposition of Drug and Vehicle into the Skin," International Journal of Pharmaceutics, 1993, 96(1-3):111-117 (Abstract).
Tsai et al., "Influence of Application Time and Formulation Reapplication on the Delivery of Minoxidil through Hairless Mouse Skin as Measured in Franz Diffusion Cells," Skin Pharmacol., 1994, 7:270-277.
Tyring, "Immune-Response Modifiers: A New Paradigm in the Treatment of Human Papillomavirus," Current Therapeutic Research, Sep. 2000, 61(9):584-596 (Abstract).
Tzen et al. "Surface Structure and Properties of Plant Seed Oil Bodies," Department of Botany and Plant Sciences, University of California, Riverside, California 92521, Apr. 15, 1992, 9 pages.
Tzen et al., "Lipids, proteins and structure of seed oil bodies from diverse species," Plant Physiol., 1993, 101:267-276.
U.S. Final Office Action for U.S. Appl. No. 11/430,437, Tamarkin et al., dated Dec. 16, 2008, 24 pages.
U.S. Office Action for U.S. Appl. No. 11/430,437, Tamarkin et al., dated May 9, 2008, 27 pages.
U.S. Office Action from U.S. Appl. No. 11/430,599, dated Jul. 28, 2008, 59 pages.
Uner et al., "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel," Pharmazie, 2005, 60:751-755.
United States Standards for Grades of Olive Oil and Olive-Pomace Oil, United States Dept. of Agriculture, Oct. 25, 2010, 21 pages.
Valenta, "Effects of Penetration Enhancers on the In-vitro Percutaneous Absorption of Progesterone," J. Pharm. Pharmacol., 1997, 49: 955-959.
Van Cutsem et al., "The anti-inflammatory effects of ketoconazole," J. Am. Acad. Dermatol., Aug. 1991, 25(2):257-261.
Van Slyke, "On the measurement of buffer values and on the relationship of buffer value to the dissociation constant of the buffer and the concentration and reaction of the buffer solution," J. Biol. Chem., 1922, 52:525-570.
Vera et al., "Scattering optics of Foam," Applied Optics, Aug. 20, 2001, 40(24):4210-4214.
Veron et al., "Stability of Minoxidil Topical Formulations", Ciencia Pharmaceutica, 1992, 2(6):411-414 (Abstract).
Versagel® M Series, Mineral Oil Moisturizing Gels. Product Bulletin, retrieved from https://archive.org/web/, as archived Oct. 15, 2006, 3 pages.
View of NCT01171326 on Dec. 7, 2010, ClinicalTrials.gov archive, Dec. 7, 2010, retrieved on Sep. 9, 2013, http://clinicaltrials.gov/archive/NCT01171326/2010_12_07, 4 pages.
View of NCT01362010 on Jun. 9, 2011, ClinicalTrials.gov archive, Jun. 9, 2011, retrieved on Sep. 9, 2013, < http://clinicaltrials.gov/archive/NCT01362010/2011_06_09>, 3 pages.
Walstra, "Principles of Foam Formation and Stability", Foams: Physics, Chemistry and Structure, pp. 1-15 (1989).
Wang and Chen, "Preparation and surface active properties of biodegradable dextrin derivative surfactants," Colloids and Surfaces A: Physicochemical and Engineering Aspects, 2006, 281(1-3):190-193.
Water Jel Technologies, "Material Safety Data Sheet for Neomycin Antibiotic Ointment," Dec. 1, 2004, 7 pages.
WebMD (2014) "Psoriasis Health Center" [online]. Retrieved Apr. 13, 2015; retrieved from the Internet: http://www.webmd.com/skin-problems-and-treatments/psoriasis/psoriasis-symptoms, 3 pages.
WebMD (2014) "Understanding Rosacea—the Basics" [online]. Retrieved Apr. 13, 2015; retrieved from the Internet: http://www.webmd.com/skin-problems-and-treatments/understanding-rosacea-basics (5 pages).
WebMD (2017) "User Reviews & Ratings—Scytera topical" [online]. Retrieved Mar. 1, 2017; retrieved from the Internet: http://www.webmd.com/drugs/drugreview-151502-Scytera+topical.aspx?drugid=151502&drugname=Scytera+topical&sortby=3 (2 pages).

(56) References Cited

OTHER PUBLICATIONS

Weindl et al., "Hyaluronic acid in the treatment and prevention of skin diseases: molecular biological, pharmaceutical and clinical aspects," Skin Pharmacology and Physiology, 2004, 17: 207-213.
Wenninger et al., "International Cosmetic Ingredient Dictionary and Handbook," The Cosmetic, Toiletry, and Fragrance Association, Washington, DC., 1997, vol. 1, 4 pages.
Wermuth, "Similarity in drugs: reflections on analogue design," Drug Discovery Today, Apr. 2006, 11(7/8):348-354.
What Is CP Serum, Skin Biology, retrieved on Dec. 1, 2008, http://web.archive.org/web/20030810230608/http://www.skinbio.com/cpserum.- html, 21 pages.
What Is TSC?, Tuberous Sclerosis Alliance, Jan. 1, 2005, retrieved on Feb. 6, 2014, http://www.tsalliance.org.pages.aspx?content=2, 3 pages.
Williams et al., "Acne vulgaris," Lancet, 2012, 379:361-372.
Williams et al., "Scale up of an olive/water cream containing 40% diethylene glycol monoethyl ether," Dev. Ind. Pharm., 2000, 26(1):71-77.
Williams et al., "Urea analogues in propylene glycol as penetration enhancers in human skin," International Journal of Pharmaceutics, 1989, 36, 43-50.
Wormser et al., "Protective effect of povidone-iodine ointment against skin lesions induced by sulphur and nitrogen mustards and by non-mustard vesicants," Arch. Toxicol., 1997, 71, 165-170.
Wormser, "Early topical treatment with providone-iodine ointment reduces, and sometimes prevents, skin damage following heat stimulus," Letter to the Editor, Burns, 1998, 24:383.
Wrightson, W.R. et al. (1998) "Analysis of minocycline by high-performance liquid chromatography in tissue and serum" *J Chromatography B*, 706:358-361.
Wu et al., "Interaction of Fatty Acid Monolayers with Cobalt Nanoparticles," Nano Letters, 2004, 4(2): 383-386.
Yamada et al., "Candesartan, an angiotensin II receptor antagonist, suppresses pancreatic inflammation and fibrosis in rats," J. Pharmacol. Exp. Ther., 2003, 307(1):17-23.
Zeichner, J.A. (2010) "Use of Topical Coal Tar Foam for the Treatment of Psoriasis in Difficult-to-treat Areas" *J Clin Aesthet Dermatol*, 3(9):37-40.
Zinc Oxide, Knovel, 2006, retrieved on Apr. 18, 2012, http://www.knovel.com/web/portal/knovel_content?p_p_id=EXT_KNOVEL_CONTENT . . . , 2 pages.
Ziolkowsky, "Moderne Aerosolschaume in der Kosmetik (Modern Aerosol Foams in Chemical and Marketing Aspects)" Seifen-Ole-Fette-Wachse, Aug. 1986, 112(13): 427-429 (with English translation).
Clark, "Acne causes and clinical features," *Clinical Pharmacist*, 2009, vol. 1, pp. 163-167.
ARESTIN® Label (Minocycline hydrochloride) Microspheres (NDA 50781), revised May 2017, 10 pages.
EVOCLIN® Label (clindamycin phosphate) Foam (NDA 050801), revised Apr. 2018, 13 pages.
FDA, Inactive Ingredient Guide (2009) https://wayback.archive-it.org/7993/20170406031208/https://www.fda.gov/Drugs/InformationOnDrugs/ucm113978.htm.
Nafisi, et al., "Perspectives on percutaneous penetration: Silica nanoparticles," Nanotoxicology, Early Online, pp. 1-15 (Oct. 1, 2014).
Napierska et al., The nanosilica hazard; another variable entity, Particle and Fibre Toxicology, vol. 7, article No. 39, pp. 1-32 (2010).
OLUX-E® Label (clobetasol propionate) Foam (NDA 22-013); revised May 2018, 15 pages.
Physicians' Desk Reference, pp. 1909-1911, 3138-39, 3140-42 (62nd/2008 ed., 2007).
Purohit et al., Systemic Tofacitinib Concentrations in Adult Patients with Atopic Dermatitis Treated with 2% Tofacitinib Ointment and Application to Pediatric Study Planning, The Journal of Clinical Pharmacology, 2019, 59(6); 811-820.
Rancan, et al., "Skin Penetration and Cellular Uptake of Amorphous Silica Nanoparticles with Variable Size, Surface Funtionalization, and Colloidal Stability," ACS Nano, vol. 6, pp. 6829-42 (2012).
Rowe et al., eds., Handbook of Pharmaceutical Excipients, pp. 130-131, 150-51, 155-56, 222-23, 325-27, 471-75, 722-24, 737-39, 740-41, 817-20 (Pharmaceutical Press, 5th ed., 2006).
SOLODYN® Label (Minocycline HCI, USP) Extended Release Tablets (NDA 50808), revised Oct. 2013, 21 pages.
Sun et al., "Topical Application of Fingolimod Perturbs Cutaneous Inflammation," The Journal of Immunology, 2016, 3854-3864.
Tan, "Antibacterial Therapy for Acne: A Guide to Selection and Use of Systemic Agents," Am. J. Clin. Dermatol., vol. 4, pp. 307-314 (2003).
Tsuji et al., "Therapeutic Approach to Steroid-Resistant Dermatitis Using Novel Immunomodulator FTY720 (Fingolimod) In Combination with Betamethasone Ointment in NC/Nga Mice," Biol. Pharm. Bull., 2012, 35(8), 1314-1319.

* cited by examiner

FOAMABLE COMPOSITIONS, BREAKABLE FOAMS AND THEIR USES

CROSS-REFERENCE TO RELATED APPLICATIONS

This application is a continuation of U.S. application Ser. No. 15/401,743, filed Jan. 9, 2017, which is a continuation of U.S. application Ser. No. 14/857,282, filed Sep. 17, 2015, which is a continuation of U.S. application Ser. No. 13/359,709, filed Jan. 27, 2012, which is a continuation of International Application No. PCT/1610/02241, filed Jul. 29, 2010, which claims the benefit of U.S. Provisional Application No. 61/229,332 filed Jul. 29, 2009, the contents of all of which are hereby incorporated by reference in their entireties herein.

BACKGROUND

Foam compositions with high amounts of alcohol are known in the art. Alcohol-based compositions are useful because of the anti-microbial properties of alcohol and the ability for alcohol to dissolve certain active agents.

Foams and, in particular, single-phase foams are complicated systems which do not form under all circumstances. Slight shifts in foam composition, such as by the addition of active ingredients or the removal of any of the essential ingredients, may destabilize the foam.

The prior art teaches hydro-alcoholic foam compositions require significant amounts of short-chain alcohols (namely, ethanol, propanol, isopropanol, butanol, iso-butanol, t-butanol and pentanol), water, fatty alcohols, polymer and surfactant to form a foam. These compositions require various surfactants, such as, non-ionic surfactants, anionic, cationic, zwitterionic, amphoteric and ampholytic surfactants, as essential components.

Surfactants are known as essential ingredients in foam compositions because of their amphiphilic properties and because they are considered essential in forming a foam. However, many surfactants are known to be irritating when left on the skin, as they can extract lipids from the skin, thereby damaging skin barrier and exposing the skin to contact with pro-inflammatory factors. (See, *Dermatitis*, Vol. 33(4) 217-225, 11 Apr. 2006, John Wiley & Sons).

Lower alcohols are defatting agents. They are known to extract skin fats, thereby disrupting skin barrier function and causing irritation. They are known to cause skin to become dry and cracked (See, for example, *Industrial Guide to Chemical and Drug Safety*, by T. S. S. Dikshith, Prakash V. Diwan, John Wiley & Sons, Inc., 2003, p. 228-9).

Thus the combination of a short chain alcohol and a surfactant can have a doubly undesirable irritating and defatting effect, as well as the drawback of enhanced delivery of drugs through the skin, which results in increased systemic exposure (which is undesirable for topical treatment of the skin).

Hydro-alcoholic foams, as described in the prior art are inherently thermally unstable, and they will collapse upon exposure to the skin and body (at temperatures around 37° C.). They are therefore commonly termed "quick breaking" foams. Typically, when a quick breaking foam is applied to fingers (as is usually done in order to apply a drug to a target area), it melts and rapidly (on exposure to body temperature of about 37° C.) and collapses leaving behind a small pool of liquid. The thermal instability of the foam makes it difficult to apply to a large target area by first administering the foam to the hands and then spreading the foam onto the affected area.

SUMMARY

The present application relates to foamable formulations and foams and their uses comprising, short chain alcohols ("SCA's"), and especially ethanol. In one or more embodiments the short chain alcohol is ethanol. In one or more embodiments the short chain alcohol is isopropanol. In one or more embodiments the SCA's are needed as part of a drug carrier. For example certain drugs require alcohol in order to solubilize them. In one or more other embodiments, the SCA's are provided to facilitate or enhance the transdermal penetration or delivery of a drug. In one or more additional cases, the SCA's are provided to have a defatting effect at the target site, for example where the site of treatment is oily and the defatting effect of alcohol is desirable.

Unexpectedly, it has been discovered that quality hydro-alcoholic foamable formulations and foams can be achieved, which upon dispensing are thermally stable, for example, as shown by having a collapse time of about 60 seconds or more at 36° C., and yet are easily breakable upon application of shear force, without the presence of significant amounts of standard surface active agents known in the art. In other words contrary to the prior art these foams do not collapse rapidly on exposure to body temperature but remain stable for a sufficient period of time so that they can be conveniently applied to a target site without having to take special precautions, such as only applying the foam to a cold surface. Thus, in one or more embodiments, there is provided a substantially surfactant free hydro-alcoholic foamable formulation or foam. In one or more preferred embodiments the hydro-alcoholic formulations and foams are free of surface active agents. Moreover, it has been further discovered that these formulations and foams can be achieved over a large range of alcohol content. Thus, for certain delivery systems there is provided a surfactant-free foamable composition and foam, comprising about a medium level to about a very high level of content of a short-chain alcohol.

In one or more embodiments there is provided a safe and effective foamable carrier composition and foam comprising a short chain alcohol ("SCA"), water, a foaming booster and a liquefied or compressed gas propellant at a concentration of about 3% to about 30% by weight of the total composition, wherein the percent by weight is based on weight foamable composition; wherein the ratio range of composition other than propellant to propellant is from about 100:3 to about 100:30 In one or more other embodiments there is provided a safe and effective foamable pharmaceutical or cosmetic composition and foam comprising an effective amount of a pharmaceutical or cosmetic agent, a short chain alcohol ("SCA"), water, a foaming booster and a liquefied or compressed gas propellant at a concentration of about 3% to about 30% by weight of the total composition, wherein the percent by weight is based on weight foamable composition; wherein the ratio range of composition other than propellant to propellant is from about 100:3 to about 100:30. The foaming booster surprisingly does not need to include a surfactant; and can include a polymeric agent and at least one fatty alcohol, or at least one a fatty acid or a combination thereof or a synergistic combination of two or more fatty alcohols. The SCA is present in a substantial amount. By a substantial amount, it is meant that the alcohol is present at a % concentration by weight at which it is capable of having a defoaming effect and/or an irritating effect. In one or more embodiments the alcohol is at least about 15% by weight. In other embodiments it is at least about 20%, at least about 25%, at least about 30%, at least about 35%, at least about 40%, at least about 45%, at least about 50%, at least about 55%, or at least about 60% by weight. In one or more embodiments the SCA is at a concentration between about 15% to about 65% by weight, or about 20% to about 60% by weight, preferably between about 25% to about 55% by weight, and more preferably between about 30% to about 50% by weight. The carrier and pharmaceutical composition is substantially surfactant free and preferably does not contain a surfactant.

In one or more embodiments there is provided a substantially surfactant free foamable composition comprising a short chain alcohol, water, a foaming booster comprising a polymer and at least one fatty alcohol or at least one fatty acid or a combination thereof and a liquefied or compressed gas propellant at a concentration of about 3% to about 30% by weight of the total composition. The percent by weight is based on weight foamable composition; wherein the ratio range of composition other than propellant to propellant is from about 100:3 to about 100:30; and wherein upon dispensing the foamable carrier composition forms a foam of quality that is thermally stable at a temperature of 36° C. having a collapse time of about or more than 60 seconds.

In one or more embodiments there is provided a substantially surfactant foamable composition comprising a short chain alcohol, water, a foaming booster comprising a polymer and at least one fatty alcohol or at least one fatty acid or a combination thereof or a synergistic combination of two or more fatty alcohols and a liquefied or compressed gas propellant at a concentration of about 3% to about 30% by weight of the total composition; wherein the percent by weight is based on weight foamable composition; wherein the ratio range of composition other than propellant to propellant is from about 100:3 to about 100:30. In one or more embodiments the ratio between a first fatty alcohol and a second fatty alcohol is between about 11:5 and about 5:11. If there is more than two the ratio between the first (having the highest concentration) and the remaining fatty alcohols is between about 2:1 and about 1:2.

In one or more embodiments there is provided a method of preventing or ameliorating or eliminating or treating or alleviating a dermatological or mucosal disorder, comprising: applying a substantially surfactant free foamable composition to a surface having a dermatological or mucosal disorder in need of treatment, said composition comprising a short chain alcohol, water, a foaming booster comprising a polymer, at least one fatty alcohol or at least one fatty acid or combination thereof or a synergistic combination of two or more fatty alcohols and a liquefied or compressed gas propellant at a concentration of about 3% to about 30% by weight of the total composition; wherein the percent by weight is based on weight foamable composition; wherein the ratio range of composition other than propellant to propellant is from about 100:3 to about 100:30; and wherein upon dispensing the foamable carrier composition forms a foam that is thermally stable at a temperature of 36° C. having a collapse time of about or more than 60 seconds.

Unexpectedly, it has been further discovered that quality hydro foamable formulations and foams, which are substantially free of SCA, can be achieved without the presence of significant amounts of standard surface active agents known in the art, by using the carrier discovered for hydro-alcoholic foams without the SCA. Thus, in one or more embodiments, there is provided a substantially surfactant free hydro foamable formulation or foam. In one or more preferred embodiments the hydro formulations and foams are free of surface active agents.

In one or more embodiments, the foamable formulation is clear and transparent when pressurized by the propellant. In a further embodiment the foamable formulation is clear and transparent prior to addition of one or more active agents at which point it forms a homogenous suspension of active agent. Yet, in certain other embodiments the formulation is a suspension prior to addition of propellant and remains a suspension when pressurized by the propellant.

According to an embodiment the one or more active agents is selected from the group consisting of active herbal extract, an acaricides, an age spot and keratose removing agent, an allergen, an alpha hydroxyl acid, an analgesic agent, an anesthetic, an immunogenic substance, an antiacne agent, an antiallergic agent, an antiaging agent, an antibacterial agent, an antibiotic, an antiburn agent, an anticancer agent, an antidandruff agent, an antidepressant, an antidermatitis agent, an antiedemic anent, an antifungal agent, an antihistamine, an antihelminth agent, an antihyperkeratolyte agent, an anti-infective agent, an antiinflammatory agent, an antiirritant, an antilipemic agent, an antimicrobial agent, an antimycotic agent, an antioxidant, an antiparasitic agent, an anti-pigmentation agent, an antiproliferative agent, an antipruritic agent, an antipsoriatic agent, an antirosacea agent, an antiseborrheic agent, an antiseptic agent, an antiswelling agent, an antiviral agent, an anti-wart agent, an anti-wrinkle agent, an antiyeast agents, an astringent, a beta-hydroxy acid, benzoyl peroxide, benzoyl chloride a, topical cardiovascular agent, a chemotherapeutic agent, a corticosteroid, an immunogenic substance, a dicarboxylic acid, a disinfectant, a fungicide, a hair growth regulator, a haptene, a hormone, a hydroxy acid, an immunosuppressant, an immunoregulating agent, an immunomodulator, an insecticide, an insect repellent, a keratolytic agent, a lactam, a local anesthetic agent, a lubricating agent, a masking agent, a metals, a metal oxide, a mitocide, a neuropeptide, a non-steroidal anti-inflammatory agent, an oxidizing agent, a pediculicide, a peptide, a protein, a photodynamic therapy agent, a radical scavenger, a refatting agent, a retinoid, a sanative, a scabicide, a self tanning agent, silicone talc, a skin protective agent, a skin whitening agent, a steroid, a steroid hormone, a steroidal antiinflammatory agent, a vasoconstrictor, a vasodilator, a vitamin, a vitamin A, a vitamin A derivative, a vitamin B, a vitamin B derivative, a vitamin C, a vitamin C derivative, a vitamin D, a vitamin D derivative, a vitamin D analog, a vitamin F, a vitamin F derivative, a vitamin K, a vitamin K derivative, a wound healing agent and a wart remover and mixtures thereof.

In a further embodiment the active agent is selected from the group consisting of mometasone furoate or betamethasone valerate, diclofenac sodium, metronidazole, benzoyl peroxide, minoxidil.

In an embodiment the composition comprises a fatty alcohol. The fatty alcohol can be a straight chain fatty alcohol, a saturated fatty alcohol, an unsaturated fatty alcohol, a hydroxyl substituted fatty alcohol or a branched fatty alcohol. In an embodiment the fatty alcohol is a therapeutically active fatty alcohol.

In additional embodiments, the foamable composition comprises a fatty acid. The fatty acid can be a straight chain fatty acid, a saturated fatty acid, an unsaturated fatty acid, a hydroxyl fatty acid or a branched fatty acid. In an embodiment the fatty acid is a therapeutically active fatty acid.

According to additional embodiments there is provided a method of producing a foamable composition, including:

1. providing a foamable therapeutic composition including a therapeutic agent at a therapeutically effective concentration, a short chain alcohol, for example, at a concentration of about 20% to about 60% by weight, a hydroalcoholic composition foaming booster (including at least one of a polymer, a fatty alcohol or a fatty acid) and water
2. introducing the foamable composition in an aerosol packaging assembly, comprising of a container, suitable for containing a pressurized product and a valve, capable of extruding a foam; and
3. introducing to the aerosol packaging assembly a liquefied or compressed gas propellant at a concentration of about 3% to about 30% by weight of the total composition.

In one or more certain embodiments the SCA content can be in excess of 60%, or in excess of 65%, however, as the level reaches towards 70% it is harder to prepare a satisfactory formulation and higher levels of hydro-alcoholic foam booster can be appropriate. In certain circumstances having both fatty acid and fatty alcohol may help. The greater challenge to form hydro-alcoholic foamable formulations and foam with very high levels of SCA's is presumably without being bound by any theory because of the defoaming and thermolabile properties of the alcohol, the high level of alcohol and the lower level of water.

According to further embodiments there is provided a method of preventing, treating ameliorating or eliminating a disorder by selecting and releasing on to a convenient surface a safe and effective pharmaceutical or cosmetic foamable composition comprising an effective amount of a pharmaceutical or cosmetic agent, a short chain alcohol ("SCA"), water, a foaming booster and a liquefied or compressed gas propellant at a concentration of about 3% to about 30% by weight of the total composition; directing the released foam on to a target on a patient in need; applying a shear force to and spreading the foam over the target surface such that after a simple rub the foam is no longer visible to the naked eye as it is absorbed rapidly on to the target surface.

According to one of more further embodiments the disorder treated by the foamable composition is selected from the group consisting of a dermatose, a dermatitis, a vaginal disorder, a vulvar disorder, an anal disorder, a disorder of a body cavity, an ear disorder, a disorder of the nose, a disorder of the respiratory system, a bacterial infection, a fungal infection, a viral infection, dermatosis, dermatitis, parasitic infections, disorders of hair follicles and sebaceous glands, scaling papular diseases, benign tumors, malignant tumors, reactions to sunlight, bullous diseases, pigmentation disorders, disorders of cornification, pressure sores, disorders of sweating, inflammatory reactions, xerosis, ichthyosis, an allergy, a burn, a wound, a cut, a chlamydia infection, a gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, a yeast infection, vulvar dystrophy, vulvar intraepithelial neoplasia (VIN), contact dermatitis, osteoarthritis, joint pain, an hormonal disorder, a pelvic inflammation, endometritis, salpingitis, oophoritis, genital cancer, cancer of the cervix, cancer of the vulva, cancer of the vagina, vaginal dryness, dyspareunia, an anal and rectal disease, an anal abscess/fistula, anal cancer, an anal fissure, an anal wart, Crohn's disease, hemorrhoids, anal itch, pruritus ani, fecal incontinence, constipation, polyps of the colon and rectum.

DETAILED DESCRIPTION

Foamable Composition and Foam Properties

The ability to achieve quality foam with a substantial concentration of at least one short chain alcohol without a surfactant is surprising, because, such alcohols are not prone to creating a foam. The challenge is not just to achieve a quality foam but also to attain a formulation that will satisfy a plurality of two, three, four, five, six or more of the following property specifications simultaneously.

1. Uniformity: The composition should be formulated so that it is and can remain uniform without phase separation or precipitation over time. This property is of high importance when the product is intended to be a pharmaceutical product. In some embodiments the formulation is shaken before use and is readily re-homogenized upon shaking so the composition is uniform when dispensed.
2. Flowability: The composition, when placed in an aerosol container and pressurized should be flowable such that it can be expelled through the canister valve. It should preferably also be shakable inside the container. These requirements create a formulation challenge, because low or non-viscous flowable and shakable compositions are prone to undergo phase separation or precipitation.
3. Quality: Upon release from the can, the composition should generate a foam of good or excellent quality having low density and small bubble size.
4. Stability/Breakability: The fine balance between stability and breakability of the foam coming out of the container is very delicate: on one hand the foam should preferable not be "quick breaking", i.e., it should be at least short term stable upon release from the pressurized container and not break as a result of exposure to skin temperature; and on the other hand, it should be "breakable", i.e., it should spread easily, break down and absorb into the skin or membrane upon application of mild shear force.
5. Skin Feeling: To ensure patient compliance the skin feeling after application should be pleasant, and greasy or waxy residues should be minimal
6. Non-irritating: The above requirements should be achieved with the awareness that formulation excipients, especially surfactants, can be irritating, and should preferably be eliminated from the composition or reduced as much as possible.
7. Delivery: Finally, the composition should also be designed to ensure efficient delivery of a therapeutic agent into the target site of treatment.

Based on extensive investigations and trial and error experiments, it has been found that such properties can be achieved for formulations as described below.

Compositions

All % values are provided on a weight (w/w) basis.

In one or more embodiments there is provided a foamable composition including:
1. a short chain alcohol
2. a foaming booster, comprising
   a. at least one fatty alcohol or at least one fatty acid or a combination thereof or a synergistic combination of two or more fatty alcohols; and/or b. about 0.1% to about 5% by weight of at least one polymeric agent selected from a bioadhesive agent, a gelling agent, a film forming agent and a phase change agent;
3. water; and
4. a liquefied or compressed gas propellant.

In one or more other embodiments the fatty acid(s) and fatty alcohol(s) may combine to have a synergistic effect. In one or more further embodiments the fatty acid(s) and fatty acids(s) may combine to have a synergistic effect. In one or more embodiments the synergism is to improve foam quality. In one or more other embodiments the synergism is to improve foam thermal stability. In one or more other embodiments the synergism is to improve foam collapse time, which is can be an indicator of thermal stability.

In one or more embodiments the foamable composition is substantially surfactant free. In one or more other embodiments it is essentially surfactant free, namely a non surfactant composition.

In one or more embodiments the foaming booster combination is a synergistic combination that can improve the foam quality and or thermal stability of the composition.

In one or more embodiments the short chain alcohol, is preferably ethanol. In one or more embodiments the short chain alcohol, is preferably isopropanol. In one or more embodiments the short chain alcohol is at least about 15% by weight of the composition. In one or more embodiments the short chain alcohol is at a concentration of about 20% to about 60% by weight. In one or more embodiments the short chain alcohol is at a concentration of about 30% to about 60% by weight. In one or more embodiments the short chain alcohol is at a concentration of about 40% to about 60% by weight. In one or more other embodiments the SCA is propanol or butanol or a branched chain derivative thereof such as isopropanol or iso-butanol. In one or more embodiments it is a pentanol.

Upon release from an aerosol container, the foamable composition forms an expanded breakable foam suitable for topical administration. In one or more other embodiments the foam is a breakable foam that is thermally stable upon dispensing, for example, as selected by a collapse time of about 60 secs or more; and yet breaks easily upon application of shear force.

The foamable composition is suitable for administration to various body areas, including, but not limited to the skin, a body surface, a body cavity, a mucosal surface, e.g., the mucosa of the nose, mouth and eye, the ear, the respiratory system, the vagina or the rectum (severally and interchangeably termed herein "target site")

According to one or more embodiments, the foamable composition further comprises a cosmetic or a pharmaceutical active agent (severally and interchangeably termed herein "active agent").

In one or more embodiments there is provided a foamable composition including:
1. an active agent at an effective concentration;
2. a short chain alcohol, preferably ethanol, at a concentration of about 20% to about 60% by weight;
3. at least one fatty alcohol or at least one fatty acid or a combination thereof or a synergistic combination of two or more fatty alcohols;
4. about 0.1% to about 5% by weight of at least one polymeric agent selected from a bioadhesive agent, a gelling agent, a film forming agent and a phase change agent;
5. water; and
6. a liquefied or compressed gas propellant.

In one or more other embodiments the polymeric agent can be at a concentration less than about 0.1% by weight of the formulation.

In one or more embodiments, at least a portion of the therapeutic agent is suspended or dissolved evenly throughout the entire composition.

In one or more embodiments, the foam composition is clear and transparent when placed under the pressure of the propellant. In one or more embodiments, the composition is transparent upon pressurization by the gas propellant.

It has been discovered that formulations containing high amount of a SCA (such as ethanol) are not prone to foaming when using combinations of different types of surfactants and different types of polymers. Foams produced were not of quality and/or collapsed rapidly. It was found that the combination of at least two suitable fatty alcohols (e.g. stearyl alcohol with cetyl alcohol or cetyl alcohol with myristyl alcohol) or a combination of at least one fatty alcohol with at least one fatty acid (e.g. stearyl alcohol with stearic acid) or the combination of at least two suitable fatty acids (e.g. myristic acid with stearic acid) produced good to excellent quality short term stable foams in the absence of customary surfactants. It was further discovered that fatty alcohols or fatty acids with a saturated carbon chain of between 14 to 18 carbons or between 16 to 18 carbons combined with cellulose-based polymers have outstanding foam boosting properties. Surprisingly it has also been discovered that at least two fatty alcohols or at least two fatty acids combined with cellulose-based polymers have outstanding foam boosting properties. These foam boosting combinations provide breakable foams of good or excellent quality having enhanced thermal stability at 36° C.

For example, it was found that when myristyl alcohol or cetyl alcohol were used alone in hydro-alcoholic formulations, poor and fairly good foams were obtained respectively. Surprisingly however, when myristyl alcohol was combined with cetyl alcohol at a 1:1 ratio, a short term stable breakable foam of good quality was obtained. Thus, the combination of cetyl and myristyl alcohol combined with a polymeric agent, has a synergistic foam boosting effect.

It was further found that when cetyl alcohol or stearyl alcohol were used alone in hydro-alcoholic formulations combined with a polymeric agent, fairly good and good foams were achieved respectively. Surprisingly however, when stearyl alcohol was combined with cetyl alcohol at a 1:1 ratio, in a formulation containing a polymeric agent, a short term stable breakable foam of excellent quality was obtained. Thus, the combination of cetyl and stearyl alcohol combined with a polymeric agent, has a synergistic foam boosting effect.

Furthermore when stearyl alcohol and stearic acid were each used alone with a polymeric agent in hydro-alcoholic formulations or combined (at a ratio of 1:1) good quality foams were obtained. A short term stable breakable foam having a low density was obtained as a result of said combination.

Thus in one or more embodiments, there is provided a hydro-alcoholic foamable formulation which provides a good to excellent breakable foam. In one or more embodiments the foam displays a collapse time of about 60 sec or more, or of about 90 seconds or more, or of about 120 seconds or more, or of about 150 seconds or more, or of about 180 seconds or more at 36° C. In other words it displays a thermal stability on exposure to a body surface at normal body temperature.

In one or more embodiments the foam displays a collapse time of about 60 seconds or less, or of about 50 seconds or more, or of about 40 seconds or more, or of about 30 seconds or more at 36° C. In one or more other embodiments the foam displays a thermal liability on exposure to a body surface at normal body temperature.

In one or more embodiments the fatty acid or fatty alcohol has 14 to 22 carbon atoms in its carbon chain. In one or more embodiments the fatty acid or fatty alcohol has 16 to 22 carbon atoms in its carbon chain.

In one or more embodiments, there is provided a hydro-alcoholic foamable formulation comprising fatty alcohols or fatty acids combined with cellulose-based polymers having outstanding foam boosting properties.

In one or more embodiments there is provided a foaming booster comprising at least one fatty alcohol or at least one fatty acid or a combination thereof. In one or more embodiments the combination is a synergistic combination. In certain embodiments the synergism results in an improved foam quality. In certain embodiments the synergism results in a thermal stability or in an improved thermal stability. In certain embodiments the thermal stability is exhibited when the composition is placed on a mammal at normal body temperature. In an embodiment the mammal is a human.

In one or more other embodiments the foaming booster consists essentially of at least one fatty alcohol or at least one fatty acid or a combination thereof. In one or more other embodiments the foaming booster consists essentially of at least two fatty alcohols. In one or more other embodiments the foaming booster consists essentially of at least two fatty acids. In one or more other embodiments the foaming booster is between about 1% and about 10% by weight of the composition.

In one or more embodiments the foamable formulation comprises a synergistic combination of two or more fatty alcohols to achieve a foam with thermal stability. In one or more embodiments, the foamable formulation comprises a synergistic combination of two or more fatty acids to achieve a foam with thermal stability. In one or more embodiments the foamable formulation comprises a synergistic combination of at least one fatty acid and at least one fatty alcohol to achieve a foam with thermal stability. In one or more embodiments, the foamable formulation comprises a synergistic combination of two or more fatty alcohols or fatty acids or a fatty acid and fatty alcohol at a ratio of about 1:1. By about it is intended to provide for a variation of 35% or of 30% or of 25% or of 20% or of 10% or of 5% or of 1% or any % between any of these amounts. If there are more than two fatty alcohols then in one or more embodiments the ratio between a first fatty alcohol (having the highest concentration) and the remaining fatty alcohols is between about 2:1 and about 1:2, or if there are more than two fatty acids then in one or more embodiments the ratio between the first fatty acid (having the highest concentration) and the remaining fatty acids is between about 2:1 and about 1:2, or if there is a combination of fatty acids and fatty alcohols and there are more than one of one or both of types in one or more embodiments the ratio between the total fatty alcohols and the total fatty acids is between about 2:1 and about 1:2. In one or more further embodiments the aforesaid ratios are between about 11:5 and about 5:11, or are in certain embodiments are about 1:1.

Furthermore, when stearic acid was used alone in hydro-alcoholic formulations, good quality foams were obtained. When stearic acid was combined with myristic acid at a 1:1 ratio a short term breakable foam of good quality, having a low density was obtained.

In one or more embodiments, there is provided a hydro-alcoholic foamable formulation which provides a good breakable foam which has a collapse time of at least about 60 sec at 36° C., and containing a combination of two or more fatty alcohols combined with a polymeric agent. In one or more embodiments, there is provided a hydro-alcoholic foamable formulation which provides a breakable foam which is thermally stable as seen by having a collapse time of at least about 60 seconds or at least about 85 seconds or at least about 120 seconds; or at least about 180 seconds at 36° C., and containing a combination of two or more fatty acids or a fatty acid with a fatty alcohol combined with a polymeric agent.

In one or more other embodiments the fatty alcohol synergistic combination is cetyl alcohol and myristyl alcohol. In one or more other embodiments the fatty alcohol synergistic combination is stearyl alcohol and myristyl alcohol. In one or more other embodiments the fatty alcohol synergistic combination is stearyl alcohol and cetyl alcohol. In one or more embodiments, the ratio of fatty alcohols can be optimized in order to obtain foams of good or excellent quality. In an embodiment the ratio between at least two fatty alcohols is about 1:1. In an embodiment the ratio between at least of two fatty alcohols is between about 11:5 and 5:11. In an embodiment the ratio between at least of two fatty alcohols is between about 1:1 and 5:11.

In one or more other embodiments the foaming booster consists essentially of at least one fatty alcohol or at least one fatty acid or a combination thereof combined with a polymeric agent. In one or more other embodiments the foaming booster consists essentially of at least two fatty alcohols. In one or more other embodiments the foaming booster consists essentially of at least two fatty acids.

Surprisingly, it appears that the foam quality can be influenced by the ratio of mixtures of two or more fatty alcohols, such as cetyl and stearyl alcohol.

Formulations having a cetyl:stearyl alcohol ratio of about 1:1 to about 5:11 generated, for example, a breakable foam of good to excellent quality being thermally stable on being applied to a surface at 36° C. having a collapse time of at least three minutes and having a low density. When the ratio of cetyl:stearyl alcohol was about 11:5 good quality foam was produced whereas, when the ratio about 1:1 to about 5:11 a foam of excellent quality was produced.

Thus, in one or more embodiments, there is provided a hydro-alcoholic foamable formulation of comprising about 11:5 to about 5:11 cetyl:stearyl alcohol of good to excellent quality being thermally stable having a collapse time of at least a minute or at least two minutes or at least three minutes. In one or more embodiments, there is provided a hydro-alcoholic foamable formulation of comprising about 11:5 to about 5:11 cetyl:stearyl alcohol which generates a quality foam of low density. In one or more embodiments, there is provided a hydro-alcoholic foamable formulation of good quality being thermally stable on being applied to a surface at 36° C. having a collapse time of at least three minutes comprising a ratio of about 11:5 cetyl:stearyl alcohol. In one or more embodiments, there is provided a hydro-alcoholic foamable formulation of excellent quality being thermally stable on being applied to a surface at 36° C. having a collapse time of at least three minutes comprising a ratio of about 1:1 to about 5:11 cetyl:stearyl alcohol.

The prior art hydroalcoholic foams are thermolabile and collapse quickly on exposure to human body temperature. Interestingly, it was unexpectedly discovered that surfactant contributed to the thermo-instability of hydroalcoholic foams. (Example 1 of U.S. Pat. No. 6,126,920)

It has further been discovered that removing the fatty alcohols from quick breaking foam formulation (Example 1 of U.S. Pat. No. 6,126,920) containing surfactants failed to produce a foam, whereas adding certain fatty alcohols (i.e. 3% cetostearyl alcohol) to this formulation improved foam quality. These results collectively shows the importance of excluding surface active agents and including suitable fatty alcohols into hydro-alcoholic foam formulations to produce quality breakable thermally stable foam. Thermally stable breakable foams of excellent quality were obtained in surfactant free formulations without humectants and without pH buffering agents. However, the presence of a fatty alcohol combined with a polymer booster was required as formulations with hydroxypropyl cellulose polymer but lacking cetostearyl alcohol failed to produce foam.

In one or more embodiments there is provided a hydro-alcoholic foam formulation lacking a surface active agent and comprising polymer and suitable fatty alcohols which produces quality breakable thermally stable foam. In one or more embodiments there is provided a surfactant free hydro-alcoholic foam formulation comprising polymer and suitable fatty acids which produce quality breakable thermally stable foam. In one or more embodiments there is provided a surfactant free hydro-alcoholic foam formulation comprising suitable fatty alcohols combined with fatty acids,which produce quality breakable thermally stable foam.

Furthermore, it was found that cellulose-based polymers (hydroxypropyl methylcellulose) have better foaming properties over pH sensitive expandable polymer like carbopol. In one or more embodiments there is provided a hydro-alcoholic foam formulation comprising cellulose-based polymers.

Furthermore, the formulations of the present invention can provide foams of excellent quality in the presence of various active ingredients. Extended accelerated stability of steroidal active ingredients, in hydro-alcoholic formulations of the present invention was demonstrated over a period of three and six months for betamethasone valerate and for a period of at least two months for mometasone furoate. Mometasone furoate was soluble and produced clear, quality, thermally stable formulations.

In one or more embodiments there is provided a surfactant free stable short term hydro-alcoholic foam formulation comprising at least one active ingredient. In one or more embodiments there is provided a surfactant free short term stable hydro-alcoholic foam formulation comprising at least one steroidal active ingredient. In one or more embodiments there is provided a surfactant free short terms stable hydro-alcoholic foam formulation comprising betamethasone valerate or mometasone furoate.

Formulations containing up to 60% ethanol provided thermally stable breakable foams of good to excellent quality. Also surprisingly the carrier without ethanol provided a good quality foam in the absence of surfactant. However, ethanol despite its defoaming and thermolabile properties, unexpectedly improved the foam quality and generated stable breakable foam contrary to that seen in the prior art. Foams of good quality were produced also using isopropanol.

In one or more embodiments, there is provided a foamable formulation or breakable foam of good quality having a low density and being thermally stable for more than one, or two or three minutes at 36° C. yet breakable upon shear force comprising up to 60% ethanol. In one or more embodiments, there is provided a foamable formulation or breakable foam of good quality comprising isopropanol. In one or more embodiments, there is provided a foamable formulation or breakable foam of good quality comprising a carrier without ethanol provided a good quality foam in the absence of surfactant.

In one or more embodiments, there is provided a foamable formulation comprising isopropanol that can generate a breakable foam of good quality having a low density and being thermally stable by having a collapse time of about or more than one, or two or three minutes at 36° C., and yet is breakable upon shear force.

Short Chain Alcohol

A short chain alcohol according to one or more certain other embodiments, has up to 6 carbon atoms in their carbon chain skeleton and one hydroxy group. Such short chain alcohols can be selected from ethanol, propanol, isopropanol, butanol, iso-butanol, t-butanol, pentanol and isomers thereof (herein after "a pentanol) and hexanol and isomers thereof (herein after "a hexanol). In a preferred embodiment the short chain alcohol is ethanol. The SCA is present in a substantial amount. By a substantial amount is meant that the alcohol is present at a % concentration by weight at which it is capable of having a defoaming effect and or an irritating effect. In various embodiments the amount of short chain alcohol is above about 10%. In one or more embodiments the alcohol is at least about 15% by weight. In other embodiments it is at least about 20%, at least about 25%, at least about 30%, at least about 35%, at least about 40%, at least about 45%, at least about 50%, at least about 55%, or at least about 60% by weight. In one or more embodiments the SCA is at a concentration between about 15% to about 65% by weight, or about 20% to about 60% by weight, preferably between about 25% to about 55% by weight, and more preferably between about 30% to about 50% by weight.

Fatty Alcohol

The hydro-alcoholic foamable composition foaming booster may include a fatty alcohol. The fatty alcohol which acts as a foam adjuvant is included in the foamable compositions as a main constituent, to evolve the foaming property of the composition and/or to stabilize the foam. In one or more embodiments, the fatty alcohol is selected from the group consisting of fatty alcohols having 15 or more carbons in their carbon chain, such as cetyl alcohol and stearyl alcohol (or mixtures thereof i.e. cetostearyl having 1 ratio). Other examples of fatty alcohols are myristyl alcohol (C14), arachidyl alcohol (C20), behenyl alcohol (C22), 1-triacontanol (C30), as well as alcohols with longer carbon chains (up to C50). In one or more preferred embodiments, the fatty alcohol is cetyl alcohol, stearyl alcohol, behenyl alcohol or myristyl alcohol and combinations thereof.

Fatty alcohols, derived from beeswax and including a mixture of alcohols, a majority of which has at least 20 carbon atoms in their carbon chain, are suitable as fatty alcohols in the context herein. In certain embodiments the amount of the fatty alcohol required to support the foam system can be approximately inversely related to the length of its carbon chains. Fatty alcohols are also useful in facilitating improved spreadability and absorption of the composition.

Fatty alcohols are amphiphatic, however unlike customary surfactants, they cannot usually function as stand-alone surfactants, because of their very weak emulsifying capacity. They are occasionally used as non-ionic co-emulsifiers, i.e., and are commonly used as thickeners (*Surfactants in personal care products and decorative cosmetics*, by Linda D. Rhein, Mitchell Schlossman, Anthony O'Lenick, P., Third Edition, 2006, p. 247). Fatty alcohols are generally regarded as safe and they are not considered as irritants.

An important property of the fatty alcohols used in context of the composition disclosed herein is related to their therapeutic properties per se. Long chain saturated and mono unsaturated fatty alcohols, e.g., stearyl alcohol, erucyl alcohol, arachidyl alcohol and behenyl alcohol (docosanol) have been reported to possess antiviral, antiinfective, antiproliferative and anti-inflammatory properties (see, U.S. Pat. No. 4,874,794). Longer chain fatty alcohols, e.g., tetracosanol, hexacosanol, heptacosanol, octacosanol, triacontanol, etc., are also known for their metabolism modifying properties and tissue energizing properties.

The concentration of a fatty alcohol or a combination of different fatty alcohols in the composition can in one or more embodiments range between about 0.1% and about 10% %, or between about 1% to about 15%. In certain embodiments, the concentration of the fatty acid can be selected from the group consisting of (i) between about 0.1% and about 1%, (ii) between about 1% and about 5%, and (iii) between about 5% and about 10%. In one or more embodiments, the fatty alcohol is at a concentration at about 1% to about 3% by weight.

Fatty Acid

The hydro-alcoholic foamable composition foaming booster may include a fatty acid or a combination of different fatty acids. In one or more embodiments the fatty acid can have 16 or more carbons in its carbon chain, such as myristic acid (C14), hexadecanoic acid (C16) stearic acid (C18), arachidic acid (C20), behenic acid (C22), octacosanoic acid (C28), as well as fatty acids with longer carbon chains (up to C50), or mixtures thereof.

Optionally, the carbon atom chain of the fatty acid may have at least one double bond; alternatively, the fatty acid can be a branched fatty acid. The carbon chain of the fatty acid also can be substituted with a hydroxyl group, such as 12-hydroxy stearic acid. In one or more preferred embodiments, the fatty acid is hexadecanoic acid, stearic acid or behenic acid or myristic acid (C14), or combinations thereof.

The fatty acid or combination of fatty acids according to one or more embodiments can be included in the foamable composition in a concentration of 0.1% to 5%. In one or more embodiments the concentration of the combination of fatty acids in the composition can be selected from the group consisting of (i) between about 0.1% by weight and about 1%, (ii) between about 1% by weight and about 5%, and (iii) between about 5% by weight and about 10%. In one or more embodiments a combination of myristylic acid and stearic acid is provided.

Fatty Acid Combined with Fatty Alcohol

In one or more embodiments, the hydro-alcoholic foamable composition foaming booster may include a combination at least one fatty acid with at least one fatty alcohol to provide a thermally stable breakable foam. In one or more embodiments a thermally stable breakable foam of excellent quality is obtained by combining stearyl alcohol with stearic acid.

Polymeric Agent (Polymer)

The hydro-alcoholic foamable composition foaming booster may include a polymeric agent. In one or more embodiments, the polymeric agent selected from the group consisting of a bioadhesive agent, a gelling agent, a film forming agent and a phase change agent. A polymeric agent enhances the creation of foam having fine bubble structure, which does not readily collapse upon release from the pressurized aerosol can. The polymeric agent serves to stabilize the foam composition and to control drug residence in the target organ. In certain embodiments the polymer can have surfactant like properties and contribute to the stabilization of emulsion formulations, such as poloxamer or pemulen (Acrylates/C10-30 alkyl acrylate crosspolymer).

Exemplary polymeric agents include, in a non-limiting manner, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, amine-bearing polymers such as chitosan; acidic polymers obtainable from natural sources, such as alginic acid and hyaluronic acid; chemically modified starches and the like, carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like.

Additional exemplary polymeric agents include semi-synthetic polymeric materials such as cellulose ethers, such as methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, and cationic celluloses, carbomer (homopolymer of acrylic acid is crosslinked with an allyl ether pentaerythritol, an allyl ether of sucrose, or an allyl ether of propylene, such as Carbopol® 934, Carbopol® 940, Carbopol® 941, Carbopol® 980 and Carbopol® 981. Poloxamers (synthetic block copolymer of ethylene oxide and propylene) such as Poloxamer 124, Poloxamer 188, Poloxamer 237, Poloxamer 338 and Poloxamer 407. Other useful Poloxamers are: 181, 182, 183, 184, 185, 212, 215, 217, 231, 234, 235, 238, 331, 333, 334, 335, 401, 402, and 403. Polyethylene glycol, having molecular weight of 1000 or more (e.g., PEG 1,000, PEG 4,000, PEG 6,000 and PEG 10,000) also have gelling capacity and they are also considered polymeric agents.

In one or more embodiments the polymeric agent, used in the composition is a cellulose-based polymer. In certain embodiments, it is selected from the group consisting of hydroxypropyl methylcellulose or hydroxypropyl cellulose.

Mixtures of the above polymeric agents are contemplated.

The concentration of the polymeric agent should be selected so that the composition, after filling into aerosol canisters and pressurized with propellant, is flowable, and can be shaken in the canister. In one or more embodiments, the concentration of the polymeric agent is selected such that the viscosity of the composition, prior to the filling of the composition into aerosol canisters, is less than 30,000 CP, and more preferably, less than 15,000 CP.

Combination of a Fatty Alcohol and/or a Fatty Acid and a Polymeric Agent

When a polymeric agent alone is used, a foam of good quality is not obtained. When, however, a polymeric agent is combined with a fatty alcohol or a fatty acid (or a mixture of a fatty alcohol and fatty acid) these two components can, surprisingly, act to produce a good quality foam.

In one or more embodiments the range of ratio of fatty acid and or fatty alcohol to polymer can be about 100:1 to about 1:50; or about 90:1 to about 1:45; or about 80:1 to about 1:40; or about 70:1 to about 1:35; or about 60:1 to about 1:30; or about 50:1 to about 1:25; or about 40:1 to about 1:20; or about 30:1 to about 1:15; or about 20:1 to about 1:10; or about 15:1 to about 1:5; or about 10:1 to about 1:1; or any ranges in between such as 1:20 to 20:1,or preferably from 1:10 to 10:1

Propellant

The composition requires the addition of a propellant in order to generate a foam.

Suitable propellants include volatile hydrocarbons such as butane, propane, isobutene or mixtures thereof. In one or more embodiments a hydrocarbon mixture AP-70 is used. In one or more other embodiments a lower pressure hydrocarbon mixture AP-46 is used. Both contain butane, propane, isobutene although in different proportions. AP-46 is composed of about 16% w/w of propane, about 82% w/w of isobutane and about 2% w/w of propane. AP-70 is composed of about 50% w/w of propane, about 20% w/w of isobutane and about 30% w/w of propane. Hydrofluorocarbon (HFC) propellants are also suitable as propellants in the context disclosed herein. Exemplary HFC propellants include 1,1,1,2 tetrafluorethane (Dymel 134), and 1,1,1,2,3,3,3 heptafluoropropane (Dymel 227). Dimethyl ether is also useful. In one or more embodiments use of compressed gases (e.g., air, carbon dioxide, nitrous oxide, and nitrogen) is also possible.

In one or more embodiments a combination of at least two propellants, selected from HFC, hydrocarbon propellants, dimethyl ether and compressed gases is contemplated.

Any concentration of the propellant, which affords an acceptable foam is useful in accordance with the present invention. In certain embodiments the propellant makes up between about 3% and about 25% by weight of the foamable composition, or between about 20% by weight and about 30%, or between about 20% by weight and about 35% by weight and preferably between about 5% by weight and about 16% by weight of the composition. In preparing the formulations the ingredients other than propellant are combined to 100% and the propellant is added thereafter so that the ratio of formulation to propellant can range from 100:3 to 100:35, 100:3 to 100:30, 100:3 to 100:25 or preferably 100:5 to 100:16.

In one or more embodiments the propellant can also be used to expel formulation using a bag in can system or a can in can system as will be appreciated by someone skilled in the art. In certain embodiments the part of the propellant system is in the formulation and part separate from the formulation. In this way it is possible to reduce the amount of propellant in the formulation but still provide good expulsion from the canister, where the foamable formulation is expelled quickly but without jetting or noise. In one or more embodiments such system is used to expel foam into a body cavity where the amount of propellant released into the cavity is minimized.

Without being bound to any theory, it can be supposed that in certain embodiments in the absence of an independent oil phase, hydrocarbon propellant is partially solubilized by the SCA and the fatty alcohols and or fatty acids present in the composition, thus providing a clear composition. It was noted from a visual impaction that the fatty acids and alcohols were dissolved in the composition.

Suspensions

In one or more embodiments the active or cosmetic ingredient is completely soluble in the formulation or a phase thereof. In certain other embodiments it is provided as a suspension. For example, benzyl peroxide ('BPO') or microsponges comprising an active ingredient such as retinoic acid or other encapsulated bodies, such as described herein. The following description applied to BPO will also apply with the necessary changes to other solid agents, microspheres and other bodies. As can be appreciated, forming a homogeneous suspension of a BPO or other solid particle or body in foamable formulation using a formulation with high viscosity—so that even after addition of propellant the formulation has a high viscosity—in order to try and stabilize the oil droplets and BPO particles, minimize particle motion and discourage gravitational sedimentation in the canister in which the formulation is stored simply will not do for foamable compositions. Such viscous formulations are not desirable for foamable compositions since they have low flowability and may exhibit one or more of the following: are not shakable; form a block, i.e., a solid with no flowable mass, in the canister; do not result in uniform expulsion; and if expulsed may be accompanied by unwanted phenomena such as one or more of jets, tailing and noise.

Unexpectedly it has been discovered that it is possible to make compositions which are truly flowable and have low viscosity in which the propellant forms part of the oil phase of the emulsion formulation but nevertheless surprisingly does not make the formulation substantially vulnerable to phase separation and or sedimentation. Moreover these compositions are stable and are able to form breakable foam of quality that spreads easily and is able to deliver an effective and measurable amount of active agent homogeneously to a target surface.

One key element is the polymeric agent used in the formulation. The polymeric agent can contribute to the stability and stabilization of the formulation. Concentrations of polymeric agents and other thickeners have in the past been used to achieve very high viscosities of at least 20,000 centipoises (cps) to a million or more cps. Surprisingly by using a polymer in concentrations and conditions, which results in lower viscosities, for example, of the order of about 7000 to about 8000 cps or less for the pre-foam formulation whose viscosity is further reduced upon inclusion of propellant, it is possible to achieve, for example, a stable BPO formulation that produces breakable (non thermolabile) foam of good quality even after addition of propellant and even though the foamable formulation with propellant is fluid and easily shakable. In a preferred embodiment the viscosity of a formulation comprising propellant is below about 5000 cps and in a more preferred embodiment it is below about 3000 cps. At such low levels of viscosity, one would expect a suspended solid active agent such as BPO to precipitate out of solution. In the low viscosity formulations provided herein, BPO should remain homogeneously dispersed in suspension. For pharmaceutical applications, BPO needs to be homogeneous to ensure that the amount of BPO in the first dose and the last dose is sufficiently uniform. Without being bound to any theory it is anticipateded that in order to form a homogenous suspension of BPO a carbomer would be included at a pH which at which its expansion is reduced.

An important factor in the use of a polymeric agent is to ensure the polymer(s) is appropriately and correctly swelled in the presence of water by adding an effective amount of base. Without being bound by any theory it may be the case that the lower levels of polymeric agent still form a semi water gel like infrastructure that unexpectedly is able to stabilize the BPO physically and chemically at low viscosities.

In an embodiment the polymer is an amphiphilic polymer, such as, an acrylates/C10-30 alkyl acrylate crosspolymer. The hydrophilic and hydrophobic regions of these polymers serve to interact with and stabilize hydrophilic and lipophilic components, respectively, of a composition. In one embodiment the polymeric agent is a carbomer.

By way of example, suitable amphiphilic polymers include cross linked copolymers of acrylic acid and a hydrophobic comonomer, such as Pemulen TR-1 and Pemulen TR-2 (Acrylates/C10-30 alkyl acrylate crosspolymer), ETD 2020 and Carbopol 1382 (all, Acrylates/C10-30 alkyl acrylate crosspolymer), Natrosol CS Plus 330 and 430 and Polysurf 67 (all, cetyl hydroxyethyl cellulose), Aculyn 22 (acrylates/steareth-20 methacrylate copolymer), Aculyn 25 (acrylates/laureth-25 methacrylate copolymer), Aculyn 28 (acrylates/beheneth-25 methacrylate copolymer), Aculyn 46 (PEG-150/stearyl alcohol/SMDI copolymer), Stabylen 30 (acrylates/vinyl isodecanoate), Structure 2001 (acrylates/steareth-20 itaconate copolymer), Structure 3001 (acrylates/ceteth-20 itaconate copolymer) and Structure Plus (acrylates/aminoacrylates/C10-30 alkyl PEG 20 itaconate copolymer), where PEG is polyethylene glycol, PPG is polypropylene glycol.

Other exemplary amphiphilic copolymers include silicone polymers such as amphiphilic silicone polyols or copolyol, for example cetyl dimethicon copolyol and dimethicone copolyol PPG-3 oleyl ether, acetylated starch derivatives, amphiphilic modified starches, and amphiphilic block copolymers of ethylene oxide, propylene oxide and/or propylene glycol (also known as "poloxamer").

The gelling agent may include other types of gelling agents, in combination with an amphiphilic copolymer. A non limiting list of other types such as water soluble cellulose, or gums like guar and xantham is provided below.

A further element and aid to reducing viscosity in the presence of gelling agents is the use of a buffer or buffer complex, such as citrate buffer or alternatively lactate to cause a thick emulsion gel or paste containing carbomer to become fluid. Other similar buffers may work. Non limiting examples of appropriate possible buffers, which may achieve the same objective are acetate, malate, sorbate, succinate and tartrate.

Optional Ingredients

Optionally, the foamable composition further includes at least one organic carrier selected from the group consisting of a polar solvent, a hydrophobic organic carrier and mixtures thereof, at a concentration of about 2% to about 50% by weight.

Hydrophilic Solvent

A hydrophilic solvent is a solvent that is more miscible with water than with a hydrophobic compound.

Examples of suitable hydrophilic solvents are water, propylene glycol, low molecular weight polyethylene glycols, methoxyisopropanol, PPG-2 propyl ether, PPG-2 butyl ether, PPG-2 methyl ether, PPG-3 methyl ether, dipropylene glycol propyl ether, dipropylene glycol butyl ether, dipropylene glycol, methyl propanediol, propylene carbonate, water soluble/dispersible polypropylene glycols, ethoxylated polypropylene glycol, glycerin, sorbitol, hydrogenated starch hydrolysate, silicone glycols, and their mixtures and the like. In one or more embodiments water is a hydrophilic solvent.

In one or more embodiments, the composition comprises a hydrophilic solvent.

In one or more embodiments, the short chain alcohol is replaced by is a hydrophilic solvent.

In one or more embodiments, the hydrophilic solvent is a polyol. A polyol is an organic substance that contains at least two hydroxy groups in its molecular structure. In one or more embodiments, the foamable carrier contains at least one diol In one or more embodiments, the foamable carrier contains at least one triol. In one or more embodiments, the polyol is a mixture of polyols. In one or more embodiments, the mixture of polyols contains at least one diol and at least one triol. In one or more embodiments the hydrophilic solvent is a polar solvent.

In one or more embodiments, the hydrophilic solvent is selected from the group consisting of propylene glycol, low molecular weight polyethylene glycols and glycerin.

Polar Solvent

A "polar solvent" is an organic solvent which is typically soluble in both water and oil.

In one or more embodiments, the polar solvent is a polyol. Polyols are organic substances that contain at least two hydroxy groups in their molecular structure.

In one or more embodiments, the polar solvent contains a diol (a compound that contains two hydroxy groups in its molecular structure), such as propylene glycol (e.g., 1,2-propylene glycol and 1,3-propylene glycol), butanediol (e.g., 1,4-butaneediol), butanediol (e.g., 1,3-butaneediol and 1,4-butenediol), butynediol, pentanediol (e.g., 1,5-pentanediol), hexanediol (e.g., 1,6-hexanediol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the polar solvent contains a triol (a compound that contains three hydroxy groups in its molecular structure), such as glycerin and 1,2,6-Hexanetriol.

Additional examples of polar solvents include polyols, such as glycerol (glycerin), propylene glycol, hexylene glycol, diethylene glycol, propylene glycol n-alkanols, terpenes, di-terpenes, tri-terpenes, terpen-ols, limonene, terpene-ol, 1-menthol, dioxolane, ethylene glycol, other glycols, alkanols, such as dialkylamino acetates, and admixtures thereof, dimethyl isosorbide, ethyl proxitol, dimethylacetamide (DMAc) and alpha hydroxy acids, such as lactic acid and glycolic acid.

According to still other embodiments, the polar solvent is a polyethylene glycol (PEG) or PEG derivative that is liquid at ambient temperature, including PEG200 (MW (molecular weight) about 190-210 kD), PEG300 (MW about 285-315 kD), PEG400 (MW about 380-420 kD), PEG600 (MW about 570-630 kD) and higher MW PEGs such as PEG 4000, PEG 6000 and PEG 10000 and mixtures thereof.

Yet, in additional embodiments, the polar solvent is an aprotic polar solvent, such as dimethyl sulfoxide (DMSO), dimethylformamide (DMF), acetonitrile, acetone, methyl ethyl ketone, 1,4-Dioxane and tetrahydrofuran (THF). Additional non-limiting examples include N-methylpyrrolidone, pyridine, piperidine, dimethyl ether, hexamethylphosphorotriamide, dimethylformanide, methyl dodecyl sulfoxide, N-methyl-2-pyrrolidone and 1-methyl-2-pyrrolidinone) and azone (1-dodecylazacycloheptan-2-one).

Many polar solvents, for example propylene glycol, glycerin, DMSO and azone possess the beneficial property of a dermal, transdermal or trans-mucosal drug delivery enhancer.

In one or more embodiments, the polar solvent is a dermal, transdermal or trans-mucosal drug delivery enhancer.

Many polar solvents, for example propylene glycol and glycerin, possess the beneficial property of a humectants.

In one or more embodiments, the polar solvent is a humectant.

Hydrophobic Solvent/Emollient

One or more hydrophobic solvents are optionally included in the composition, in order to add to the sensory properties of the composition and/or in order to impart skin conditioning properties. In an embodiment, the hydrophobic solvent is an emollient, i.e., a substance that softens and soothes the skin. Emollients are used to correct dryness and scaling of the skin. The hydrophobic solvent and/or the emollient can be selected from the group consisting of mineral oil, alkyl esters of fatty acids such as isopropyl palmitate, isopropyl isostearate, diisopropyl adipate, diisopropyl dimerate, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, maleated soybean oil, unsaturated or polyunsaturated oils, such as olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils; essential oils; and silicone oils, such as dimethicone, cyclomethicone, polyalkyl siloxane, polyaryl siloxane, polyalkylaryl siloxane, a polyether siloxane copolymer and a poly(dimethylsiloxane)-(diphenyl-siloxane) copolymer. In certain embodiments the carrier can comprise a petrolatum where it is provided in modest or minor amounts of up to about 5%.

In one or more preferred embodiments the hydrophobic solvent has at least a degree of solubility in the SCA present in the formulation.

In order to improve the miscibility or the dispersion of a hydrophobic solvent in the formulation, fatty alcohols and preferably fatty acids can be added in order to form an emulsion which is either stable or easily re-dispersible by shaking. In certain embodiments effective amounts of polymeric agents may be added. By re-dispersible on shaking is meant that the formulation on reasonable moderate shaking of about a few times will provide a uniform emulsion which will remain relatively stable for at least a reasonable short period of time sufficient to allow it to be dispensed from the pressurized canister. In one or more embodiments a combination of one or more fatty acids with one or more fatty alcohols is used to help provide an emulsion which has at least a short term stability and is easily re-dispersible on shaking.

Modulating Agent

In one or more embodiments the formulation includes a modulating agent. The term modulating agent is used to describe an agent which can improve the stability of or stabilize a foamable carrier or composition and or an active agent by modulating the effect of a substance or residue present in the carrier or composition.

In one or more embodiments the substance or residue may for example be acidic, basic or a buffer agent, which can affect pH in a composition. The agent can be any of the known buffering systems used in pharmaceutical or cosmetic formulations as would be appreciated by a man of the art. It can also be an organic acid, a carboxylic acid, a fatty acid an amino acid, an aromatic acid, an alpha or beta hydroxyl acid an organic base or a nitrogen containing compound. In certain embodiments the modulating agent is a buffer, as defined by Van Slyke [Van Slyke, J. Biol. Chem. 52, 525 (1922)], as "a substance which by its presence in solution increases the amount of acid or alkali that must be added to cause unit change in pH."

Certain active agents are known to be stable at a narrow pH range. For example, corticosteroids are typically stable at acidic pH levels, while vitamin D3 derivatives are stable at basic pH. Hence, in certain embodiments the modulating agent is selected to exert a pH modifying effect, which results in the desirable pH level.

In certain embodiments, the pH modifying agent is selected from the group including citric acid and sodium citrate.

It is important to maintain skin surface pH in order to prevent susceptibility to bacterial skin infections or skin damage and disease. Thus, adding a modulating agent, which contributes to the stabilization of skin pH at the desirable level, is advantageous.

In the same fashion, adding an acidic modulating agent to a foamable composition, which is intended for vaginal application is advantageous, since better protection against vaginal infection is attained with pH lower than about 4.5.

In an embodiment, the modulating agent is an antioxidant or a radical scavenger. Non-limiting examples of antioxidants/radical scavengers are ascorbic acid and derivatives, tocopherol or derivatives thereof (succinate, or sorbate or acetate or other esters), propyl galate, butylated hydroxy toluene and butyl hydroxy anisol. Non-limiting examples of positive ionization agents are benzyl conium chloride, and cetyl pyridium chloride. Non-limiting examples of negative ionization agents are sodium lauryl sulfate, sodium lauryl lactylate and phospholipids.

In one or more further embodiments the modulating agent is a chelating or sequestering or complexing agent that is sufficiently soluble or functional in the solvent to enable it to "mop up" or "lock" metal ions. In one or more embodiments a preferred non limiting example is EDTA.

Modulating agents may be added to the compositions of the subject invention, as necessary to provide their function of improving the stability of or stabilize a foamable carrier or composition and or an active agent. The modulating agent concentration can preferably range from about 0.1% to about 10%, more preferably from about 1% to about 5%, of the composition. In certain cases the active agent itself is the modulating agent, alone or in combination with another modulating agent, and in such cases it will be added at an effective dose which may be outside these ranges. For example azelaic acid may be at about 15% of the composition.

Additional Components

In an embodiment, a composition disclosed herein includes one or more additional components. Such additional components include but are not limited to anti perspirants, anti-static agents, bulking agents, cleansers, colorants, skin conditioners, deodorants, diluents, dyes, fragrances, hair conditioners, herbal extracts, humectants, keratolytic agents, pearlescent aids, perfuming agents, pH preservatives, protectants, skin penetration or permeation enhancers, softeners, solubilizers, sunscreens, sun blocking agents, sunless tanning agents, viscosity modifiers, flavanoids and vitamins. As is known to one skilled in the art, in some instances a specific additional component may have more than one activity, function or effect.

In one or more further embodiments the composition further includes about 0.1% to about 5% of a humectant. In one or more further embodiments the humectant is selected from the group consisting of PEG 400, propylene glycol and glycerin or mixtures of two or more thereof Substantially Surfactant Free According to one or more embodiments, the foamable composition is substantially surfactant-free. In the context herein, the term "substantially surfactant free composition" relates to a composition that contains a total of less than about 0.4% of a surfactant selected from the group consisting of non-ionic, anionic, cationic, zwitterionic, amphoteric and ampholytic surfactants. Preferably, the composition comprises less than about 0.2% by weight of a surfactant and more preferably less than about 0.1%. Non-surfactant compositions will comprise no or negligible levels of surface active agents (essentially surfactant free).

In the art, the term surface active agent or surfactant is sometimes used loosely and some publications may refer to compounds that have a supportive role, such as co-surfactants as surfactants. Substances which cannot function as true surfactants on their own but only in the context of being used with another surfactant are not considered to be surfactants for the purposes described herein. Thus, in the context herein, a fatty alcohol is not regarded a surfactant, and likewise, a fatty acid is not regarded as a surfactant In contrast, however, an ether or an ester formed from them can be a surfactant. Also quaternary ammonium compounds and ions, which for example are not infrequently seen in hair preparations, are not regarded as surfactants.

Physical Characteristics of the Foamable Composition and Foam

A foamable composition manufactured according to one or more embodiments herein is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

In one or more embodiments the foamable composition is a single phase solution. In certain circumstances, the active agent is insoluble and is presented as a homogeneous suspension and the formulation is turbid or cloudy. In one or more other embodiments the formulation prior to addition of propellant is an emulsion. In one or more embodiments the foam composition has an acceptable shelf-life of at least one year, or at least two years at ambient temperature. A feature of a product for cosmetic or medical use is long term stability. Propellants, which are a mixture of low molecular weight hydrocarbons, tend to impair the stability. The foamable compositions herein are surprisingly stable, even in the absence of customary surfactants.

Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam. Compositions containing a substantial amount of semi-solid hydrophobic solvents, e.g., white petrolatum, as the main ingredients of the oil phase of the emulsion, will likely exhibit high viscosity and poor flowability and are inappropriate candidates for a foamable composition.

Foam Quality

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of a more stable foam, which does not collapse spontaneously immediately upon discharge from the container. The finer foam structure looks and feels smoother, thus increasing its usability and appeal.

Foam Density

Another property of the foam is specific gravity or density, as measured upon release from the aerosol can. Typically, foams have specific gravity of less than 0.20 g/mL or less than 0.12 g/mL, depending on their composition and on the propellant concentration.

Shakability

'Shakability' means that the composition contains some or sufficient flow to allow the composition to be mixed or remixed on shaking. That is, it has fluid or semi fluid properties. Shakability is described further in the section on Tests. In one or more certain limited embodiments the formulation is poorly shakable but is nevertheless flowable.

Breakability/Collapse Time

A further aspect of the foam is breakability. The balance between stability and breakability of the foam coming out of the container is very delicate: on one hand the foam should preferably not be "quick breaking", i.e., it should be stable upon release from the pressurized container and not break as a result of exposure to skin temperature; and on the other hand, it should be "breakable", i.e., it should spread easily, break down and absorb into the skin or membrane upon application of mild shear force. The breakable foam is thermally stable, yet breaks under shear force. Shear-force breakability of the foam is clearly advantageous over thermally-induced breakability. Thermally sensitive foams start to collapse immediately upon exposure to skin temperature and, therefore, cannot be applied on the hand and afterwards delivered to the afflicted area.

The collapse time of foam represents its tendency to be temperature-sensitive and its ability to be at least stable in the short term so as to allow a user sufficient time to comfortably handle and apply the foam to a target area without being rushed and or concerned that it may rapidly collapse, liquefy and or disappear. Collapse time, as an indicator of thermal sensitivity, is examined by dispensing a given quantity of foam and photographing sequentially its appearance with time during incubation at 36° C.

Short chain alcohols are known to cause foam to be thermolabile and "quick breaking." However, in certain embodiments herein, despite the presence of high alcohol content, quite unexpectedly the foam is substantially thermally stable. By "substantially thermally stable" it is meant that the foam upon application onto a warm skin or body surface at about 35-37° C. does not collapse within about 30 seconds. Thus, in one or more embodiments the simple collapse time of the foam is more than about 30 seconds or more than about one minute or more than about two minutes. In one or more limited embodiments simple collapse time can be a little shorter than 30 seconds, but not less than about 20 seconds. In one or further or alternative embodiments the collapse time is measured by introducing a sample of foam into an incubator at 36° C. and the collapse time of the foam is more than 30 seconds or more than about one minute or more than about two minutes.

Pharmaceutical Composition

The foamable composition is an ideal vehicle for active pharmaceutical ingredients and active cosmetic ingredients. In the context active pharmaceutical ingredients and active cosmetic ingredients are collectively termed "active agent" or "active agents". In one or more embodiments the active agent is soluble in the composition of a phase thereof. In one or more other embodiments it is insoluble. When insoluble the active agent is presented as a suspension or on a carrier which can include microspheres and the like.

Suitable active agents include but are not limited to an active herbal extract, an acaricides, an age spot and keratose removing agent, an allergen, an alpha hydroxyl acid, an analgesic agent, an antiacne agent, an antiallergic agent, an antiaging agent, an antibacterial agent, an antibiotic, an antiburn agent, an anticancer agent, an antidandruff agent, an antidepressant, an antidermatitis agent, an antiedemic anent, an antifungal agent, an antihistamine, an antihelminth agent, an antihyperkeratolyte agent, an anti-infective agent, an antiinflammatory agent, an antiirritant, an antilipemic agent, an antimicrobial agent, an antimycotic agent, an antioxidant, an antiparasitic agent, an antiproliferative agent, an antipruritic agent, an antipsoriatic agent, an antirosacea agent, an antiseborrheic agent, an antiseptic agent, an antiswelling agent, an antiviral agent, an anti-wart agent, an anti-wrinkle agent, an antiyeast agents, an astringent, a beta-hydroxy acid, benzoyl peroxide, a topical cardiovascular agent, a chemotherapeutic agent, a corticosteroid, an immunogenic substance, a dicarboxylic acid, a disinfectant, a fungicide, a hair growth regulator, a haptene, a hormone, a hydroxy acid, an immunosuppressant, an immunoregulating agent, an immunomodulator, an insecticide, an insect repellent, a keratolytic agent, a lactam, a local anesthetic agent, a lubricating agent, a masking agent, a metal, a metal oxide, a mitocide, a neuropeptide, a non-steroidal anti-inflammatory agent, an oxidizing agent, a pediculicide, a peptide, a protein, a photodynamic therapy agent, a radical scavenger, a refatting agent, a retinoid, a sanative, a scabicide, a self tanning agent, a skin protective agent, a skin whitening agent, a steroid, a steroid hormone, a vasoconstrictor, a vasodilator, a vitamin, a vitamin A, a vitamin A derivative, a vitamin B, a vitamin B derivative, a vitamin C, a vitamin C derivative, a vitamin D, a vitamin D derivative, a vitamin D analog, a vitamin F, a vitamin F derivative, a vitamin K, a vitamin K derivative, a wound healing agent and a wart remover. As is known to one skilled in the art, in some instances a specific active agent may have more than one activity, function or effect.

Encapsulation of an Active Agent

In one or more embodiments, the active agent is encapsulated in particles, microparticles, nanoparticles, microcapsules, microspheres, nanocapsules, nanospheres, liposomes, niosomes, polymer matrix, silica-gel, graphite, nanocrystals or microsponges. Such particles can have various functions, such as (1) protection of the drug from degradation; (2) modification of the drug release rate from the composition; (3) control of skin penetration profile; and (4) mitigation of adverse effects, due to the controlled release of the active agent from the encapsulation particles.

Solubility of an Active Agent

In an embodiment, the active agent is not fully soluble in water or, is not fully soluble in the SCA, is not fully soluble in the presence of a hydrophobic solvent in the formulation, or is not fully soluble in the oil phase of the emulsion. In one or more embodiments the active agent is soluble in the composition or a phase thereof. In an embodiment, the aprotic polar solvent is present in the composition in an amount sufficient to solubilize the active agent in the composition. In one or more embodiments, aprotic polar solvent acts to improve the solubility of an active agent. In certain preferred embodiments, the active agent to be solubilized is selected from the group consisting of a non-steroidal anti-inflammatory agent, a local anesthetic agent, a steroid, an immunomodulator, a keratolytically active agent, an anti-acne agent, an anti-rosacea agent, an antiinfective agent and an anti-psoriasis agent. In a preferred embodiment the active agent to be solubilized is diclofenac.

Exemplary Groups of Active Agents

Steroids

In an embodiment, the active agent is a steroid. In certain embodiments the steroid is a corticosteroid, including but not limited to, hydrocortisone, hydroxyltriamcinolone, alpha-methyl dexamethasone, dexamethasone-phosphate, beclomethsone dipropionate, clobetasol valemate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone valerate and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortmate, mepreddisone, paramethasone, prednisolone, prednisone, beclomethasone dipropionate, triamcinolone, as well as analogs, derivatives, salts, ions and complexes thereof.

In certain embodiments, the steroid is a hormone or a vitamin, as exemplified by pregnane, cholestane, ergostane, aldosterone, androsterone, calcidiol, calciol, calcitriol, calcipotriol, clomegestone, cholesterol, corticosterone, cortisol, cortisone, dihydrotestosterone, ergosterol, estradiol, estriol, estrone, ethinylestradiol, fusidic acid, glucocorticoid, lanosterol, mometasone furoate, prednisolone, prednisone, progesterone, spironolactone, timobesone and testosterone, as well as analogs, derivatives, salts, ions and complexes thereof.

In an embodiment, the aprotic polar solvent is present in the composition in an amount sufficient to solubilize the steroid.

NSAID

In an embodiment, the active agent is a non-steroidal anti-inflammatory agent. In the context a nonsteroidal anti-inflammatory agent (also termed herein "NSAID") is a pharmaceutically active compound, other than a corticosteroid, which affects the immune system in a fashion that results in a reduction, inhibition, prevention, amelioration or prevention of an inflammatory process and/or the symptoms of inflammation and or the production pro-inflammatory cytokines and other pro-inflammatory mediators, thereby treating or preventing a disease that involves inflammation.

In one or more embodiments, the NSAID is an inhibitor of the cyclooxygenase (COX) enzyme. Two forms of cyclooxygenase are known today: the constitutive cyclooxygenase (COX-1); and the inducible cyclooxygenase (COX-2), which is pro-inflammatory. Thus, in one or more embodiments, the NSAID is selected from the group consisting of a COX-1 inhibitor, a COX-2 inhibitor or a non-selective NSAID, which simultaneously inhibits both COX-1 and COX-2.

In one or more embodiments, the NSAID is salicylic acid a salicylic acid derivatives. Exemplary salicylic acid derivative include, in a non limiting fashion, aspirin, sodium salicylate, choline magnesium trislicylate, salsalate, diflunisal, salicylsalicylic acid, sulfasalazine, olsalazine, esters of salicylic acid with a carboxylic acid, esters of salicylic acid with a dicarboxylic acid, esters of salicylic acid with a fatty acid, esters of salicylic acid with a hydroxyl fatty acid, esters of salicylic acid with an essential fatty acid, esters of salicylic acid with a polycarboxylic acid, and any compound wherein salicylic acid is linked to an organic moiety through a covalent bond.

In one or more embodiments, the NSAID is para-aminophenol (e.g., acetaminophen) and salts and derivatives thereof.

In one or more embodiments, the NSAID is an indole or an indole—acetic acid derivative (e.g., indomethacin, sulindac, etodolac) and salts and derivatives thereof.

In one or more embodiments, the NSAID is an aryl acetic acids (e.g., tolmetin, diclofenac, ketorolac) and salts and derivatives thereof.

In one or more embodiments, the NSAID is an arylpropionic acid and salts and derivatives thereof. Exemplary arylpropionic acid derivative include, in a non limiting fashion, are ibuprofen, naproxen, flubiprofen, ketoprofen, fenoprofen, oxaprozin.

In one or more embodiments, the NSAID is anthranilic acids or an anthranilic acid derivative, also termed "fenamates" (e.g., mefenamic acid, meclofenamic acid) and salts and derivatives thereof.

In one or more embodiments, the NSAID is selected from the group of enolic acids, enolic acid salts, enolic acid esters, amides, anhydrides and salts and derivatives thereof. Non-limiting examples of enolic acid derivatives include oxicams (piroxicam, tenoxicam) and pyrazolidinediones (phenylbutazone, oxyphenthratrazone)

Yet, in additional embodiments, the NSAID is an alkanone (e.g., nabumetone).

Selective COX-2 Inhibitors include, in an exemplary manner diaryl-substituted furanones (e.g., Rofecoxib); diaryl-substituted pyrazoles (e.g., Celecoxib); indole acetic acids (e.g., Etodolac); and sulfonanilides (e.g., Nimesulide) and salts and derivatives thereof.

In an embodiment, the aprotic polar solvent is present in the composition in an amount sufficient to solubilize the NSAID, as exemplified herein by the solubilization of diclofenac.

Local Anesthetic Agents

In an embodiment, the active agent is a local anesthetic agent. Without limiting the scope, the anesthetic agent can be selected from the group consisting of benzocaine, lidocaine, bupivacaine, chlorprocaine, dibucaine, etidocaine, mepivacaine, tetracaine, dyclonine, hexylcaine, procaine, cocaine, ketamine, pramoxine, phenol, any pharmaceutically acceptable salts thereof and mixtures of such anesthetic agents. Any mixture of synergistically beneficial anesthetic agents is contemplated. In an embodiment, the aprotic polar solvent is present in the composition in an amount sufficient to solubilize the anesthetic agent.

Keratolytically Active Agents

A keratolytic agent may be included as an active agent of a foamable composition. The term "keratolytically active agent" as used herein includes a compound that loosens and removes the stratum corneum of the skin, or alters the structure of the keratin layers of skin. Keratolytically active agents are used in the treatment of dermatological disorders that involve dry skin, hyperkeratinization (such as psoriasis), skin itching (such as xerosis), acne and rosacea.

Suitable keratolytically active agents include phenol and substituted phenolic compounds. Such compounds are known to dissolve and loosen the intracellular matrix of the hyperkeratinized tissue. As such, they are used in the treatment of dermatological disorders. Dihydroxybenzene and derivatives thereof have been recognized as potent keratolytic agents. Resorcinol (m-dihydroxybenzene) and derivatives thereof are used in anti-acne preparations. In addition to hydroquinone (p-dihydroxybenzene) having anti-pigmentation properties, hydroquinone is also known to be keratolytic. These compounds also exhibit antiseptic properties. Cresols also possess bactericidal and keratolytic properties.

Vitamin A and vitamin A derivatives, also termed herein "retinoids", such as retinoic acid, isoretinoic acid, retinol and retinal, as well as adapalene, tazarotene, isotretinoin, acitretin and additional retinoids known in the art of pharmaceuticals and cosmetics are another class of keratolytically active agents.

Another group of keratolytically active agents include alpha-hydroxy acids, such as lactic acid and glycolic acid and their respective salts and derivatives; and beta-hydroxy acids, such as salicylic acid (o-hydroxybenzoic acid) and salicylic acid salts and pharmaceutically acceptable derivatives.

Another class of keratolytically active agents includes urea and urea derivatives.

Immunomodulators

In an embodiment, the active agent is an immunomodulator Immunomodulators are chemically or biologically-derived agents that modify the immune response or the functioning of the immune system Immunomodulators suitable for use according to the present invention include, among other options, cyclic peptides, such as cyclosporine, tacrolimus, tresperimus, pimecrolimus, sirolimus, verolimus, laflunimus, laquinimod and imiquimod, as well as analogs, derivatives, salts, ions and complexes thereof. Such compounds, delivered in the foam, are especially advantageous in skin disorders such as psoriasis, eczema and atopic dermatitis, where the large skin areas are to be treated. In an embodiment, the aprotic polar solvent is present in the composition in an amount sufficient to solubilize the immunomodulator.

Retinoids

In an embodiment, the active agent is a retinoid. Retinoids suitable for use according to the present invention include, among other options, retinol, retinal, retinoic acid, isotretinoin, tazarotene, adapalene, 13-cis-retinoic acid, acitretin all-trans beta carotene, alpha carotene, lycopene, 9-cis-beta-carotene, lutein and zeaxanthin, as well as any additional retinoids known in the art of pharmaceuticals and cosmetics; and analogs, derivatives, salts, ions and complexes thereof.

Anti-Acne and Anti-Rosacea Active Agents

In embodiment, the active agent is an anti-acne or an anti-rosacea agent. The anti-acne agent can be selected from the group consisting of resorcinol, sulfur, salicylic acid and salicylates, alpha-hydroxy acids, nonsteroidal anti-inflammatory agents, benzoyl peroxide, retinoic acid, isoretinoic acid and other retinoid compounds, adapalene, tazarotene, azelaic acid and azelaic acid derivatives, antibiotic agents, such as erythromycin and clyndamycin, coal tar, zinc salts and complexes, and combinations thereof, in a therapeutically effective concentration.

Antipsoriasis Agents

In an embodiment, the active agent is an anti-psoriasis agent. Such anti-psoriasis agents can be selected, among other options, from the group of keratolytically-active agents, salicylic acid, coal tar, anthralin, corticosteroids, vitamin D and derivatives and analogs thereof, including vitamin D3 analogs such as calcitriol, calcipotriol; retinoids, and photodymamic therapy agents.

Antiinfective Agents

In an embodiment, the active agent is an anti-infective agent. Such anti-infective agent can be selected from the group of an antibiotic agent, an antibacterial agent, an antifungal agent, an agent that controls yeast, an antiviral agent and an antiparasitic agent. Exemplary antiinfective agents are exemplified by beta-lactam antibiotic, an aminoglycoside, an ansa-type antibiotic, an anthraquinone, an azole, metronidazole, an antibiotic glycopeptide, a macrolide, erythromycin, clindamycin, an antibiotic nucleoside, an antibiotic peptide, polymyxin B, an antibiotic polyene, an antibiotic polyether, an antibiotic quinolone, an antibiotic steroid, fucidic acid, mupirocin, chloramphenicol, a sulfonamide, tetracycline, an antibiotic metal, silver, copper, zinc, mercury, tin, lead, bismuth, cadmium, chromium, an oxidizing agent, iodine, iodate, a periodate, a hypochlorite, a permanganate, a substance that release free radicals and/or active oxygen, a cationic antimicrobial agent, a quaternary ammonium compound, a biguanide, chlorohexidine, a triguanide, a bisbiguanide, a polymeric biguanide and a naturally occurring antibiotic compound, as well as analogs, derivatives, salts, ions and complexes thereof.

The Foamable Composition Essential Ingredients as Active Agents

In certain embodiments, the short chain alcohol possesses therapeutic properties on its own and therefore, it can be regarded as "active agent." For example, ethanol kills microorganisms and can be effective in the treatment or prevention of conditions that involve microbial infection, such as bacterial, fungal and viral conditions. Additionally, the defatting effect of alcohol is useful for the treatment of conditions which involve oily skin, such as acne, Rosacea and seborrheic dermatitis. The combination of a short chain alcohol and a therapeutically effective fatty alcohol or fatty acid may afford a synergistic beneficial effect in conditions characterized, for example, by infection and/or inflammation.

Because short chain alcohols are known to increase the rate of absorption of some compounds through organic tissues including skin and nails, formulations comprising such alcohols can be used as a drug delivery system.

Combination of Active Agents

Several disorders involve a combination of more than one etiological factor; and therefore, the use of more that one active agents is advantageous. For example, psoriasis involves excessive cell proliferation and inadequate cell differentiation as well as inflammation. Atopic dermatitis involves keratinocyte growth abnormality, skin dryness and inflammation. Bacterial, fungal and viral infections involve pathogen colonization at the affected site and inflammation. Hence, in many cases, the inclusion of a combination of active agents in the foamable pharmaceutical composition can be desirable. Thus, in one or more embodiments, the foamable composition further includes at least two active agents, in a therapeutically effective concentration.

Fields of Applications

The foamable composition is suitable for treating any inflicted surface. In one or more embodiments, foamable carrier is suitable for administration to the skin, a body surface, a mucosal surface and a body cavity, e.g., the cavity and/or the mucosa of the nose, mouth and eye, the ear, the respiratory system, the vagina or the rectum (severally and interchangeably termed herein "target site").

By selecting a suitable active agent, or a combination of two or more active agents, the foamable composition is useful in treating an animal or a human patient having any one of a variety of dermatological disorders, including dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, granuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing moistens, gangrene, scarring, and vitiligo.

Likewise, the foamable composition is suitable for treating a disorder of a body cavity or mucosal surface, e.g., the mucosa of the nose, mouth, eye, ear, respiratory system, vagina or rectum. Non limiting examples of such conditions include chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranuloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment the composition is useful for the treatment of an infection. In one or more embodiments, the composition is suitable for the treatment of an infection, selected from the group of a bacterial infection, a fungal infection, a yeast infection, a viral infection and a parasitic infection.

In an embodiment the composition is useful for the treatment of a wound, ulcer and burn.

In an embodiment the target site is selected from the group consisting of the skin, a body cavity, a mucosal surface, the nose, the mouth, the eye, the ear canal, the respiratory system, the vagina and the rectum.

The composition is also suitable for administering a hormone to the skin or to a mucosal membrane or to a body cavity, in order to deliver the hormone into the tissue of the target organ, in any disorder that responds to treatment with a hormone.

In an embodiment the target site is selected from the group consisting of the skin, a body cavity, a mucosal surface, the nose, the mouth, the eye, the ear canal, the respiratory system, the vagina and the rectum.

In an embodiment the disorder is selected from the group consisting of dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, granuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo, chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranuloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum; and wherein the active agent is suitable for treating said disorder.

In one embodiment the disorder is an inflammation, skin inflammation, acne, rosacea, actinic keratosis, skin cancer, a local pain, joint pain and ostheoarthritis; the active agent is a nonsteroidal anti-inflammatory drug, given at a therapeutically effective concentration.

In one or more embodiments, the active agent may be a placebo or a cosmetic agent.

Cosmetic Use

In one or more embodiments, the composition may be used for cosmetic use. For example it may be used as part of a cosmetic formulation to prevent a cosmetic disorder or to improve the skin. Alternatively it may be used with cosmetic effect for example as a cosmetic remover. It can be dispensed in small quantities as a foam targeted to a surface and applied locally with mechanical force causing the foam to break.

EXAMPLES

The invention is described with reference to the following examples, in a non-limiting manner. The following examples exemplify the foamable compositions and methods described herein. The examples are for the purposes of illustration only and are not intended to be limiting. Many variations will suggest themselves and are within the full intended scope.

Example 1

General Manufacturing Procedures

The following procedures are used to produce the foam samples described in the examples below, in which only the steps relevant to each formulation are performed depending on the type and nature of ingredients used.

Step 1: Ethanol and, if present, humectants are mixed at room temperature. Polymers or gelling agents, if present, are added at room temperature under mixing until formulation homogeneity is obtained. Surfactants and fatty alcohols or fatty acids, if present, are added under agitation until complete dissolution.

Step 2: Any pH-buffering agents are added to water at room temperature under mixing until complete dissolution.

Step 3: The alcoholic phase is added to the water phase under mixing until homogeneity is obtained.

Step 4: The formulation is packaged in aerosol canisters which are crimped with a valve, pressurized with propellant and equipped with an actuator suitable for foam dispensing. Optionally a metered dosage unit can be utilized to achieve delivery of repeatable measured doses of foam, f. or example as described in U.S. Provisional Application No. 61/363,577 entitled "APPARATUS AND METHOD FOR RELEASING A UNIT DOSE OF CONTENT FROM A CONTAINER," filed Jul. 12, 2010, which is incorporated herein by reference.

Note: hydrophobic substances, if present, are added to the alcohol phase with the fatty alcohols and or fatty alcohols.

Materials

TABLE 1

Exemplary possible ingredients suitable for the production of foamable compositions disclosed herein. Equivalent materials from other manufacturers can also be used satisfactorily.

| Chemical Name | Function | Commercial Name | Supplier |
|---|---|---|---|
| Acrylates/C10-30 alkyl acrylate crosspolymer | Gelling agent | Pemulen TR2 | Noveon |
| Behenyl alcohol | Foam adjuvant | Lanette 22 | Cognis |
| Benzoyl Peroxide | Active agent | Benzoyl Peroxide | Spectrum |
| Betamethasone Valerate | Active agent | Betamethasone Valerate | Crystal Pharma |
| Carbomer 934P | Gelling agent | Carbopol 934P | Spectrum |
| Cetostearyl alcohol | Foam adjuvant | Speziol C16-C18 | Cognis |
| Cetyl alcohol | Foam adjuvant | Speziol C16 | Cognis |
| Citric acid | pH modifying agent | Citric acid | R. de Haen |
| Clindamycin Phosphate | Active agent | Clindamycin Phosphate | Uqifa |
| Coco-betaine | Surfactant | Dehyton | Cognis |
| Diclofenac sodium | Active agent | Diclofenac sodium | Sriken |
| Ethanol absolute | Solvent | Ethanol | Bio Lab |
| Glycerin | Humectant | Glycerin | Cognis |
| Hexylene Glycol | Solvent | Hexylene Glycol | Spectrum |
| Hydroxypropyl cellulose | Gelling agent | Klucel EF | Hercules |
| Hydroxypropyl methylcellulose | Gelling agent | Methocel K100M | Colorcon Dow |
| Laureth-23 | Surfactant | Brij 35P | Uniqema |
| Mometasone Furoate | Active agent | Mometasone Furoate | Sicor |
| Myristic acid | Foam adjuvant | Myristic acid | Spectrum |
| Myristyl alcohol | Foam adjuvant | Speziol C14 | Cognis |
| Oleth-20 | Surfactant | Samulsol 98 | Seppic |
| PEG-40 Stearate | Surfactant | Myrj 52S | Croda |
| Poloxamer 407 | Gelling agent | Lutrol F127 | BASF |
| Polyethylene glycol 400 | Humectant | PEG-400 | Inoes |
| Polysorbate 60 | Surfactant | Polysorbate 60 | Cognis |
| Propane/Isobutane/Butane (55:18:27) | Propellant | AP-70 | Aeropress Corporation |
| Propylene glycol | Humectant | Propylene Glycol | Gadot |
| Sodium citrate | pH modifying agent | Sodium Citrate | Archer Daniels Mild |
| Sodium lauryl sarcosinate | Surfactant | Lanette E PH | Cognis |
| Sodium Lauryl Sulfate | Surfactant | Sodium dodecyl sulfate | Cognis |
| Stearic acid | Foam adjuvant | Stearic acid | Spectrum |
| Stearyl Alcohol | Foam adjuvant | Speziol C18 | Cognis |
| Triethanolamine | pH modifying agent | TEA | Gadot |
| Xanthan Gum | Gelling agent | Xanthan Gum 11K | CP Kelco US |

Production under Vacuum

Optionally, the foamable carrier may be produced under nitrogen and under vacuum. Whilst the whole process can be carried out under an oxygen free environment, it can be sufficient to apply a vacuum after heating and mixing all the ingredients to obtain an emulsion or homogenous liquid. Preferably the production chamber is equipped to apply a vacuum.

Canisters Filling and Crimping

Each aerosol canister is filled with the pre-foam formulation ("PFF", i.e., foamable carrier) and crimped with valve using vacuum crimping machine. The process of applying a vacuum will cause most of the oxygen present to be eliminated. Addition of hydrocarbon propellant may without being bound by any theory further help to reduce the likelihood of any remaining oxygen reacting with the active ingredient. It may do so, without being bound by any theory, by one or more of dissolving in, to the extent present, the oil or hydrophobic phase of the formulation, by dissolving to a very limited extent in the aqueous phase, by competing with some oxygen from the formulation, by diluting out any oxygen, by a tendency of oxygen to occupy the dead space, and/or by oxygen occupying part of the space created by the vacuum being the unfilled volume of the canister or that remaining oxygen is rendered substantially ineffective in the formulation.

Pressurizing & Propellant Filling

Pressurizing is carried out using a hydrocarbon gas or gas mixture. Canisters are filled and then warmed for 30 seconds in a warm bath at 50° C. and well shaken immediately thereafter.

Tests

By way of non-limiting example the objectives of hardness, collapse time and freeze-thaw cycle ("FTC") stability tests are briefly set out below as would be appreciated by a person of the art.

Collapse Time

Collapse Time, which is the measure of thermal stability, is examined by dispensing a given quantity of foam and photographing sequentially its appearance with time during incubation at 36° C. The collapse time result is defined as the time when the foam height reaches 50% of its initial height or if the foam has not yet reached 50% of its initial height after say 180 seconds then the collapse time is recorded as being>180. By way of illustration one foam may remain at 100% of its initial height for three minutes, a second foam may reach 90% of its initial height after three minutes, a third foam may reach 70% of its initial height after three minutes, and a fourth foam may reach 51% of its initial height after three minutes, nevertheless in each of these four cases the collapse time is recorded as >180secs since for practical purposes for easy application by a patient to a target the majority of the foam remains intact for more than 180secs. If the foam for example reaches 50% of its original height after say 100 seconds it would be recorded as having a collapse time of 100 seconds. It is useful for evaluating foam products, which maintain structural stability at skin temperature for at least 1 minute. Foams which are structurally stable on the skin for at least one minute are termed "short term stable" carriers or foams.

Alternatively, a Simple Collapse Time can be assessed by placing a foam sample on the warm fingers of a volunteer and measuring the time it takes to melt on the fingers, for example, as observed in Example 4 herein.

Density

In this procedure, the foam product is dispensed into vessels (including dishes or tubes) of a known volume and weight. Replicate measurements of the mass of foam filling the vessels are made and the density is calculated. The canister and contents are allowed to reach room temperature. The canister is shaken to mix the contents and then 5-10 mL of the contents is dispensed and discarded. Next the foam is dispensed into a pre-weighed tube, filling it until excess is extruded. Immediately excess foam is leveled off and removed at both ends and the filled tube is weighed on the weighing balance.

Viscosity

Viscosity is measured with Brookfield LVDV-II+PRO with spindle SC4-25 at ambient temperature and 10, 5 and 1 RPM. Viscosity is usually measured at 10RPM. However, at about the apparent upper limit for the spindle of ~>50,000CP, the viscosity at 1RPM may be measured, although the figures are of a higher magnitude. Unless otherwise stated viscosity of the pre-foam formulation (PFF) is provided. It is not practical to try and measure the viscosity of the foamable formulation with regular propellants since they have to be stored in sealed pressurized canisters or bottles. In order to simulate the viscosity in the foamable formulations with propellant an equivalent weight of pentane (a low volatile hydrocarbon) is added to and mixed with the pre-foam formulation and left overnight. The viscosity is then measured as above.

FTC (Freeze Thaw Cycles)

Foam appearance under extreme conditions of repeated heating and cooling is evaluated by cycling through cooling, heating, (first cycle) cooling, heating (second cycle) etc., conditions, commencing with –10° C. (24 hours) followed by +40° C. (24 hours) and measuring the appearance following each cycle. The cycle is repeated for up to three times.

Chemical Stability

The amount of active agent present is analyzed in foam expelled from various pressurized canisters containing foam formulations using HPLC. Analysis is carried out at zero time and at appropriate time intervals thereafter. The canisters are stored in controlled temperature incubators at one or more of 5° C., at 25° C., at, 40° C. and at 50° C. At appropriate time intervals canisters are removed and the amount of active agent in the foam sample is measured.

Bubble Size

Foams are made of gas bubbles entrapped in liquid. The bubble size and distribution reflects in the visual texture and smoothness of the foam. Foam bubbles size is determined by dispensing a foam sample on a glass slide, taking a picture of the foam surface with a digital camera equipped with a macro lens. The diameter of about 30 bubbles is measured manually relatively to calibration standard template. Statistical parameters such as mean bubble diameter, standard deviation and quartiles are then determined. Measuring diameter may also be undertaken with image analysis software. The camera used is a Nikon D4OX Camera (resolution 10MP) equipped with Sigma Macro Lens (ref: APO MACRO 150 mm F2.8 EX DG HSM). Pictures obtained are cropped to keep a squared region of 400 pixels×400 pixels.

Microscope Size:

The light microscope enables observing and measuring particles from few millimeters down to one micron. Light microscope is limited by the visible light wavelength and therefore is useful to measuring size of particles above 800 nanometers and practically from 1 micron (1,000 nanometers).

Shakability

Shakability represents the degree to which the user is able to feel/hear the presence of the liquid contents when the filled pressurized canister is shaken. Shaking is with normal mild force without vigorous shaking or excessive force. When the user cannot sense the motion of the contents during shaking the product may be considered to be non-shakable. This property may be of particular importance in cases where shaking is required for affecting proper dispersion of the contents.

Shakability Scoring:

| | |
|---|---|
| Good shakability (conforms to required quality specification) | 2 |
| Moderate shakability (conforms to required quality specification) | 1 |
| Not shakable (fails to meet required quality specification) but may still be flowable and allow foam formation of quality | 0 |
| Is substantially not able to pass through valve | Block |

Example 2

Hydro-Alcoholic Formulations Containing a Combination of Surfactants and Polymers Several surfactants were used in combination with gelling agents (polymers) and checked for their foaming properties.

As described in Table 2a below, formulations 1, 7, 8 and 12 containing laureth-23 or oleth-20 non-ionic surfactants in combination with various polymers did not give rise to foams but merely generated bubbly liquids.

TABLE 2a

Formulations containing laureth-23 or oleth-20

| | Formulation | | | |
|---|---|---|---|---|
| Ingredient | 1 % w/w | 7 % w/w | 8 % w/w | 12 % w/w |
| Ethanol | 51.00 | 51.50 | 50.50 | 51.00 |
| Purified water | 36.00 | 40.00 | 40.90 | 36.90 |
| PEG 400 | — | — | 5.00 | 5.00 |
| Propylene glycol | 5.00 | — | — | — |
| Glycerin | — | 5.00 | — | — |
| Hydroxypropyl cellulose | — | — | 1.50 | — |

TABLE 2a-continued

Formulations containing laureth-23 or oleth-20

| Ingredient | Formulation 1 % w/w | Formulation 7 % w/w | Formulation 8 % w/w | Formulation 12 % w/w |
|---|---|---|---|---|
| Poloxamer 407 20% solution | 5.00 | — | — | 5.00 |
| Carbomer 974 | — | 0.40 | — | — |
| Triethanolamine | — | 0.10 | — | — |
| Laureth-23 | 2.00 | 2.00 | 2.00 | — |
| Oleth-20 | — | — | — | 2.00 |
| Citric acid | 0.40 | 0.40 | 0.07 | 0.07 |
| Sodium citrate | 0.60 | 0.60 | 0.03 | 0.03 |
| Total | 100.00 | 100.00 | 100.00 | 100.00 |
| Propellant AP-70 | 8.00 | 8.00 | 8.00 | 8.00 |
| Results | | | | |
| Foam Quality | Poor | Poor | Poor | Poor |
| Product Clarity | Yes | No | Yes | Yes |

As described in Table 2b below, formulations 2, 5 and 11 containing polysorbate 60 and PEG 40 stearate non-ionic surfactants in combination with various polymers did not give rise to foams but merely generated bubbly liquids.

TABLE 2b

Formulations containing polysorbate 60 and PEG 40 stearate

| Ingredient | Formulation 2 % w/w | Formulation 5 % w/w | Formulation 11 % w/w |
|---|---|---|---|
| Ethanol | 50.50 | 51.50 | 51.50 |
| Purified water | 40.00 | 40.00 | 40.90 |
| PEG400 | — | — | 5.00 |
| Propylene glycol | — | 5.00 | — |
| Glycerin | 5.00 | — | — |
| Hydroxypropyl cellulose | 1.50 | — | — |
| Hydroxypropyl methylcellulose | — | 0.50 | — |
| Carbomer 974 | — | — | 0.40 |
| Triethanolamine | — | — | 0.10 |
| Polysorbate 60 | 0.60 | 0.60 | 0.60 |
| PEG 40 Stearate | 1.40 | 1.40 | 1.40 |
| Citric acid | 0.40 | 0.40 | 0.07 |
| Sodium citrate | 0.60 | 0.60 | 0.03 |
| Total | 100.00 | 100.00 | 100.00 |
| Propellant AP-70 | 8.00 | 8.00 | 8.00 |
| Results | | | |
| Foam Quality | Poor | Poor | Poor |
| Product Clarity | Yes | Yes | No |

As described in Table 2c below, formulations 3, 9 and 10 containing sodium lauryl sulfate and coco-betaine (anionic and zwitterionic surfactants) in combination with various polymers did not give rise to foams but merely generated bubbly liquids.

TABLE 2c

Formulations containing sodium lauryl sulfate and coco-betaine

| Ingredient | Formulation 3 % w/w | Formulation 9 % w/w | Formulation 10 % w/w |
|---|---|---|---|
| Ethanol | 52.90 | 52.40 | 51.90 |
| Purified water | 40.00 | 36.90 | 40.90 |
| PEG 400 | 5.00 | — | — |
| Propylene glycol | — | — | 5.00 |
| Glycerin | — | 5.00 | — |
| Hydroxypropyl cellulose | — | — | 1.50 |
| Poloxamer 407 20% solution | — | 5.00 | — |
| Hydroxypropyl methylcellulose | 0.50 | — | — |
| Sodium lauryl sulfate | 0.30 | 0.30 | 0.30 |
| Coco-betaine | 0.30 | 0.30 | 0.30 |
| Citric acid | 0.40 | 0.07 | 0.07 |
| Sodium citrate | 0.60 | 0.03 | 0.03 |
| Total | 100.00 | 100.00 | 100.00 |
| Propellant AP-70 | 8.00 | 8.00 | 8.00 |
| Results | | | |
| Foam Quality | Poor | Poor | Poor |
| Product Clarity | Yes | Yes | Yes |

As described in Table 2d below, formulations 17 and 18 containing sodium lauryl sarcosinate and sodium cetearyl sulfate anionic surfactants in combination with various polymers did not give rise to foams but merely generated bubbly liquids.

TABLE 2d

Formulations containing sodium lauryl sarcosinate and sodium cetearyl sulfate

| Ingredient | Formulation 017 % w/w | Formulation 018 % w/w |
|---|---|---|
| Ethanol | 52.90 | 52.40 |
| Purified water | 40.90 | 36.90 |
| PEG 400 | 5.00 | — |
| Glycerin | — | 5.00 |
| Poloxamer 407 20% solution | — | 5.00 |
| Hydroxypropyl methylcellulose | 0.50 | — |
| Sodium lauryl sarcosinate | 0.30 | 0.30 |
| Sodium cetearyl sulfate | 0.30 | 0.30 |
| Citric acid | 0.07 | 0.07 |
| Sodium citrate | 0.03 | 0.03 |
| Total PFF components: | 100.00 | 100.00 |
| Propellant AP-70* | 8.00 | 8.00 |
| Results | | |
| Foam Quality | Poor | Poor |
| Product Clarity | Yes | Yes |

As described in Table 2e below, formulations 52, 53 and 54 containing polymeric agents alone such as Hydroxypropyl cellulose (a cellulose-based polymer), poloxamer 188 (a polymer having some surfactant-like properties) and Acrylates/C10-30 alkyl acrylate crosspolymer (an amphiphilic polymer said to have some emulsifying-like properties) did not give foams but bubbly liquids.

TABLE 2e

Formulations containing various polymeric agents

| Ingredient | Formulation 52 % w/w | Formulation 53 % w/w | Formulation 54 % w/w |
|---|---|---|---|
| Ethanol | 50.00 | 50.00 | 50.00 |
| Purified water | 47.00 | 47.00 | 47.00 |
| Hydroxypropyl cellulose | 3.00 | — | 1.50 |
| Poloxamer 188 | — | 3.00 | — |
| Acrylates/C10-30 alkyl acrylate crosspolymer | — | — | 3.00 |
| Total | 100.00 | 100.00 | 100.00 |
| Propellant AP-70 | 8.00 | 8.00 | 8.00 |
| Results | | | |
| Foam Quality | Poor | Poor | Poor |

This study shows that polymeric agents alone or combinations of polymeric agents one of which has some surfactant like properties are not sufficient to achieve good foaming properties in the case of water-based vehicles containing large amounts of short chain alcohols.

Polymer alone, surfactant plus polymer and combinations of polymers, one of which has surfactant like properties all failed to produce a quality hydro-alcoholic foam. This is a surprising result considering that based on the prior art, surfactants are known as useful foam boasting agents, especially when used in combination with polymeric agents. It appears that high levels of SCA's e.g. ethanol have an apparent defoaming effect or destabilizing effect, and thus it is not at all obvious how to obtain good quality foams with high levels of short chain alcohols.

Example 3

Hydro-Alcoholic Formulations Containing Fatty Alcohols or Fatty Acids

The influence of fatty alcohols and fatty acids on the foaming properties of hydro-alcoholic formulations was studied. As described in Table 3a below, formulation 4 containing a carbomer polymer and a mixture behenyl and stearyl alcohol did not give a foam but a bubbly liquid.

Surprisingly, however, the use of a cellulose-based polymer such as Hydroxypropyl methylcellulose in combination with behenyl and stearyl alcohol improves the foaming properties and good quality foam was produced as shown in formulation 6. So hydroxypropyl methylcellulose appears to be preferred over a pH sensitive expandable polymer like carbopol.

Unexpectedly, it has also been discovered that the use of ceto-stearyl alcohol (a mixture of cetyl and stearyl alcohol) substantially improves the foaming properties of hydro-alcoholic formulations. For example, formulation 15 which contains a combination of carbomer and ceto-stearyl alcohol unexpectedly gives an excellent quality breakable foam that has a collapse time of about 90 sec at 36° C., whereas 4 (combination of carbomer, behenyl and stearyl alcohol) merely gives a bubbly liquid.

The use of cellulose-based polymers such as hydroxypropyl methylcellulose or hydroxypropyl cellulose further improves the foaming properties of hydro-alcoholic formulations. Formulation 16 which contains a combination of Hydroxypropyl methylcellulose and ceto-stearyl alcohol provides an excellent quality breakable foam that has a collapse time of about 120 sec at 36° C. As observed, the single-phase formulations 10A and 10B, combinations of Hydroxypropyl cellulose and ceto-stearyl alcohol are particularly successful and can provide excellent quality breakable foams that have a collapse time of more than 120 sec at 36° C.

We have thus discovered that certain polymers and certain fatty alcohols are hydro-alcoholic composition booster stabilizing agents of particular importance for hydro-alcoholic formulations. In certain embodiments the fatty alcohols have a carbon chain of between 14 to 18 carbons. As can be observed from the investigation of fatty alcohols and polymers detailed below in Tables 3a-3c the preferable polymers are cellulose-based polymers and preferable fatty alcohols have a saturated carbon chain of between 16 to 18 carbons. These two composition booster stabilizing agents can work synergistically to provide breakable foams of excellent quality which are stable at 36° C. (i.e they do not breakdown rapidly on being exposed to a surface or a space at 36° C.).

TABLE 3a

Formulations containing fatty alcohols

| Ingredient | 4 % w/w | 6 % w/w | 15 % w/w | 16 % w/w | 10A % w/w | 10B % w/w |
|---|---|---|---|---|---|---|
| Ethanol | 51.80 | 51.80 | 51.50 | 51.50 | 51.90 | 50.20 |
| Purified water | 40.00 | 40.00 | 40.90 | 40.90 | 38.30 | 40.20 |
| Propylene glycol | 5.00 | — | 5.00 | — | 5.00 | 5.00 |
| Glycerin | — | 5.00 | — | 5.00 | — | — |
| Hydroxypropyl cellulose | — | — | — | — | 3.00 | 1.50 |
| Hydroxypropyl methylcellulose | — | 0.50 | — | 0.50 | — | — |
| Carbomer 974 | 0.40 | — | 0.40 | — | — | — |
| Triethanolamine | 0.10 | — | 0.10 | — | — | — |
| Behenyl alcohol | 1.10 | 1.10 | — | — | — | — |
| Stearyl alcohol | 0.60 | 0.60 | — | — | — | — |
| Ceto-stearyl alcohol | — | — | 2.00 | 2.00 | 1.70 | 3.00 |

TABLE 3a-continued

Formulations containing fatty alcohols

| | Formulation | | | | | |
|---|---|---|---|---|---|---|
| | 4 % w/w | 6 % w/w | 15 % w/w | 16 % w/w | 10A % w/w | 10B % w/w |
| Citric acid | 0.40 | 0.40 | 0.07 | 0.07 | 0.07 | 0.07 |
| Sodium citrate | 0.60 | 0.60 | 0.03 | 0.03 | 0.03 | 0.03 |
| Total | 100.00 | 100.00 | 100.00 | 100.00 | 100.00 | 100.00 |
| Propellant AP-70 | 8.00 | 8.00 | 8.00 | 8.00 | 8.00 | 8.00 |
| Results | | | | | | |
| Foam Quality | Poor | Good | Excellent | Excellent | Excellent | Excellent |
| Collapse Time at 36° C. (sec) | N/A | N/A | 90 | 120 | >180 | 120 |
| Product Clarity | No | No | No | Yes | Yes | Yes |

TABLE 3b

Additional results for Formulation 10B

| Foam pH (diluted 1:5) | 3.40 |
|---|---|
| Foam Density (g/mL) | 0.096 |
| Microscopic observation | no crystals |
| Stability after centrifugation at 3K, 10 min | Homogeneous |
| Stability after centrifugation at 10K, 10 min | Homogeneous |
| Pre-foam formulation viscosity at 10 rpm (cP) | 319 |
| Foam Hardness (grams) | 24.53 |
| Mean foam bubble size (micrometers) | 62 |

An additional study was conducted on the influence of the carbon chain length of fatty alcohol and fatty acids on parameters such as foam quality. As described in Table 3c below, good quality foams can be obtained with combinations of polymer and certain fatty acids or certain fatty alcohols. For example formulation 55 containing a combination of Hydroxypropyl cellulose and stearic acid gave a good quality foam, whereas formulation 61 containing Hydroxypropyl cellulose and isostearic acid only resulted in a bubbly liquid. Without being bound by any theory the isostearic acid which is non linear and liquid in contrast to stearic acid being linear and solid and may generate some steric hindrance and lower viscosity. Thus, the present invention is not limited to fatty alcohols and fatty alcohol combinations but includes also the use of fatty acids and fatty acid combinations as stabilizing agents in hydro-alcoholic foams or in combination with fatty alcohols (see e.g. example 11). The formulations were surprisingly successful in the absence of a customary surfactant.

To evaluate the possible importance of the carbon chain length on the foaming properties of hydro-alcoholic formulations, several fatty alcohols containing from 14 to 22 carbons were used in combination with polymer to create foams. Surprisingly, formulations with fatty alcohol comprising 14 (myristyl alcohol) or 22 (behenyl alcohol) carbons on their own failed to generate a quality foam and only produced bubbly liquids, as shown in the results for formulations 56 and 59. However, a fatty alcohol having a carbon chain length of about 16 to about 18 gave foams of quality in combination with Hydroxypropyl cellulose. For example, cetyl alcohol (C16) provided fairly good quality foam and stearyl alcohol gave good quality foams, as shown in formulations 57 and 58. Significantly, and unexpectedly, the combination of cetyl alcohol and stearyl alcohol is synergistic and results in excellent quality foam as shown in the results for formulation 60, which contains Hydroxypropyl cellulose and cetostearyl alcohol, a mixture of 50% cetyl alcohol and 50% stearyl alcohol. Such excellent quality foams were not observed in the examples containing either cetyl alcohol alone or stearyl alcohol alone. [See Tables 3a and c and compare and contrast the foam quality for formulations 6, 57, 58 and 60].Thus, we have discovered that a combination of two fatty alcohols having a carbon chain length of about 16 to about 18 have a synergistic effect and dramatically enhance the foaming properties of hydro-alcoholic formulations.

TABLE 3c

Formulations containing fatty alcohols and fatty acids of different carbon chain length

| | Formulation | | | | | | |
|---|---|---|---|---|---|---|---|
| | 55 % w/w | 61 % w/w | 56 % w/w | 57 % w/w | 58 % w/w | 59 % w/w | 60 % w/w |
| Ingredient | | | | | | | |
| Ethanol | 50.00 | 50.00 | 50.00 | 50.00 | 50.00 | 50.00 | 50.00 |
| Water | 45.50 | 45.50 | 45.50 | 45.50 | 45.50 | 45.50 | 45.50 |
| Stearic acid (C18) | 3.00 | — | — | — | — | — | — |
| Isostearic acid (C18) | — | 3.00 | — | — | — | — | — |
| Myristyl alcohol (C14) | — | — | 3.00 | — | — | — | — |
| Cetyl alcohol (C16) | — | — | — | 3.00 | — | — | — |
| Stearyl alcohol (C18) | — | — | — | — | 3.00 | — | — |
| Behenyl alcohol (C22) | — | — | — | — | — | 3.00 | — |
| Cetostearyl alcohol (C16 + C18) | — | — | — | — | — | — | 3.00 |

TABLE 3c-continued

Formulations containing fatty alcohols and fatty acids of different carbon chain length

| | Formulation | | | | | | |
|---|---|---|---|---|---|---|---|
| | 55 % w/w | 61 % w/w | 56 % w/w | 57 % w/w | 58 % w/w | 59 % w/w | 60 % w/w |
| Hydroxypropyl cellulose | 1.50 | 1.50 | 1.50 | 1.50 | 1.50 | 1.50 | 1.50 |
| Total | 100.00 | 100.00 | 100.00 | 100.00 | 100.00 | 100.00 | 100.00 |
| Propellant AP-70 | 8.00 | 8.00 | 8.00 | 8.00 | 8.00 | 8.00 | 8.00 |
| Results | | | | | | | |
| Foam Quality | Good | Poor | Poor | Fairly Good | Good | Fair | Excellent |

Example 4

Thermal Stability—Comparative Example

Two foam formulations (Formulation 001 and 10B-9) were compared with a foam formulation from patent, U.S. Pat. No. 6,126,920, Example 1, as described in Table 4a. The foam samples were placed on fingers of a male volunteer and the thermal stability of each of the foams was assessed by measuring the time it takes to melt on the fingers. Foam formulation 001 and 10B-9 were thermally stable and did not melt on contact with the skin for more than three minutes, thus providing an easy and convenient application for the user of the product. In contrast, the foam formulation from U.S. Pat. No. 6,126,920, Example 1, which is described as a "quick-breaking" foam, was thermally unstable and quickly liquefied and melted on contact with the skin within 15 seconds, making the product application difficult for the user and causing the drug to absorb on the fingers, rather than on the intended target site of treatment. Therefore, it has been found that by combining suitable polymeric agent with suitable foam adjuvants it is possible to exclude the need for surfactant in hydro alcoholic formulation yet achieving foams with enhanced thermal stability.

TABLE 4a

Comparative example

| | Formulation | | |
|---|---|---|---|
| Ingredient | 001 % w/w | 10B-9 % w/w | Sample according to U.S. Pat. No. 6,126,920 Example 1 % w/w |
| Ethanol | 50.20 | 50.20 | 57.79 |
| Purified water | 41.48 | 40.20 | 33.69 |
| Propylene glycol | 5.00 | 5.00 | 2.00 |
| Hydroxypropyl cellulose | 1.50 | 1.50 | — |
| Cetostearyl alcohol | — | 3.00 | — |
| Citric acid | 0.07 | 0.07 | 0.073 |
| Sodium citrate | 0.03 | 0.03 | — |
| Potassium citrate | — | — | 0.027 |
| Polysorbate 60 | — | — | 0.40 |
| Octadecan-1-ol (stearyl alcohol) | 0.50 | — | 0.50 |
| Cetyl alcohol | 1.10 | — | 1.10 |
| Betamethasone valerate | 0.12 | 0.12 | 0.12 |
| Hydrocarbon propellant (butane/propane/isobutane) | 8.00 | 8.00 | 4.30 |
| Time to 50% melting | >3 minutes | >3 minutes | 15 seconds |

Two amended formulations based on foam formulations from patent, U.S. Pat. No. 6,126,920, Example 1 were prepared as described in Table 4b. A foam Sample according to U.S. Pat. No. 6,126,920 Example 1 with surfactant but where all the fatty alcohols were removed from the composition failed to produce foam. A foam Sample according to U.S. Pat. No. 6,126,920 Example 1 with surfactant and containing 3% cetostearyl alcohol produced quality foam. These surprising results emphasize the importance of including suitable fatty alcohols into hydro-alcoholic foam formulation TABLE 4b Comparative example

| | Formulation | |
|---|---|---|
| Ingredient | Sample according to U.S. Pat. No. 6,126,920 Example 1 with removed fatty alcohols % w/w | Sample according to U.S. Pat. No. 6,126,920 Example 1 with 3% Cetostearyl alcohol % w/w |
| Ethanol | 57.79 | 57.79 |
| Purified water | 35.29 | 32.29 |
| Propylene glycol | 2.00 | 2.00 |
| Cetostearyl alcohol | — | 3.00 |
| Citric acid | 0.073 | 0.073 |
| Potassium citrate | 0.027 | 0.027 |
| Polysorbate 60 | 0.40 | 0.40 |
| Betamethasone valerate | 0.12 | 0.12 |
| Hydrocarbon propellant (butane/propane/isobutane) | 4.30 | 4.30 |
| Total | 100.00 | 100.00 |
| Foam Quality | Poor | Excellent |

Example 5

Stability of a Steroid in Hydro-Alcoholic Formulations

This example illustrates the stability of betamethasone 17 valerate (BMV-17) in two foam compositions, namely 10B9 and 16B as described in Table 5a below. Samples a were stored at 5° C. and 40° C., and the concentrations of betamethasone 17 valerate and its respective degradation product betamethasone 21 valerate (BMV-21) were determined by UPLC. The stability test results following 3 and 6 months of storage are shown in Table 5b.

TABLE 5a

Composition of foam formulation incubated during 3 months and 6 months

| Ingredient | 10B-9 % w/w | 16B % w/w |
|---|---|---|
| Ethanol | 50.20 | 51.50 |
| Purified water | 40.20 | 40.90 |
| Propylene glycol | 5.00 | — |
| Glycerin | — | 5.00 |
| Hydroxypropyl cellulose | 1.50 | — |
| Hydroxypropyl methylcellulose | — | 0.50 |
| Cetostearyl alcohol | 3.00 | 2.00 |
| Citric acid | 0.07 | 0.07 |
| Sodium citrate | 0.03 | 0.03 |
| Betamethasone valerate-17 | 0.12 | 0.12 |
| Hydrocarbon Propellant AP-70 | 8.00 | 8.00 |

TABLE 5b

Stability results of foam compositions containing betamethasone valerate-17

| Time-point | Component | Formulation 10-B % w/w | Formulation 16B % w/w |
|---|---|---|---|
| 3 months at 5° C. | BMV-17 | 0.116 | 0.120 |
|  | BMV-21 | 0.000 | 0.000 |
| 3 months at 40° C. | BMV-17 | 0.115 | 0.118 |
|  | BMV-21 | 0.003 | 0.004 |
| 6 months at 5° C. | BMV-17 | 0.117 | 0.120 |
|  | BMV-21 | 0.000 | 0.000 |
| 6 months at 40° C. | BMV-17 | 0.112 | 0.113 |
|  | BMV-21 | 0.006 | 0.008 |

The results after 3 months and 6 months at 5° C. show that no measurable degradation of the active agent or appearance of its degradation product occurred at this low storage temperature. The accelerated stability results after 3 months and 6 months at 40° C. showed a very minimal degradation of the active agent in the formulations, the degradation product BMV-21 being detected at the low levels of 2-3% at 3months and 6-8% at 6 months. Moreover, stability at 40° C. for 6m can be translated into an expected stability at room temperature for a year or more. The formulations herein thus show an ability to withstand extended accelerated stability for the steroidal active agent.

Example 6

Hydro-Alcoholic Formulations Containing Other Different Active Ingredients

Several active ingredients (API) were added to formulation 10B in order to assess the compatibility between the foam and the API. Parameters such as foam quality, foam density, collapse time and product clarity were evaluated as described in Table 6a below.

Formulations containing betamethasone valerate, diclofenac sodium, metronidazole, clindamycin phosphate and benzoyl peroxide (BPO) gave rise to breakable foams of excellent quality which were stable at 36° C. with a collapse time of more than 3 minutes. The first four formulations were clear single phase solutions. The fifth formulation containing BPO was not clear as BPO is insoluble. Interestingly, diclofenac appeared to increase foam density. Without being bound to any theory it is expected that in order to form a homogenous suspension of BPO a carbomer at a pH which at which its expansion is reduced would be included. See section on suspensions.

TABLE 6a

Formulations containing various active ingredients

| | Formulation | | | | |
|---|---|---|---|---|---|
| Ingredient | 10B9 % w/w | 10B1 % w/w | 10B2 % w/w | 10B3 % w/w | 10B7 % w/w |
| Ethanol | 50.20 | 50.20 | 50.20 | 50.20 | 50.20 |
| Purified water | 40.20 | 40.20 | 40.20 | 40.20 | 40.20 |
| Propylene glycol | 5.00 | 5.00 | 5.00 | 5.00 | 5.00 |
| Hydroxypropyl cellulose | 1.50 | 1.50 | 1.50 | 1.50 | 1.50 |
| Cetostearyl alcohol | 3.00 | 3.00 | 3.00 | 3.00 | 3.00 |
| Citric acid | 0.07 | 0.07 | 0.07 | 0.07 | 0.07 |
| Sodium citrate | 0.03 | 0.03 | 0.03 | 0.03 | 0.03 |
| Total | 100.00 | 100.00 | 100.00 | 100.00 | 100.00 |
| Betamethasone valerate | 0.12 | — | — | — | — |
| Diclofenac sodium | — | 1.00 | — | — | — |
| Metronidazole | — | — | 0.75 | — | — |
| Clindamycin phosphate | — | — | — | 1.00 | — |

TABLE 6a-continued

Formulations containing various active ingredients

| | Formulation | | | | |
|---|---|---|---|---|---|
| | 10B9 % w/w | 10B1 % w/w | 10B2 % w/w | 10B3 % w/w | 10B7 % w/w |
| Benzoyl Peroxide | — | — | — | — | 5.00 |
| Propellant AP-70 | 8.00 | 8.00 | 8.00 | 8.00 | 8.00 |
| Results | | | | | |
| Foam Quality | Excellent | Excellent | Excellent | Excellent | Excellent |
| Collapse Time at 36° C. (sec) | >180 | >180 | >180 | >180 | >180 |
| Foam Density (g/mL) | 0.096 | 0.165 | 0.074 | 0.063 | 0.067 |
| Product clarity | Yes | Yes | Yes | Yes | No |

Example 7

Hydro-Alcoholic Formulations Containing a Range of Ethanol Concentrations

Several formulations were prepared containing different concentrations of ethanol. Parameters such as foam quality, collapse time, foam density were evaluated as described in Table 7a below.

Formulations containing up to 60% ethanol provided breakable foams of good to excellent quality, that were stable at 36° C. having collapse times of more than 3 minutes. Also surprisingly the carrier without ethanol provided a good quality foam in the absence of surfactant. However, in the absence of alcohol the importance of polymer is enhanced. Ethanol despite its defoaming and thermolabile properties, unexpectedly improved the foam quality and generated stable breakable foam contrary to that seen in the prior art.

Example 8

Hydro-Alcoholic Formulations Containing Minimal Ingredients

Several ingredients were removed from formulation 10B in order to assess the contribution of each of them to the foam properties. Parameters such as foam quality, collapse time and product clarity were evaluated, and results described in Table 8a.

Foams of excellent quality that were stable at 36° C. were obtained in formulations without humectants and without pH buffering agents. However, the presence of a fatty alcohol with the polymer seem to be required, given that the formulation with hydroxypropyl cellulose polymer but lacking cetostearyl alcohol did not give foam but a bubbly liquid.

TABLE 7a

Fourmulations containing a range of ethanol concentrations

| | Formulation | | | | | |
|---|---|---|---|---|---|---|
| | 51 % w/w | 51b % w/w | 50 % w/w | 21 % w/w | 10A % w/w | 24 % w/w |
| Ingredient | | | | | | |
| Ethanol | — | — | 20.00 | 30.00 | 51.90 | 60.00 |
| Purified water | 95.50 | 97 | 75.50 | 60.20 | 38.30 | 30.20 |
| Propylene glycol | — | — | — | 5.00 | 5.00 | 5.00 |
| Hydroxypropyl cellulose | 1.50 | — | 1.50 | 3.00 | 3.00 | 3.00 |
| Cetostearyl alcohol | 3.00 | 3.00 | 3.00 | 1.70 | 1.70 | 1.70 |
| Citric acid | — | — | — | 0.07 | 0.07 | 0.07 |
| Sodium citrate | — | — | — | 0.03 | 0.03 | 0.03 |
| Total | 100.00 | 100.00 | 100.00 | 100.00 | 100.00 | 100.00 |
| Propellant AP-70 | 8.00 | 8.00 | 8.00 | 8.00 | 8.00 | 8.00 |
| Results | | | | | | |
| Foam Quality | Good | Poor | Excellent | Excellent | Excellent | Excellent |
| Collapse Time at 36° C. (sec) | >180 | | >180 | >180 | >180 | >180 |
| Foam Density | 0.103 | | 0.063 | 0.086 | 0.100 | 0.092 |

TABLE 8a

Formulations containing minimal ingredients

| | Formulation | | |
|---|---|---|---|
| | 10B % w/w | 27 % w/w | 29 % w/w |
| Ingredient | | | |
| Ethanol | 50.20 | 50.20 | 50.20 |
| Purified water | 40.20 | 45.30 | 43.20 |
| Propylene glycol | 5.00 | — | 5.00 |
| Hydroxypropyl cellulose | 1.50 | 1.50 | 1.50 |
| Cetostearyl alcohol | 3.00 | 3.00 | — |
| Citric acid | 0.07 | — | 0.07 |
| Sodium citrate | 0.03 | — | 0.03 |
| Total | 100.00 | 100.00 | 100.00 |
| Propellant AP-70 | 8.00 | 8.00 | 8.00 |
| Results | | | |
| Foam Quality | Excellent | Excellent | Poor |
| Collapse Time at 36° C. (sec) | 120 | >180 | — |
| Product clarity | Yes | Yes | Yes |

Example 9

Hydro-Alcoholic Formulations Containing Isopropanol

A foam formulation was prepared containing isopropanol (C3H7OH), which is another example of short chain alcohol. Parameters such as foam quality and collapse time were evaluated. As described in Table 8a, a foam of good quality was obtained in a formulation containing isopropanol.

TABLE 9a

Formulation containing isopropanol

| Formulation | 49 % w/w |
|---|---|
| Ingredient | |
| Isopropanol | 50.00 |
| Purified water | 45.50 |
| Hydroxypropyl cellulose | 1.50 |
| Cetostearyl alcohol | 3.00 |
| Total | 100.00 |
| Propellant AP-70 | 8.00 |
| Results | |
| Foam Quality | Good |

So, it follows that the above revelations as to how to achieve a short term stable breakable foam that is a foam which is stable upon exposure to body temperature despite the presence of a high level of ethanol should apply likewise mutatis mutandis to other short chain alcohols such as, isopropanol, propanol, butanaol, iso-butanol, t-butanol and pentanol. In one or more embodiments there is provided a short term stable breakable foam formulation comprising one or more short chain alcohols.

Example 10

Stability and Solubility of Mometasone Furoate in Hydro-Alcoholic Formulations This example illustrates the stability and solubility of mometasone furoate in two foam compositions, namely M009 and M016 as described in Table 10a below. Samples were stored at 40° C., and the concentrations of mometasone furoate were determined by UPLC. The stability test results following 1 and 2 months of storage are shown in Table 10b.

TABLE 10a

Composition of foam formulation incubated during 3 months

| | M009 % w/w | M016 % w/w |
|---|---|---|
| Ingredient | | |
| Isopropyl alcohol | — | 40.00 |
| Ethanol | 45.00 | — |
| Hexylene Glycol | 12.00 | 12.00 |
| Purified Water | 32.95 | 31.00 |
| Propylene Glycol | 5.00 | 10.95 |
| Hydroxypropylcellulose | 3.00 | 1.50 |
| Stearyl alcohol | — | 4.00 |
| Cetostearyl alcohol | 1.50 | — |
| Sodium citrate | 0.19 | 0.19 |
| Citric acid | 0.26 | 0.26 |
| Mometasone furoate | 0.10 | 0.10 |
| Total | 100.00 | 100.00 |
| Propellant AP70 | 8.00 | 8.00 |
| Results | | |
| Foam Quality | Excellent | Good |
| Collapse Time at 36° C. (sec) | >180 | >180 |
| Solubility of Mometasone Furoate | Soluble | Soluble |
| Visual inspection | Clear solution | Clear solution |

TABLE 10b

Stability results of a foam composition containing Mometasone furoate

| Time point | Formulation M009 Concentration of Mometasone Furoate |
|---|---|
| T0 | 0.0990 |
| 1 months at 40° C. | 0.0976 |
| 2 months at 40° C. | 0.0979 |

The results after 1 and 2 months of incubation at 40° C. show a very minimal degradation of the active agent in the formulations, The formulations herein thus show an extended accelerated stability of the steroidal active agent for at least 2 month.

Example 11

Hydro-Alcoholic Formulations Containing Fatty Alcohol and Fatty Acids

Parameters such as foam quality, collapse time and foam density were evaluated in foam formulations containing mixtures of fatty alcohol and fatty acids as described in Table 11 below.

TABLE 11

Formulations mixtures of fatty alcohol and fatty acids

| | Formulation | | |
|---|---|---|---|
| | 002 % w/w | 003 % w/w | 004 % w/w |
| Ingredient | | | |
| Ethanol | 58.0 | 58.0 | 58.0 |
| Purified water | 32.0 | 32.0 | 32.0 |
| Hydroxypropylcellulose | 1.5 | 1.5 | 1.5 |
| Propylene glycol | 6.9 | 6.9 | 6.9 |
| Cetyl alcohol | 0.8 | — | — |
| Myristyl alcohol | 0.8 | — | — |
| Stearyl alcohol | — | 0.8 | — |
| Stearic acid | — | 0.8 | 0.8 |
| Myristic acid | — | — | 0.8 |
| Total | 100.00 | 100.00 | 100.00 |
| AP-70 | 8.00 | 8.00 | 8.00 |
| Results | | | |
| Foam Quality | Good | Good | Good |
| Collapse Time at 36° C. (sec) | 55 | >180 | >180 |
| Foam Density (g/mL) | 0.074 | 0.049 | 0.189 |

When 3% cetyl alcohol and 3% myristyl alcohol are used alone in hydro-alcoholic formulations containing a polymeric agent, poor and fairly good foams are obtained respectively, as shown in formulations 56 and 57 described in Example 3. Poor foam collapses rapidly. Surprisingly however, when 0.8% myristyl alcohol is combined with 0.8% cetyl alcohol together with a polymeric agent, a short term stable breakable foam of good quality is achieved having a low density and a collapse time of about a minute. So the combination of cetyl and myristyl alcohol together with a polymeric agent achieves a synergistic effect.

A breakable foam of good quality with a collapse time in excess of 180 seconds and a low density was achieved by the combination of a fatty acid and a fatty alcohol, for example stearic acid and stearyl alcohol or a combination of two fatty acids, for example stearic acid and myristic acid.

In one or more embodiments, there is provided a hydro-alcoholic foamable formulation which provides a short term stable breakable foam with a collapse time of about 60 seconds at 36° C., and containing a combination of two or more fatty alcohols. In one or more embodiments the combination is synergistic.

In one or more embodiments, there is provided a hydro-alcoholic foamable formulation which provides a short term stable breakable foam with a collapse time of more than 180 sec at 36° C., and containing a combination of one or more fatty alcohols with one or more fatty acids or a combination of two or more fatty acids.

Example 12

Hydro-Alcoholic Formulations Containing Different Ratios of Fatty Alcohol

Parameters such as foam quality, collapse time and foam density were evaluated in foam formulations containing different ratios of cetyl alcohol and stearyl alcohol as described in Table 12 below.

TABLE 12

Formulations containing different ratios of fatty alcohol

| | Formulation | | |
|---|---|---|---|
| | 005 % w/w | 006 % w/w | 007 % w/w |
| Ingredient | | | |
| Ethanol | 58.0 | 58.0 | 58.0 |
| Purified water | 32.0 | 32.0 | 32.0 |
| Hydroxypropylcellulose | 1.5 | 1.5 | 1.5 |
| Propylene glycol | 6.9 | 6.9 | 6.9 |
| Cetyl alcohol | 1.1 | 0.8 | 0.5 |
| Stearyl alcohol | 0.5 | 0.8 | 1.1 |
| Total | 100.00 | 100.00 | 100.00 |
| AP-70 | 8.00 | 8.00 | 8.00 |
| Results | | | |
| Foam Quality | Good | Excellent | Excellent |
| Collapse Time | >180 | >180 | >180 |
| Foam Density | 0.060 | 0.073 | 0.059 |
| cetyl:stearyl alcohol ratio | 2.2:1 (i.e.11:5) | 1:1 | 1:2.2 (i.e.5:11) |

In the context of hydro-alcoholic formulations containing a polymeric agent, it can be seen that breakable foams of good to excellent quality with a collapse time of more than 180 seconds can be obtained by the combination of different ratios of two fatty alcohols, (in this example cetyl alcohol and stearyl alcohol). In one or more embodiments, the ratio of two fatty alcohols can be optimized in order to improve foam properties such as foam quality and foam collapse time.

Surprisingly, it appears that the foam quality can be strongly influenced by the ratio of mixtures of fatty alcohols such as cetyl and stearyl alcohol. Formulations having a cetyl:stearyl alcohol ratio of about 1:1 to about 5:11 gave breakable foam of excellent quality being stable by showing a collapse time of 3 minutes at 36° C. However, when the ratio of cetyl:stearyl alcohol was about 11:5 good quality foam was produced. It was further noted that stearyl alcohol appears to have a more significant role in the synergistic relationship than cetyl alcohol.

What is claimed is:

1. A method of treating a dermatological or mucosal disorder, comprising applying a composition to a skin surface in need of treatment for the dermatological or mucosal disorder, said composition comprising:
   one or more antibiotic agents;
   at least about 50% by weight of a short chain alcohol;
   a polymeric agent;
   between about 2% and about 50% of at least one organic carrier selected from the group consisting of a polar solvent, a hydrophobic organic carrier, and a mixture thereof;
   an active herbal extract;
   a metal; and
   an antioxidant;
   wherein the composition is a surfactant free composition.

2. The method of claim 1, wherein the disorder is selected from an infection, an inflammation, an acne, a rosacea, a psoriasis, an eczema, and an atopic dermatitis.

3. The method of claim 1, wherein the one or more antibiotic agents comprise a tetracycline antibiotic, an erythromycin antibiotic, or a salt, ion, or complex thereof.

4. The method of claim 1, wherein the one or more antibiotic agents are about 0.1% to about 5% by weight of the composition.

5. The method of claim 4, wherein the one or more antibiotic agents are about 1% by weight of the composition.

6. The method of claim 4, wherein the one or more antibiotic agents are about 5% by weight of the composition.

7. The method of claim 1, wherein the antioxidant is about 0.1% to about 10% by weight of the composition.

8. The method of claim 1, wherein the short chain alcohol comprises ethanol.

9. The method of claim 1, wherein the at least one organic carrier comprises a polar solvent.

10. The method of claim 9, wherein the polar solvent comprises propylene glycol.

11. The method of claim 1, wherein the polymeric agent comprises a cellulose ether.

12. The method of claim 11, wherein the cellulose ether comprises a hydroxypropyl cellulose.

13. The method of claim 9, wherein the polar solvent is about 5% to about 25% by weight of the composition.

14. The method of claim 10, wherein the polar solvent is about 17% to about 23% by weight of the composition.

15. The method of claim 3, wherein the one or more antibiotic agents are present in a therapeutically effective concentration.

16. The method of claim 1, wherein the polymeric agent is about 0.1% to about 5% by weight of the composition.

17. The method of claim 1, wherein: the one or more antibiotic agents comprise a tetracycline antibiotic, an erythromycin antibiotic, or a salt, ion, or complex thereof; the short chain alcohol comprises ethanol; the polymeric agent comprises a cellulose ether; and the at least one organic carrier comprises a polar solvent, wherein the polar solvent comprises a glycol.

18. The method of claim 17, wherein: the antibiotic is about 0.1% to about 5% by weight of the composition; the cellulose ether is about 0.1% to about 5% by weight of the composition; the glycol is about 5% to about 25% by weight of the composition; and the antioxidant is about 0.1% to about 10% by weight of the composition.

19. The method of claim 18, wherein the antibiotic is about 1% by weight of the composition.

20. The method of claim 18, wherein the cellulose ether comprises a hydroxypropyl cellulose and the glycol comprises a propylene glycol.

21. The method of claim 18, wherein the glycol is about 17% to about 23% by weight of the composition.

22. The method of claim 1, further comprising a liquefied or compressed gas propellant.

23. A method of treating a dermatological or mucosal disorder, comprising applying a composition to a skin surface in need of treatment for the dermatological or mucosal disorder, said composition comprising:
an active agent consisting of an antibiotic and/or a retinoid;
at least about 50% by weight of a short chain alcohol;
a polymeric agent; and
between about 2% and about 50% of at least one organic carrier selected from the group consisting of a polar solvent, a hydrophobic organic carrier, and a mixture thereof;
wherein the composition comprises no surfactant.

24. The method of claim 23, wherein the at least one organic carrier is about 17% to about 23% by weight of the composition.

25. A method of treating a dermatological or mucosal disorder, comprising applying a non-surfactant carrier composition to a surface in need of treatment for the dermatological or mucosal disorder, said composition comprising:
an active agent consisting of an antibiotic;
at least about 60% by weight of ethanol;
a cellulose ether;
a glycol;
an active herbal extract;
a metal; and
an antioxidant;
wherein the non-surfactant carrier composition is surfactant free.

26. The method of claim 25, wherein the glycol comprises propylene glycol.

27. The method of claim 26, wherein the glycol comprises propylene glycol between about 17% and about 23% by weight of the composition.

28. The method of claim 25, wherein the antibiotic comprises a tetracycline antibiotic, an erythromycin antibiotic, or a salt, ion, or complex thereof, and is about 0.1% to about 5% by weight of the composition; the cellulose ether comprises hydroxypropyl cellulose and is about 0.1% to about 5% by weight of the composition; and the glycol comprises propylene glycol and is about 17% to about 23% by weight of the composition.

29. The method of claim 23, wherein the disorder is acne or rosacea.

30. The method of claim 25, wherein the disorder is acne or rosacea.

31. The method of claim 28, wherein the antioxidant is about 0.1% to about 10% by weight of the composition.

32. The method of claim 28, wherein ethanol is at least about 65% by weight of the composition.

33. The method of claim 23, wherein the antibiotic is a tetracycline.

34. The method of claim 33, wherein the retinoid is adapalene.

35. The method of claim 23, wherein the at least one hydrophobic carrier comprises an alkyl ester of a fatty add.

36. The method of claim 23, wherein the antibiotic and/or retinoid is completely soluble in the composition.

37. The method of claim 25, wherein the antibiotic is completely soluble in the composition.

* * * * *

UNITED STATES PATENT AND TRADEMARK OFFICE
CERTIFICATE OF CORRECTION

PATENT NO. : 11,219,631 B2
APPLICATION NO. : 16/108799
DATED : January 11, 2022
INVENTOR(S) : Dov Tamarkin et al.

It is certified that error appears in the above-identified patent and that said Letters Patent is hereby corrected as shown below:

In the Claims

Claim 35, Column 52, Line 49, "add" should read as --acid--.

Signed and Sealed this
Twelfth Day of July, 2022

Katherine Kelly Vidal
*Director of the United States Patent and Trademark Office*